US009493774B2

(12) United States Patent
Kamens et al.

(10) Patent No.: US 9,493,774 B2
(45) Date of Patent: Nov. 15, 2016

(54) INHIBITION OF PCSK9 THROUGH RNAI

(75) Inventors: Joanne Kamens, Newton, MA (US);
Anastasia Khvorova, Westborough, MA (US)

(73) Assignee: RXi Pharmaceuticals Corporation, Marlsborough, MA (US)

( * ) Notice: Subject to any disclaimer, the term of this patent is extended or adjusted under 35 U.S.C. 154(b) by 278 days.

(21) Appl. No.: 13/143,275

(22) PCT Filed: Jan. 5, 2010

(86) PCT No.: PCT/US2010/000019
§ 371 (c)(1),
(2), (4) Date: Oct. 20, 2011

(87) PCT Pub. No.: WO2010/078536
PCT Pub. Date: Jul. 8, 2010

(65) Prior Publication Data
US 2013/0197055 A1 Aug. 1, 2013

Related U.S. Application Data

(60) Provisional application No. 61/204,348, filed on Jan. 5, 2009.

(51) Int. Cl.
| C12N 15/85 | (2006.01) |
| C07H 21/02 | (2006.01) |
| C07H 21/04 | (2006.01) |
| C12N 15/113 | (2010.01) |

(52) U.S. Cl.
CPC ....... *C12N 15/1137* (2013.01); *C12N 2310/14* (2013.01); *C12N 2310/315* (2013.01); *C12N 2310/3515* (2013.01); *C12N 2320/11* (2013.01); *C12Y 304/21061* (2013.01)

(58) Field of Classification Search
CPC .................. C12N 2310/321; C12N 2310/322; C12N 15/1137
See application file for complete search history.

(56) References Cited

U.S. PATENT DOCUMENTS

| 4,201,860 A | 5/1980 | Naito et al. |
| 4,235,871 A | 11/1980 | Papahadjopoulos et al. |
| 4,415,732 A | 11/1983 | Caruthers et al. |
| 4,426,330 A | 1/1984 | Sears |
| 4,501,728 A | 2/1985 | Geho et al. |
| 4,737,323 A | 4/1988 | Martin et al. |
| 4,837,028 A | 6/1989 | Allen |
| 4,897,355 A | 1/1990 | Eppstein et al. |
| 4,904,582 A | 2/1990 | Tullis |
| 4,958,013 A | 9/1990 | Letsinger |
| 5,023,243 A | 6/1991 | Tullis |
| 5,112,963 A | 5/1992 | Pieles et al. |
| 5,416,203 A | 5/1995 | Letsinger |
| 5,417,978 A | 5/1995 | Tari et al. |
| 5,432,272 A | 7/1995 | Benner |
| 5,459,255 A | 10/1995 | Cook et al. |
| 5,466,786 A | 11/1995 | Buhr et al. |
| 5,486,603 A | 1/1996 | Buhr |
| 5,514,786 A | 5/1996 | Cook et al. |
| 5,534,259 A | 7/1996 | Zalipsky et al. |
| 5,556,948 A | 9/1996 | Tagawa et al. |
| 5,578,718 A | 11/1996 | Cook et al. |
| 5,580,731 A | 12/1996 | Chang et al. |
| 5,580,972 A | 12/1996 | Tu et al. |
| 5,587,469 A | 12/1996 | Cook et al. |
| 5,591,721 A | 1/1997 | Agrawal et al. |
| 5,591,722 A | 1/1997 | Montgomery et al. |
| 5,591,843 A | 1/1997 | Eaton |
| 5,594,121 A | 1/1997 | Froehler et al. |
| 5,596,091 A | 1/1997 | Switzer |
| 5,614,617 A | 3/1997 | Cook et al. |
| 5,633,360 A | 5/1997 | Bischofberger et al. |
| 5,643,889 A | 7/1997 | Suhadolnik et al. |
| 5,646,126 A | 7/1997 | Cheng et al. |
| 5,646,265 A | 7/1997 | McGee |

(Continued)

FOREIGN PATENT DOCUMENTS

| AU | 2004206255 B2 | 8/2004 |
| CN | 1 568 373 A | 1/2005 |

(Continued)

OTHER PUBLICATIONS

Bertrand et al. (Biochemical and Biophysical Research Communications, 296, 2002, 1000-1004).*
[No Author Listed] RedChip Small-Cap Investor Conference. RXI Pharmaceuticals (Nasdaq RXII). Jun. 16, 2009 Presentation. 5 pages.
Abifadel et al., Mutations in PCSK9 cause autosomal dominant hypercholesterolemia. Nat Genet. Jun. 2003;34(2):154-6.
Aleckovic et al., RNAi at Oxford. J RNAi Gene Silencing. May 27, 2008;4(1):266-8.

(Continued)

*Primary Examiner* — Amy Bowman
(74) *Attorney, Agent, or Firm* — Wolf, Greenfield & Sacks, P.C.

(57) ABSTRACT

The invention relates to various PCSK9 RNAi constructs with gene silencing activities, and uses thereof. The construct has a double-stranded region of 19-49 nucleotides, preferably 25, 26, or 27 nucleotides, and preferably blunt-ended. The construct has selective minimal modifications to confer an optimal balance of biological activity, toxicity, stability, and target gene specificity. The sense strand may be modified such that the construct is not cleaved by Dicer or other RNAse III, and the entire length of the antisense strand is loaded into RISC. In addition, the antisense strand may also be modified by 2'-O-methyl groups at the 2nd 5'-end nucleotide to greatly reduce off-target silencing. The constructs of the invention largely avoid the interferon response and sequence-independent apoptosis in mammalian cells, exhibits better serum stability, and enhanced target specificity.

10 Claims, 7 Drawing Sheets

(56) References Cited

U.S. PATENT DOCUMENTS

| | | | |
|---|---|---|---|
| 5,658,731 A | 8/1997 | Sproat et al. | |
| 5,670,633 A | 9/1997 | Cook et al. | |
| 5,674,683 A | 10/1997 | Kool | |
| 5,681,940 A | 10/1997 | Wang et al. | |
| 5,681,941 A | 10/1997 | Cook et al. | |
| 5,684,143 A | 11/1997 | Gryaznov et al. | |
| 5,700,920 A | 12/1997 | Altmann et al. | |
| 5,466,786 B1 | 4/1998 | Buhr et al. | |
| 5,736,392 A | 4/1998 | Hawley-Nelson et al. | |
| 5,767,099 A | 6/1998 | Harris et al. | |
| 5,777,153 A | 7/1998 | Lin et al. | |
| 5,780,053 A | 7/1998 | Ashley et al. | |
| 5,789,416 A | 8/1998 | Lum et al. | |
| 5,792,847 A | 8/1998 | Buhr et al. | |
| 5,830,430 A | 11/1998 | Unger et al. | |
| 5,830,653 A | 11/1998 | Froehler et al. | |
| 5,851,548 A | 12/1998 | Dattagupta et al. | |
| 5,855,910 A | 1/1999 | Ashley et al. | |
| 5,856,455 A | 1/1999 | Cook | |
| 5,914,396 A | 6/1999 | Cook et al. | |
| 5,948,767 A | 9/1999 | Scheule et al. | |
| 5,969,116 A | 10/1999 | Martin | |
| 5,976,567 A | 11/1999 | Wheeler et al. | |
| 5,981,501 A | 11/1999 | Wheeler et al. | |
| 6,001,841 A | 12/1999 | Cook et al. | |
| 6,005,096 A | 12/1999 | Matteucci et al. | |
| 6,020,483 A | 2/2000 | Beckvermit et al. | |
| 6,028,183 A | 2/2000 | Lin et al. | |
| 6,043,352 A | 3/2000 | Manoharan et al. | |
| 6,107,094 A | 8/2000 | Crooke | |
| 6,111,085 A | 8/2000 | Cook et al. | |
| 6,153,737 A | 11/2000 | Manoharan et al. | |
| 6,207,819 B1 | 3/2001 | Manoharan et al. | |
| 6,271,358 B1 | 8/2001 | Manoharan et al. | |
| 6,326,358 B1 | 12/2001 | Manoharan | |
| 6,335,434 B1 | 1/2002 | Guzaev et al. | |
| 6,355,787 B1 | 3/2002 | Beckvermit et al. | |
| 6,358,931 B1 | 3/2002 | Cook et al. | |
| 6,395,492 B1 | 5/2002 | Manoharan et al. | |
| 6,399,754 B1 | 6/2002 | Cook | |
| 6,420,549 B1 | 7/2002 | Cook et al. | |
| 6,432,963 B1 | 8/2002 | Hisamichi et al. | |
| 6,444,806 B1 | 9/2002 | Veerapanani et al. | |
| 6,476,205 B1 | 11/2002 | Buhr et al. | |
| 6,506,559 B1 | 1/2003 | Fire et al. | |
| 6,528,631 B1 | 3/2003 | Cook et al. | |
| 6,531,584 B1 | 3/2003 | Cook et al. | |
| 6,673,611 B2 | 1/2004 | Thompson et al. | |
| 6,683,167 B2 | 1/2004 | Metelev et al. | |
| 6,815,432 B2 | 11/2004 | Wheeler et al. | |
| 6,849,726 B2 | 2/2005 | Usman et al. | |
| 6,858,225 B2 | 2/2005 | Semple et al. | |
| 7,041,824 B2 | 5/2006 | Bordon-Pallier et al. | |
| 7,056,704 B2 | 6/2006 | Tuschl et al. | |
| 7,078,196 B2 | 7/2006 | Tuschl et al. | |
| 7,205,297 B2 | 4/2007 | Beauchamp et al. | |
| 7,432,250 B2 | 10/2008 | Crooke | |
| 7,538,095 B2 | 5/2009 | Fire et al. | |
| 7,560,438 B2 | 7/2009 | Fire et al. | |
| 7,595,387 B2 | 9/2009 | Leake et al. | |
| 7,605,251 B2 | 10/2009 | Tan et al. | |
| 7,622,633 B2 | 11/2009 | Fire et al. | |
| 7,629,321 B2 | 12/2009 | Crooke | |
| 7,695,902 B2 | 4/2010 | Crooke | |
| 7,745,608 B2 | 6/2010 | Manoharan et al. | |
| 7,750,144 B2 | 7/2010 | Zamore et al. | |
| 7,786,290 B2 | 8/2010 | Woppmann et al. | |
| 7,829,693 B2 | 11/2010 | Kreutzer et al. | |
| 8,084,437 B2 * | 12/2011 | Freier et al. | 514/44 R |
| 8,110,674 B2 | 2/2012 | Manoharan et al. | |
| 8,263,569 B2 | 9/2012 | Baulcombe et al. | |
| 8,664,189 B2 | 3/2014 | Khvorova et al. | |
| 8,796,443 B2 | 8/2014 | Khvorova et al. | |
| 8,815,818 B2 | 8/2014 | Samarsky et al. | |
| 9,074,211 B2 | 7/2015 | Woolf et al. | |
| 9,080,171 B2 | 7/2015 | Khvorova et al. | |
| 9,095,504 B2 | 8/2015 | Libertine et al. | |
| 9,175,289 B2 | 11/2015 | Khvorova et al. | |
| 9,303,259 B2 | 4/2016 | Khvorova et al. | |
| 9,340,786 B2 | 5/2016 | Khvorova et al. | |
| 2002/0132788 A1 | 9/2002 | Lewis et al. | |
| 2002/0147332 A1 | 10/2002 | Kaneko et al. | |
| 2002/0160393 A1 | 10/2002 | Symonds et al. | |
| 2002/0162126 A1 | 10/2002 | Beach et al. | |
| 2003/0004325 A1 | 1/2003 | Cook et al. | |
| 2003/0077829 A1 | 4/2003 | MacLachlan | |
| 2003/0108923 A1 | 6/2003 | Tuschl et al. | |
| 2003/0139585 A1 | 7/2003 | Uhlmann et al. | |
| 2003/0157030 A1 | 8/2003 | Davis et al. | |
| 2003/0158403 A1 | 8/2003 | Manoharan et al. | |
| 2003/0166282 A1 | 9/2003 | Brown et al. | |
| 2003/0180756 A1 | 9/2003 | Shi et al. | |
| 2004/0009938 A1 | 1/2004 | Manoharan et al. | |
| 2004/0014956 A1 | 1/2004 | Woolf et al. | |
| 2004/0014957 A1 | 1/2004 | Eldrup et al. | |
| 2004/0018999 A1 | 1/2004 | Beach et al. | |
| 2004/0054155 A1 | 3/2004 | Woolf et al. | |
| 2004/0137471 A1 | 7/2004 | Vickers et al. | |
| 2004/0167090 A1 | 8/2004 | Monahan et al. | |
| 2004/0171033 A1 | 9/2004 | Baker et al. | |
| 2004/0180351 A1 | 9/2004 | Giese et al. | |
| 2004/0192629 A1 | 9/2004 | Xu et al. | |
| 2004/0204377 A1 | 10/2004 | Rana | |
| 2004/0229266 A1 | 11/2004 | Tuschl et al. | |
| 2004/0241845 A1 | 12/2004 | Desgroseillers et al. | |
| 2004/0248839 A1 | 12/2004 | Kowalik | |
| 2004/0259247 A1 | 12/2004 | Tuschl et al. | |
| 2005/0020521 A1 | 1/2005 | Rana | |
| 2005/0026286 A1 | 2/2005 | Chi et al. | |
| 2005/0032733 A1 | 2/2005 | McSwiggen et al. | |
| 2005/0080246 A1 | 4/2005 | Allerson et al. | |
| 2005/0107325 A1 | 5/2005 | Manoharan et al. | |
| 2005/0142535 A1 | 6/2005 | Damha et al. | |
| 2005/0181382 A1 | 8/2005 | Zamore et al. | |
| 2005/0239731 A1 | 10/2005 | McSwiggen et al. | |
| 2005/0245474 A1 | 11/2005 | Baker et al. | |
| 2005/0255487 A1 | 11/2005 | Khvorova et al. | |
| 2006/0009409 A1 | 1/2006 | Woolf | |
| 2006/0035344 A1 | 2/2006 | Pachuk et al. | |
| 2006/0069050 A1 | 3/2006 | Rana | |
| 2006/0142228 A1 | 6/2006 | Ford et al. | |
| 2006/0178324 A1 | 8/2006 | Hadwiger et al. | |
| 2006/0178327 A1 | 8/2006 | Yeung | |
| 2007/0032441 A1 | 2/2007 | McSwiggen et al. | |
| 2007/0166734 A1 | 7/2007 | Bhat et al. | |
| 2007/0173473 A1 | 7/2007 | McSwiggen et al. | |
| 2007/0173476 A1 | 7/2007 | Leake et al. | |
| 2007/0231392 A1 | 10/2007 | Wagner et al. | |
| 2007/0269889 A1 | 11/2007 | Leake et al. | |
| 2008/0008697 A1 | 1/2008 | Mintier et al. | |
| 2008/0071068 A1 | 3/2008 | Oba et al. | |
| 2008/0085869 A1 | 4/2008 | Yamada et al. | |
| 2008/0293142 A1 | 11/2008 | Liu et al. | |
| 2008/0306015 A1 | 12/2008 | Khvorova et al. | |
| 2008/0311040 A1 | 12/2008 | Berry et al. | |
| 2009/0023216 A1 | 1/2009 | Woolf | |
| 2009/0131360 A1 | 5/2009 | Woolf et al. | |
| 2009/0208564 A1 | 8/2009 | Li et al. | |
| 2009/0306005 A1 | 12/2009 | Bhanot et al. | |
| 2009/0306184 A1 * | 12/2009 | McSwiggen et al. | 514/44 A |
| 2010/0069620 A1 | 3/2010 | Zon | |
| 2010/0136695 A1 | 6/2010 | Woolf | |
| 2011/0039914 A1 | 2/2011 | Pavco et al. | |
| 2011/0237522 A1 | 9/2011 | Khvorova et al. | |
| 2011/0237648 A1 | 9/2011 | Khvorova et al. | |
| 2011/0251258 A1 | 10/2011 | Samarsky et al. | |
| 2011/0263680 A1 | 10/2011 | Khvorova et al. | |
| 2012/0016005 A1 | 1/2012 | Samarsky et al. | |
| 2012/0040459 A1 | 2/2012 | Khvorova et al. | |
| 2012/0059046 A1 | 3/2012 | Woolf et al. | |
| 2012/0065243 A1 | 3/2012 | Woolf et al. | |
| 2013/0131141 A1 | 5/2013 | Khvorova et al. | |
| 2013/0131142 A1 | 5/2013 | Libertine et al. | |
| 2014/0113950 A1 | 4/2014 | Khvorova et al. | |

(56) References Cited

U.S. PATENT DOCUMENTS

| | | | |
|---|---|---|---|
| 2014/0315974 | A1 | 10/2014 | Khvorova et al. |
| 2014/0364482 | A1 | 12/2014 | Khvorova et al. |
| 2016/0115482 | A1 | 4/2016 | Libertine et al. |
| 2016/0115484 | A1 | 4/2016 | Woolf et al. |
| 2016/0130578 | A1 | 5/2016 | Khvorova et al. |

FOREIGN PATENT DOCUMENTS

| | | |
|---|---|---|
| EP | 1 214 945 A2 | 6/2002 |
| EP | 1 144 623 B9 | 3/2003 |
| EP | 1 352 061 B1 | 10/2003 |
| EP | 0 928 290 B9 | 3/2005 |
| EP | 1 407 044 B1 | 9/2007 |
| EP | 1 605 978 B1 | 9/2010 |
| JP | 4 095 895 B2 | 9/2004 |
| JP | 2009-519033 | 5/2009 |
| WO | WO 90/14074 A1 | 11/1990 |
| WO | WO 91/16024 A1 | 10/1991 |
| WO | WO 91/17424 A1 | 11/1991 |
| WO | WO 92/03464 A1 | 3/1992 |
| WO | WO 94/23028 A2 | 10/1994 |
| WO | WO 95/11910 A1 | 5/1995 |
| WO | WO 95/23162 A1 | 8/1995 |
| WO | WO 96/40964 A2 | 12/1996 |
| WO | WO 03/012052 A2 | 2/2003 |
| WO | WO 2004/001044 A1 | 12/2003 |
| WO | WO 2004/042027 A2 | 5/2004 |
| WO | WO 2004/065600 A2 | 8/2004 |
| WO | WO 2004/065601 A2 | 8/2004 |
| WO | WO 2004/090105 A1 | 10/2004 |
| WO | WO 2005/019430 A2 | 3/2005 |
| WO | WO 2005/019453 A2 | 3/2005 |
| WO | WO 2005/079533 A2 | 9/2005 |
| WO | WO 2005/097992 A2 | 10/2005 |
| WO | WO 2006/019430 A2 | 2/2006 |
| WO | WO 2006/039656 A2 | 4/2006 |
| WO | WO 2006/065601 A2 | 6/2006 |
| WO | WO 2006/128141 A2 | 11/2006 |
| WO | WO 2007/030167 A1 | 3/2007 |
| WO | WO 2007/044362 A2 | 4/2007 |
| WO | WO 2007/069068 A2 | 6/2007 |
| WO | WO 2007/089607 A2 | 8/2007 |
| WO | WO 2008/036825 A2 | 3/2008 |
| WO | WO 2008/109353 A1 | 9/2008 |
| WO | WO 2009/020344 A2 | 2/2009 |
| WO | WO 2009/029688 A3 | 3/2009 |
| WO | WO 2009/029690 A1 | 3/2009 |
| WO | WO 2009/044392 A2 | 4/2009 |
| WO | WO 2009/078685 A2 | 6/2009 |
| WO | WO 2009/102427 A2 | 8/2009 |
| WO | WO 2009/114475 A2 * | 9/2009 ............ 514/44 |
| WO | WO 2009/134487 A2 | 11/2009 |
| WO | WO 2010/011346 A1 | 1/2010 |
| WO | WO 2010/027830 A2 | 3/2010 |
| WO | WO 2010/033247 A2 | 3/2010 |
| WO | WO 2010/042281 A2 | 4/2010 |
| WO | WO 2011/109698 A1 | 9/2011 |

OTHER PUBLICATIONS

Anderson et al., Experimental validation of the importance of seed complement frequency to siRNA specificity. RNA. May 2008;14(5):853-61. doi: 10.1261/rna.704708. Epub Mar. 26, 2008.
Baigude et al., Design and creation of new nanomaterials for therapeutic RNAi. ACS Chem Biol. Apr. 24, 2007;2(4):237-41.
Bartzatt, Cotransfection of nucleic acid segments by Sendai virus envelopes. Biotechnol Appl Biochem. Feb. 1989;11(1):133-5.
Benjannet et al., NARC-1/PCSK9 and its natural mutants: zymogen cleavage and effects on the low density lipoprotein (LDL) receptor and LDL cholesterol. J Biol Chem. Nov. 19, 2004;279(47):48865-75. Epub Sep. 9, 2004.
Bergan et al., Electroporation enhances c-myc antisense oligodeoxynucleotide efficacy. Nucleic Acids Res. Jul. 25, 1993;21(15):3567-73.
Bergeron et al., Subtilase-like pro-protein convertases: from molecular specificity to therapeutic applications. J Mol Endocrinol. Feb. 2000;24(1):1-22.
Bjergarde et al., Solid phase synthesis of oligodeoxyribonucleoside phosphorodithioates from thiophosphoramidites. Nucleic Acids Res. Nov. 11, 1991;19(21):5843-50.
Boutorin et al., Synthesis of alkylating oligonucleotide derivatives containing cholesterol or phenazinium residues at their 3'-terminus and their interaction with DNA within mammalian cells. FEBS Lett. Aug. 28, 1989;254(1-2):129-32.
Braasch et al., RNA Interference in Mammalian Cells by Chemically-Modified RNA. Biochem. 2003;42(26):7967-75.
Brown et al., Light at the end of the tunnel. J RNAi Gene Silencing. Jul. 28, 2006;2(2):175-7.
Chang, An economic and efficient method of RNAi vector constructions. Anal Biochem. Nov. 1, 2004;334(1):199-200.
Chiu et al., siRNA function in RNAi: a chemical modification analysis. RNA. Sep. 2003;9(9):1034-48.
Choung et al. Chemical modification of siRNAs to improve serum stability without loss of efficacy. Biochem Biophys Res Commun. Apr. 14, 2006;342(3):919-27.
Chu et al., Potent RNAi by short RNA triggers. RNA. 2008;14:1714-9.
Cohen et al., Low LDL cholesterol in individuals of African descent resulting from frequent nonsense mutations in PCSK9. Nat Genet. Feb. 2005;37(2):161-5. Epub Jan. 16, 2005.
Cohen et al., Molecular mechanisms of autosomal recessive hypercholesterolemia. Curr Opin Lipidol. Apr. 2003;14(2):121-7.
Cohen et al., Sequence variations in PCSK9, low LDL, and protection against coronary heart disease. N Engl J Med. Mar. 23, 2006;354(12):1264-72.
Constantinides et al., Formulation and intestinal absorption enhancement evaluation of water-in-oil microemulsions incorporating medium-chain glycerides. Pharm Res. Oct. 1994;11(10):1385-90.
Czauderna et al., Structural variations and stabilising modifications of synthetic siRNAs in mammalian cells. Nucleic Acids Res. Jun. 1, 2003;31(11):2705-16.
De Smidt et al., Association of antisense oligonucleotides with lipoproteins prolongs the plasma half-life and modifies the tissue distribution. Nucleic Acids Res. Sep. 11, 1991;19(17):4695-700.
Debart et al., Chemical modifications to improve the cellular uptake of oligonucleotides. Curr Top Med Chem. 2007;7(7):727-37.
Dubuc et al., Statins upregulate PCSK9, the gene encoding the proprotein convertase neural apoptosis-regulated convertase-1 implicated in familial hypercholesterolemia. Arterioscler Thromb Vasc Biol. Aug. 2004;24(8):1454-9. Epub Jun. 3, 2004.
Durand et al., Circular dichroism studies of an oligodeoxyribonucleotide containing a hairpin loop made of a hexaethylene glycol chain: conformation and stability. Nucleic Acids Res. Nov. 11, 1990;18(21):6353-9.
Dykxhoorn et al., The silent treatment: siRNAs as small molecule drugs. Gene Ther. Mar. 2006;13(6):541-52.
Elbashir et al., Duplexes of 21-nucleotide RNAs mediate RNA interference in cultured mammalian cells. Nature. May 24, 2001;411(6836):494-8.
Elbashir et al., Functional anatomy of siRNAs for mediating efficient RNAi in Drosophila melanogaster embryo lysate. EMBO J. Dec. 3, 2001;20(23):6877-88.
Fedorov et al., Off-target effects by siRNA can induce toxic phenotype. RNA. Jul. 2006;12(7):1188-96. Epub May 8, 2006.
Ferentz et al., Disulfide-crosslinked oligonucleotides. Journal of the American Chemical Society. 1991;113 (10): 4000-4002.
Frank-Kamenetsky et al., Therapeutic RNAi targeting PCSK9 acutely lowers plasma cholesterol in rodents and LDL cholesterol in nonhuman primates. Proc Natl Acad Sci U S A. Aug. 19, 2008;105(33):11915-20. doi: 10.1073/pnas.0805434105. Epub Aug. 11, 2008.

(56) References Cited

OTHER PUBLICATIONS

Gensberg et al., Subtilisin-related serine proteases in the mammalian constitutive secretory pathway. Semin Cell Dev Biol. Feb. 1998;9(1):11-7.

Harborth et al., Sequence, chemical, and structural variation of small interfering RNAs and short hairpin RNAs and the effect on mammalian gene silencing. Antisense Nucleic Acid Drug Dev. Apr. 2003;13(2):83-105.

Ho et al., Preparation of microemulsions using polyglycerol fatty acid esters as surfactant for the delivery of protein drugs. J Pharm Sci. Feb. 1996;85(2):138-43.

Horton et al., Combined analysis of oligonucleotide microarray data from transgenic and knockout mice identifies direct SREBP target genes. Proc Natl Acad Sci U S A. Oct. 14, 2003;100(21):12027-32. Epub Sep. 25, 2003.

Hosono et at., Properties of base-pairing in the stem region of hairpin antisense oligonucleotides containing 2'-methoxynucleosides. Biochim Biophys Acta. Jun. 9, 1995;1244(2-3):339-44.

Huang et al., Lipitoids—novel cationic lipids for cellular delivery of plasmid DNA in vitro. Chem Biol. Jun. 1998;5(6):345-54.

Jackson et al., Position-specific chemical modification of siRNAs reduces "off-target" transcript silencing. RNA. Jul. 2006;12(7):1197-1205. Epub May 8, 2006.

Kamata et al., Amphiphilic peptides enhance the efficiency of liposome-mediated DNA transfection. Nucleic Acids Res. Feb. 11, 1994;22(3):536-7.

Kim et al., Synthetic dsRNA Dicer substrates enhance RNAi potency and efficacy. Nat Biotechnol. Feb. 2005;23(2):222-6. Epub Dec. 26, 2004.

Kim et al., Systemic and specific delivery of small interfering RNAs to the liver mediated by apolipoprotein A-I. Mol Ther. Jun. 2007;15(6):1145-52. Epub Apr. 17, 2007.

Kraynack et al., Small interfering RNAs containing full 2'-O-methylribonucleotide-modified sense strands display Argonaute2/eIF2C2-dependent activity. RNA. Jan. 2006;12(1):163-76. Epub Nov. 21, 2005.

Kubo et al., Modified 27-nt dsRNAs with dramatically enhanced stability in serum and long-term RNAi activity. Oligonucleotides. 2007 Winter;17(4):445-64.

Layzer et al., In vivo activity of nuclease-resistant siRNAs. RNA. May 2004;10(5):766-71.

Lee et al., Contributions of 3'-overhang to the dissociation of small interfering RNAs from the PAZ domain: molecular dynamics simulation study. J Mol Graph Model. Mar. 2007;25(6):784-93. Epub Jul. 11, 2006.

Lemaitre et al., Specific antiviral activity of a poly(L-lysine)-conjugated oligodeoxyribonucleotide sequence complementary to vesicular stomatitis virus N protein mRNA initiation site. Proc Natl Acad Sci U S A. Feb. 1987;84(3):648-52.

Leren, Mutations in the PCSK9 gene in Norwegian subjects with autosomal dominant hypercholesterolemia. Clin Genet. May 2004;65(5):419-22.

Letsinger et al., Cholesteryl-conjugated oligonucleotides: synthesis, properties, and activity as inhibitors of replication of human immunodeficiency virus in cell culture. Proc Natl Acad Sci U S A. Sep. 1989;86(17):6553-6.

Leuschner et al., Cleavage of the siRNA passenger strand during RISC assembly in human cells. EMBO Rep. Mar. 2006;7(3):314-20. Epub Jan. 20, 2006.

Lewis et al., A serum-resistant cytofectin for cellular delivery of antisense oligodeoxynucleotides and plasmid DNA. Proc Natl Acad Sci U S A. Apr. 16, 1996;93(8):3176-81.

Li et al., Surface-modified LPD nanoparticles for tumor targeting. Ann N Y Acad Sci. Oct. 2006;1082:1-8.

Ma et al., Design and synthesis of RNA miniduplexes via a synthetic linker approach. 2. Generation of covalently closed, double-stranded cyclic HIV-1 TAR RNA analogs with high Tat-binding affinity. Nucleic Acids Res. Jun. 11, 1993;21(11):2585-9.

MacRae et al., Structure of Dicer and mechanistic implications for RNAi. Cold Spring Harb Symp Quant Biol. 2006;71:73-80.

Manoharan et al., Chemical modifications to improve uptake and bioavailability of antisense oligonucleotides. Ann N Y Acad Sci. Oct. 28, 1992;660:306-9.

Manoharan, Oligonucleotide conjugates as potential antisense drugs with improved uptake, biodistribution, targeted delivery, and mechanism of action. Antisense Nucleic Acid Drug Dev. Apr. 2002;12(2):103-28.

Martins et al., Sterol side chain length and structure affect the clearance of chylomicron-like lipid emulsions in rats and mice. J Lipid Res. Feb. 1998;39(2):302-12.

Mathews et al., Incorporating chemical modification constraints into a dynamic programming algorithm for prediction of RNA secondary structure. Proc Natl Acad Sci U S A. May 11, 2004;101(19):7287-92. Epub May 3, 2004.

Maxwell et al., Novel putative SREBP and LXR target genes identified by microarray analysis in liver of cholesterol-fed mice. J Lipid Res. Nov. 2003;44(11):2109-19. Epub Aug. 1, 2003.

Maxwell et al., Adenoviral-mediated expression of PCSK9 in mice results in a low-density lipoprotein receptor knockout phenotype. Proc Natl Acad Sci U S A. May 4, 2004;101(18):7100-5. Epub Apr. 26, 2004.

Murchison et al., Characterization of Dicer-deficient murine embryonic stem cells. Proc Natl Acad Sci U S A. Aug. 23, 2005;102(34):12135-40. Epub Aug. 12, 2005.

Murphy et al., A combinatorial approach to the discovery of efficient cationic peptoid reagents for gene delivery. Proc Natl Acad Sci U S A. Feb. 17, 1998;95(4):1517-22.

Oberhauser et al., Effective incorporation of 2'-O-methyl-oligoribonucleotides into liposomes and enhanced cell association through modification with thiocholesterol. Nucleic Acids Res. Feb. 11, 1992;20(3):533-8.

Park et al., Post-transcriptional regulation of low density lipoprotein receptor protein by proprotein convertase subtilisin/kexin type 9a in mouse liver. J Biol Chem. Nov. 26, 2004;279(48):50630-8. Epub Sep. 22, 2004.

Parrish et al., Functional anatomy of a dsRNA trigger: differential requirement for the two trigger strands in RNA interference. Mol Cell. Nov. 2000;6(5):1077-87.

Rader et al., Monogenic hypercholesterolemia: new insights in pathogenesis and treatment. J Clin Invest. Jun. 2003;111(12):1795-803.

Rajeev et al., 2'-modified-2-thiothymidine oligonucleotides. Org Lett. Aug. 21, 2003;5(17):3005-8.

Rashid et al., Decreased plasma cholesterol and hypersensitivity to statins in mice lacking Pcsk9. Proc Natl Acad Sci U S A. Apr. 12, 2005;102(15):5374-9. Epub Apr. 1, 2005.

Reichhart et al., Splice-activated UAS hairpin vector gives complete RNAi knockout of single or double target transcripts in *Drosophila melanogaster*. Genesis. Sep.-Oct. 2002;34(1-2):160-4.

Rump et al., Preparation of conjugates of oligodeoxynucleotides and lipid structures and their interaction with low-density lipoprotein. Bioconjug Chem. May-Jun. 1998;9(3):341-9.

Sato et al., Tumor targeting and imaging of intraperitoneal tumors by use of antisense oligo-DNA complexed with dendrimers and/or avidin in mice. Clin Cancer Res. Nov. 2001;7(11):3606-12.

Schaniel et al., Delivery of short hairpin RNAs—triggers of gene silencing—into mouse embryonic stem cells. Nat Methods. May 2006;3(5):397-400.

Schell et al., Stimulation of the uptake of polynucleotides by poly(L-lysine). Biochim Biophys Acta. Mar. 27, 1974;340(3):323-33.

Seela et al., Oligodeoxyribonucleotides containing 1,3-propanediol as nucleoside substitute. Nucleic Acids Res. Apr. 10, 1987;15(7):3113-29.

Seidah et al., Proprotein and prohormone convertases: a family of subtilases generating diverse bioactive polypeptides. Brain Res. Nov. 27, 1999;848(1-2):45-62.

Shi, Mammalian RNAi for the masses. Trends Genet. Jan. 2003;19(1):9-12.

Shioji et al., Genetic variants in PCSK9 affect the cholesterol level in Japanese. J Hum Genet. 2004;49(2):109-14. Epub Jan. 15, 2004.

(56) References Cited

OTHER PUBLICATIONS

Siolas et al., Synthetic shRNAs as potent RNAi triggers. Nat Biotechnol. Feb. 2005;23(2):227-31. Epub Dec. 26, 2004.
Soutschek et al., Therapeutic silencing of an endogenous gene by systemic administration of modified siRNAs. Nature. Nov. 11, 2004;432(7014):173-8.
Sui et al., A DNA vector-based RNAi technology to suppress gene expression in mammalian cells. Proc Natl Acad Sci U S A. Apr. 16, 2002;99(8):5515-20.
Sun et al., Asymmetric RNA duplexes mediate RNA interference in mammalian cells. Nat Biotechnol. Dec. 2008;26(12):1379-82. doi: 10.1038/nbt.1512. Epub Nov. 23, 2008.
Taylor et al., Curbing activation: proprotein convertases in homeostasis and pathology. FASEB J. Jul. 2003;17(10):1215-27.
Timms et al., A mutation in PCSK9 causing autosomal-dominant hypercholesterolemia in a Utah pedigree. Hum Genet. Mar. 2004;114(4):349-53. Epub Jan. 15, 2004.
Uhlmann et al., Antisense oligonucleotides: a new therapeutic principle. Chem Rev. 1990;90(4):543-84.
Vlassov et al., Transport of oligonucleotides across natural and model membranes. Biochim Biophys Acta. Jun. 29, 1994;1197(2):95-108.
Wagner et al., Transferrin-polycation-DNA complexes: the effect of polycations on the structure of the complex and DNA delivery to cells. Proc Natl Acad Sci U S A. May 15, 1991;88(10):4255-9.
Wolfrum et al., Mechanisms and optimization of in vivo delivery of lipophilic siRNAs. Nat Biotechnol. Oct. 2007;25(10):1149-57. Epub Sep. 16, 2007.
Yamada et al., Synthesis and properties of oligonucleotides having a chemically stable 2-(trimethylsilyl)benzoyl group. Nucleic Acids Symp Ser (Oxf). 2008;(52):301-2. doi: 10.1093/nass/nrn152.
Yu et al., RNA interference by expression of short-interfering RNAs and hairpin RNAs in mammalian cells. Proc Natl Acad Sci U S A. Apr. 30, 2002;99(9):6047-52. Epub Apr. 23, 2002.
Zhou et al., Proteolytic processing in the secretory pathway. J Biol Chem. Jul. 23, 1999;274(30):20745-8.
Zuckermann et al., Design, construction and application of a fully automated equimolar peptide mixture synthesizer. Int J Pept Protein Res. Dec. 1992;40(6):497-506.
Zuckermann et al., Efficient method for the preparation of peptoids [oligo(N-substituted glycines)] by submonomer solid-phase synthesis. Journal of the American Chemical Society. 1992;114(26):10646-10647.
U.S. Appl. No. 13/636,755, filed Sep. 24, 2012, Khvorova et al.
PCT/US2010/000019, Mar. 22, 2010, International Search Report and Written Opinion.
PCT/US2010/000019, Jul. 14, 2011, International Preliminary Report on Patentability.
U.S. Appl. No. 14/104,450, filed Dec. 12, 2013, Khvorova et al.
U.S. Appl. No. 14/278,900, filed May 15, 2014, Khvorova et al.
[No Author Listed], Rxi Pharmaceuticals Presents Self-Delivering RNAi Data at Scar Club Meeting in France. Drugs.com. Mar. 26, 2010. http://www.drugs.com/clinical_trials/rxi-pharmaceuticals-presents-self-delivering-rnai-data-scar-club-meeting-france-9093.html [last accessed Aug. 19, 2014].
U.S. Appl. No. 14/866,681, filed Sep. 25, 2015, Khvorova et al.
U.S. Appl. No. 14/728,764, filed Jun. 2, 2015, Woolf et al.
U.S. Appl. No. 14/729,006, filed Jun. 2, 2015, Khvorova et al.
U.S. Appl. No. 14/728,653, filed Jun. 2, 2015, Libertine et al.
Vermeulen et al., The contributions of dsRNA structure to Dicer specificity and efficiency. RNA. May 2005;11(5):674-82. Epub Apr. 5, 2005.

* cited by examiner

INHIBITION OF PCSK9 THROUGH RNAI

RELATED APPLICATIONS

This application is a national stage filing under 35 U.S.C. §371 of international application PCT/US2010/000019, filed Jan. 5, 2010, which was published under PCT Article 21(2) in English, and claims the benefit under 35 U.S.C. §119(e) of U.S. Provisional Application Ser. No. 61/204,348, entitled "INHIBITION OF PCSK9 THROUGH RNAI," filed on Jan. 5, 2009, the disclosures of which are herein incorporated by reference in their entireties.

BACKGROUND OF THE INVENTION

Proprotein convertase subtilisin kexin 9 (PCSK9) is a member of the subtilisin serine protease family. The other eight mammalian subtilisin proteases, PCSK1-PCSK8 (also called PC1/3, PC2, furin, PC4, PC5/6, PACE4, PC7, and S1P/SKI-1) are proprotein converges that process a wide variety of proteins in the secretory pathway and play roles in diverse biological processes (Bergeron, F. (2000) *J. Mol. Endocrinol.* 24, 1-22, Gensberg, K., (1998) *Semin. Cell Dev. Biol.* 9, 11-17, Seidah, N. G. (1999) *Brain Res.* 848, 45-62, Taylor, N. A., (2003) *FASEB* 17, 1215-1227, and Zhou, A., (1999) *J. Biol. Chem.* 274, 20745-20748). PCSK9 has been proposed to play a role in cholesterol metabolism. PCSK9 mRNA expression is down-regulated by dietary cholesterol feeding in mice (Maxwell, K, N., (2003) *J. Lipid Res.* 44, 2109-2119), up-regulated by statins in HepG2 cells (Dubuc, G., (2004) *Arterioscler. Thromb. Vase. Biol.* 24, 1454-1459), and up-regulated in sterol regulatory element binding protein (SREBF) transgenic mice (Horton, J, D., (2003) *Proc. Natl. Acad. Sci. USA* 100, 12027-12032), similar to the cholesterol biosynthetic enzymes and the low-density lipoprotein receptor (LDLR). Furthermore, PCSK9 missense mutations have been found to be associated with a form of autosomal dominant hypercholesterolemia (Hchola3) (Abifadel, M., et at (2003) *Nat. Genet,* 34, 154-156, Timms, K. M., (2004) *Hum. Genet.* 114, 349-353, Leren, T. P. (2004) *Clin. Genet.* 65, 419-422), PCSK9 may also play a role in determining LDL cholesterol levels in the general population, because single-nucleotide polymorphisms (SNPs) have been associated with cholesterol levels in a Japanese population (Shioji, K., (2004) *J. Hum. Genet.* 49, 109-114).

Autosomal dominant hypercholesterolemias (ADHs) are monogenic diseases in which patients exhibit elevated total and LDL cholesterol levels, tendon xanthomas, and premature atherosclerosis (Rader, D. J., (2003) *J. Clin. Invest.* 111, 1795-1803). The pathogenesis of ADHs and a recessive form, autosomal recessive hypercholesterolemia (ARH) (Cohen, J. C., (2003) *Curr. Opin. Lipidol.* 14, 121-127), is due to defects in LDL uptake by the liver, ARH may be caused by LDLR mutations, which prevent LDL uptake, or by mutations in the protein on LDL, apolipoprotein B, which binds to the LDLR. ARH is caused by mutations in the ARM protein that are necessary for endocytosis of the LDLR-LDL complex via its interaction with clathrin. Therefore, if PCSK9 mutations are causative in Hchola3 families, it seems likely that PCSK9 plays a role in receptor-mediated LDL uptake.

Overexpression studies point to a role for PCSK9 in controlling LDLR levels and, hence, LDL uptake by the liver (Maxwell K. N. (2004) *Proc. Natl. Acad. Sci. USA* 101, 7100-7105, Benjannet, S., et al. (2004) *J. Biol. Chem.* 279, 48865-18875, Park, S. W., (2004) *J. Biol. Chem.* 279, 50630-50638). Adenoviral-mediated overexpression of mouse or human PCSK9 for 3 or 4 days in mice results in elevated total and LDL cholesterol levels; this effect is not seen in LDLR knockout animals (Maxwell K. N. (2004) *Proc. Natl. Acad. Sci. USA* 101, 7100-7105, Benjannet, S., et al. (2904) *J. Biol. Chem.* 279, 48865-48875, Park, S. W., (2004) *J. Biol. Chem.* 279, 50630-50638). In addition, PCSK9 overexpression results in a severe reduction in hepatic LDLR protein, without affecting IDLE mRNA levels, SREBP protein levels, or SREBP protein nuclear to cytoplasmic ratio. These results indicate that PCSK9, either directly or indirectly, reduces LDLR protein levels by a post transcriptional mechanism Loss of function mutations in PCSK9 have been designed in mouse models (Rashid et al., (2005) *PNAS,* 102, 5374-5379, and identified in human individuals Cohen et al., (2005), *Nature Genetics.,* 37.161-165. In both cases loss of PCSK9 function lead to lowering of total and LDLc cholesterol. In a retrospective outcome study over 15 years, loss of one copy of PCSK9 was shown to shift LDLc lower and to lead to an increased risk-benefit protection from developing cardiovascular heart disease (Cohen et al. 2006 *N. Engl. J. Med.,* 354, 1264-1272.). Clearly the evidence to date indicates that lowering of PCSK9 levels will lower LDLc.

Despite significant advances in the field of RNAi and advances in the treatment of pathological processes which can be mediated by down regulating PCSK9 gene expression; there remains a need for agents that can inhibit PCSK9 gene expression and that can treat diseases associated with PCSK9 gene expression.

SUMMARY OF THE INVENTION

The present invention is directed to RNAi constructs comprising PCSK9-specific sequences and methods pertaining to their use in PCSK9 silencing. Accordingly, the present invention provides compositions and methods for increasing the efficiency of inhibiting PCSK9 expression through RNA interference.

In one aspect, the present invention relates to an RNAi construct for inhibiting expression of a PCSK9 gene, comprising a guide sequence that hybridizes to a target sequence on an mRNA of the PCSK9 gene and inhibits the expression of the PCSK9 gene through an RNA interference mechanism, wherein said target sequence is selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53-79, 94, 96, 98 and 100. In some embodiments, the target sequence is selected from the group consisting of SEQ ID NOs: 11, 19, 23, 25, 53, 55, 57, 59, 61, 63, 65, 66, 67, 69, 94, 96, 98 and 100.

In one particular embodiment, the RNAi construct comprises a single-stranded polynucleotide that forms a hairpin structure which includes a double-stranded stem and a single-stranded loop, wherein the double-stranded stem can be cleaved by Dicer to produce an siRNA having a guide sequence that hybridizes to a sequence selected from SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53-79, 94, 96, 98 and 100. In some embodiments, the target sequence is selected from the group consisting of SEQ ID NOs: 11, 19, 23, 25, 53, 55, 57, 59, 61, 63, 65, 66, 67, 69, 94, 96, 98 and 100.

In another embodiment, the RNAi construct comprises an siRNA having a guide sequence selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 85, 87, 89, 91, 95, 97, 99 and 101.

In certain embodiments of the invention, the RNAi construct comprises a single-stranded polynucleotide that forms a hairpin structure. The hairpin structure includes a double-stranded stem and a single-stranded loop, wherein the double-stranded stem has a 5'-stem sequence having a 5'-end, and a 3'-stem sequence having a 3'-end. The 5'-stem sequence and at least a portion of said loop form the guide sequence that hybridizes to a sequence selected from SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53-79, 94, 96, 98 and 100. In some embodiments, the target sequence is selected from the group consisting of SEQ ID NOs: 11, 19, 23, 25, 53, 55, 57, 59, 61, 63, 65, 66, 67, 69, 94, 96, 98 and 100.

In a related embodiment, the 5'-stem sequence, the loop, and at least a portion of the 3'-stem sequence collectively form the guide sequence that hybridizes to a sequence selected from SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53-79, 94, 96, 98 and 100. In some embodiments, the target sequence is selected from the group consisting of SEQ ID NOs: 11, 19, 23, 25, 53, 55, 57, 59, 61, 63, 65, 66, 67, 69, 94, 96, 98 and 100.

In certain embodiments, the single-stranded polynucleotide is an RNA.

In certain embodiments, at least 12 nucleotides from the 5'-end of the single-stranded polynucleotide are 100% complementary to the target sequence.

In certain embodiments, at least one nucleotide is modified to improve resistance to nucleases, serum stability, target specificity, tissue distribution, and/or cell-permeability of the polynucleotide.

In certain embodiments, the modified nucleotides are modified on the sugar moiety, the base, and/or the phosphodiester linkage.

In certain embodiments, the modification is at position 2 from the 5'-end of the polynucleotide.

In certain embodiments, the modification is a 2'-O-alkyl or 2'-halo group.

In certain embodiments, the modification comprises 2'-O-methyl modification at alternative nucleotides, starting from either the first or the second nucleotide from the 5'-end.

In certain embodiments, the modification comprises 2'-O-methyl modification of one or more randomly selected pyrimidine nucleotides (C or U).

In certain embodiments, the modification comprises 2'-O-methyl modification of one or more nucleotides within the loop. For example, the modification is either limited to one or more nucleotides within the loop, or additionally including 1, 2, 3, 4, 5, or 6 more nucleotide(s) of the guide sequence within the double-stranded stem region just 5' to said loop.

In certain embodiments, the modification comprises 2'-O-methyl modification, wherein no more than 4 consecutive nucleotides are modified.

In certain embodiments, all nucleotides in the 3'-end stem region are modified.

In certain embodiments, all nucleotides in the sense sequence are modified.

In certain embodiments, the modification is a phosphate analog.

In certain embodiments, the modification is a phosphorothioate linkage.

In a related embodiment, the phosphorothioate linkage is limited to one or more nucleotides within said loop. In another aspect, the phosphorothioate linkage is limited to one or more nucleotides within said loop, and 1, 2, 3, 4, 5, or 6 more nucleotide(s) of the guide sequence within the double-stranded stem region just 5' to said loop.

In certain embodiments, the modification comprises hydrophobic modification to one or more bases. For example, said one or more bases are C or G. In one aspect, the hydrophobic modification comprises an isobutyl group.

In one embodiment, the guide sequence is about 15-21 nucleotides in length, or about 19-21 nucleotides in length.

In certain embodiments, the polynucleotide is 15-29 nucleotides in length, or about 25-26 nucleotides in length.

In another embodiment, the hairpin structure is not a substrate for Dicer.

In certain embodiments, the double-stranded stem of the hairpin structure is less than 21 base pairs in length. In another aspect, the double-stranded stem is less than about 20 base pairs in length, or is about 5-15 base pairs in length, or about 10 base pairs in length. In certain embodiments, the double-stranded stem is at least 11 base pairs in length, preferably at least 12 base pairs in length.

In other embodiments, the single-stranded loop is 4, 5, 6, 7, 8, 9, 10, 11, 12, 13, or 14 nucleotides in length.

In certain embodiments, the single-stranded polynucleotide comprises an overhang on the 3'-end and/or an overhang on the 5'-end.

In certain embodiments, the 3'-stem sequence is 100% complementary to the 5'-stem sequence. In other embodiments, the 3'-stem sequence is less than 100% complementary to the 5'-stem sequence.

In certain embodiments, the 3'-stem sequence of the double-stranded stem comprises one or more universal base-pairing nucleotides.

In yet another embodiments, the RNAi constructs of the present invention comprise a double-stranded (dsRNA) construct of 25 base pairs in length, wherein the dsRNA comprises (1) a sense strand having a 5'-end and a 3'-end wherein said sense strand corresponds to a target sequence of an mRNA of the PCSK9 gene, and (2) a guide sequence having a 5'-end and a 3'-end that hybridizes to the sense strand or to the target sequence selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53-79, 94, 96, 98 and 100. In some embodiments, the target sequence is selected from the group consisting of SEQ ID NOs: 11, 19, 23, 25, 53, 55, 57, 59, 61, 63, 65, 66, 67, 69, 94, 96, 98 and 100 under physiological condition of a cell or under high stringency hybridization condition.

In certain embodiments, the dsRNA is blunt-ended.

In certain embodiments, the sense strand comprises one or more consecutive 2'-modified ribose sugar at east of said 5'- and 3'-ends of said sense strand. For example, in one aspect, the sense strand comprises 12 and 10 consecutive 2'-modified ribose sugars at the 5'-end and the 3'-end nucleotides, respectively. In another aspect, the sense strand comprises 4 consecutive 2'-modified ribose sugars at both ends.

In certain embodiments, the 2'-modified ribose sugars are 2'-O-alkyl nucleotides, 2'-deoxy-2'-fluoro nucleotides, 2'-deoxy nucleotides, 2'-H (deoxyribonucleotides), or combination thereof.

In certain embodiments, the guide sequence of the dsRNA further comprises a 2'-modified ribose sugar. For example, the 2'-ribose sugar is 2'-O-alkyl nucleotides, 2'-deoxy-2'-fluoro nucleotides, 2'-deoxy nucleotides, 2'-H (deoxyribonucleotides), or combination thereof.

In certain embodiments, the guide sequence of the dsRNA comprises a 2'-modification at the $2^{nd}$ nucleotide from the 5'-end of the guide sequence.

In certain embodiments, the guide sequence comprises four consecutive 2'-modification at the 3'-most end.

In certain embodiments, the PCSK9 gene is present in a cell. In a related embodiment, the PCSK9 gene is an endogenous gene.

In certain embodiments, the cell is of eukaryotic origin. For example, the cell is from a mammal, nematode, or insect.

In certain embodiments, the PCSK9 gene is human or mouse.

In certain embodiments, the target sequence of the present invention is at least 95% identical between the mouse and human sequences.

In certain embodiments, the constructs of the present invention reduce the PCSK9 mRNA level by at least 60% of normal level.

In certain embodiments, the constructs of the present invention exhibit low off-target effects. For example, the construct exhibits a seed region frequence of less than 6000, preferably less than 350.

In certain embodiments, the construct of the present invention associates with RISC.

In another aspect, the invention provides a vector expressing the RNAi constructs of the present invention. In another aspect, the invention provides a cell comprising the vector expressing the RNAi constructs of the present invention. In another aspect, the invention provides a cell comprising any of the RNAi constructs of the present invention.

In certain embodiments, the cell is a mammalian cell in culture. For example, the cell is a human cell.

The present invention also provides a composition comprising any of the RNAi construct described herein and a pharmaceutically acceptable carrier or diluent.

Also provided is a method for inhibiting the expression of a PCSK9 gene in a mammalian cell, comprising contacting the mammalian cell with an RNAi construct according to the invention, or a vector that expresses an RNAi construct as described herein.

In a related embodiment, the mammalian cell is in culture. For example, the mammalian cell is a human cell.

In certain embodiments, the mammalian cell is contacted in the presence of a delivery agent. For example, the delivery reagent comprises a lipid. In one aspect, the lipid is a cationic lipid. In another embodiment, the delivery reagent is a liposome. In other aspects, the delivery reagent comprises beta-glucan, chitosan, and/or PEI.

In one aspect, the invention provides a method of treating a patient for a disease characterized by overexpression of a PCSK9 gene, comprising administering to the patient an RNAi construct according to the present invention, wherein the RNAi construct mediates guide sequence-dependent reduction in PCSK9 expression.

In another aspect, the invention also provides a method of inhibiting expression of a PCSK9 gene with an RNAi construct according to the present invention, wherein the RNAi construct mediates guide sequence-dependent reduction in PCSK9 expression.

It is contemplated that any embodiment of the invention described herein can be combined with any one or more other embodiments whenever applicable, even though the different embodiments are separately described in different sections or aspects of the invention.

DETAILED DESCRIPTION OF THE INVENTION

I. Overview

Figure 1:
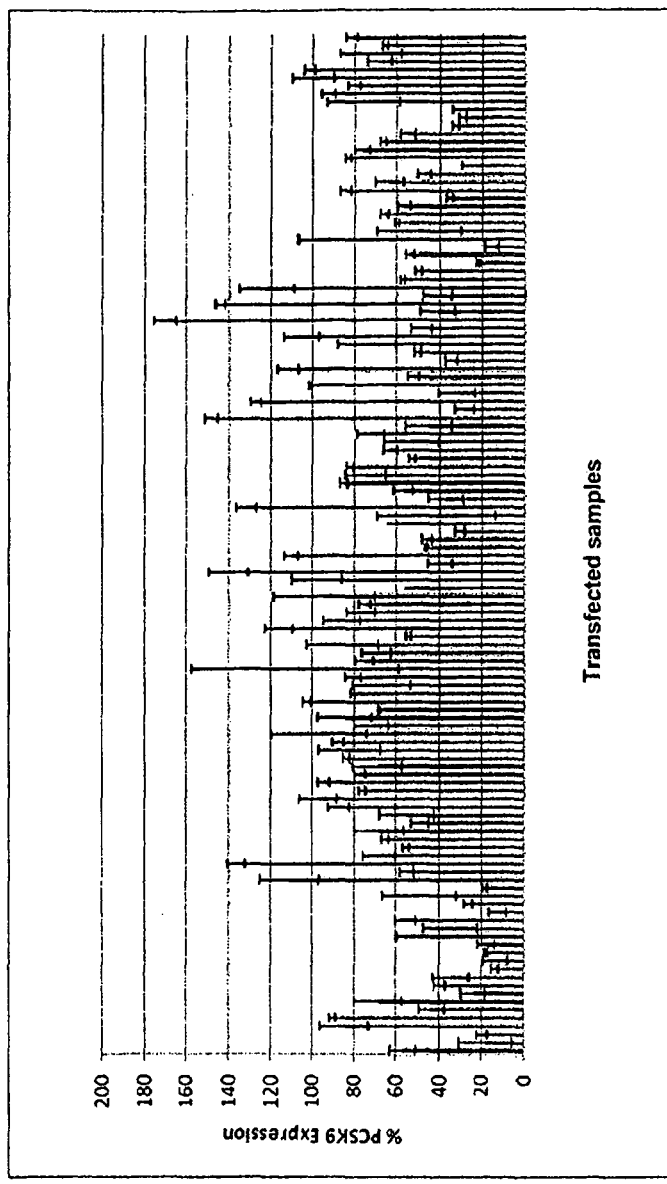
FIG. 1 shows an RNA screen across the length of the human PCSK9 gene (NM_174936; DNA: SEQ ID NO:80; Protein: SEQ ID NO:81). HeLaS3 cells were transfected at 0.1 nM active RNA concentration and target mRNA was measured 48 hours post-transfection. Four duplexes: duplex 1 (corresponding to SEQ ID NOs:11 and 12), duplex 2 (corresponding to SEQ ID NOs:19 and 20), duplex 3 (corresponding to SEQ ID NOs:23 and 24) and duplex 4 (corresponding to SEQ ID NOs:25 and 26), corresponding to start sites 944, 1035, 1086, and 1352, respectively, of human PCSK9 were chosen based on their activity and homology to the mouse PCSK9 gene (NM_153565.2; DNA: SEQ ID NO:82; Protein: SEQ ID NO:83).

The present invention is related, in part, to compositions and therapeutic methods for the regulation of PCSK9 activity. To this end, the invention is directed to methods of identifying agents and the use of identified agents for regulating PCSK9 in dysregulation, or in conditions that may benefit from silencing of PCSK9 to below physiological levels. In particular, described herein is PCSK9 silencing through the use of certain PCSK9 sequence-specific RNAi constructs which exhibit unexpectedly high gene silencing activity. The present invention also includes methods for identifying sequences within a PCSK9 gene that can be used to design effective RNAi constructs. RNAi constructs of the present method are designed and manipulated according to the methods described herein to yield highly stable and potent constructs with low levels of off-targeting effects.

In general, the invention is directed to RNAi constructs for inhibiting the expression of PCSK9, wherein said RNAi construct comprises a guide sequence that hybridizes to a target sequence on an mRNA of the PCSK9 gene and inhibits the expression of the PCSK9 gene through an RNAi interference mechanism, and wherein the target sequence is selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53-79, 94, 96, 98 and 100. In some embodiments, the target sequence is selected from the group consisting of SEQ ID NOs: 11, 19, 23, 25, 53, 55, 57, 59, 61, 63, 65, 66, 67, 69, 94, 96, 98 and 100. Described below are a few exemplary constructs that can be used in the context of the subject sequences and be used in the methods of the invention described herein. It is understood, however, that any given types of RNAi construct known in the art may be applicable. For example, in addition to the specific embodiments described herein (e.g., the double-stranded duplex and the "miniRNA" structures), the present invention relates to an RNAi construct that comprises a single-stranded polynucleotide that forms a hairpin structure, which includes a double-stranded stem and a single-stranded loop, wherein the double-stranded stem can be cleaved by Dicer to produce an siRNA having a guide sequence that hybridizes to a sequence selected from SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53-79, 94, 96, 98 and 100. In some embodiments, the target sequence is selected from the group consisting of SEQ ID NOs: 11, 19, 23, 25, 53, 55, 57, 59, 61, 63, 65, 66, 67, 69, 94, 96, 98 and 100. Further still, the present invention includes an siRNA (such as a duplex of 19 nucleotides, with or without 3'-overhangs), as described in the art, comprising a guide sequence that hybridizes to a sequence selected from SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53-79, 94, 96, 98 and 100. In some embodiments, the target sequence is selected from the group consisting of SEQ ID NOs: 11, 19, 23, 25, 53, 55, 57, 59, 61, 63, 65, 66, 67, 69, 94, 96, 98 and 100 under physiological condition of a cell or under high stringency hybridization condition.

Double-Stranded Duplex Structures

In one aspect, the invention provides a double-stranded RNA (dsRNA) construct, preferably of 25 base pairs in length, for inhibiting expression of a PCSK9 gene. Such dsRNA construct comprises a sense strand having a 5'-end and a 3'-end that corresponds to a region within an mRNA transcript of the PCSK9 gene, and an antisense strand having a 5'-end and a 3'-end that hybridizes to the sense strand under physiological conditions of a cell or under high stringency hybridization conditions. In certain embodiments, the sense strand comprises a sequence selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53-79, 94, 96, 98 and 100. In some embodiments, the target sequence is selected from the group consisting of SEQ ID NOs: 11, 19, 23, 25, 53, 55, 57, 59, 61, 63, 65, 66, 67, 69, 94, 96, 98 and 100. The dsRNA construct of the present invention inhibits expression of PCSK9 in a sequence-dependent manner.

In certain embodiments, the sense strand comprises one or more consecutive 2'-modified ribose sugar at each of said 5'- and 3'-ends of said sense strand. In certain preferred embodiments, the sense strand comprises 12 and 10 consecutive T-modified ribose sugar at each of said 5'-end and 3'-end nucleotides, respectively. In certain embodiments, each end of the sense strand comprises a continuous stretch of 2'-modified ribose sugars, although each end may have the same number or different numbers of 2'-modified ribose sugars. In other aspects, the sense strand comprises 4 consecutive 2'-modified ribose sugars at both ends.

For a 25-mer construct, each end of the sense strand may comprise, independently, 4-16 2'-modified nucleotides and/or non-hydrolyzable linkages (e.g., phosphothioate linkages). The number of the modified bases may be adjusted depending on the overall length of the construct. For example, for a 27-mer, each end of the sense strand may comprise, independently, 4-18 2'-modified nucleotides and/or phosphothioate linkages, etc.

In other embodiments, the antisense strand comprises an antisense sequence of a sense strand selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53-79, 94, 96, 98 and 100. In some embodiments, the target sequence is selected from the group consisting of SEQ ID NOs: 11, 19, 23, 25, 53, 55, 57, 59, 61, 63, 65, 66, 67, 69, 71, 94, 96, 98 and 100. For example, antisense sequences that recognize SEQ ID NOs:11, 19, 23 and 25 are shown in Table 1 as SEQ ID NOs:12, 20, 24 and 26 respectively.

In certain embodiments, the antisense strand is unmodified. In other aspects of the invention, the antisense (guide) strand further comprises a 2'-modified ribose sugar. Such 2'-modification of the antisense strand is at the $2^{nd}$ nucleotide from the 5' end of the antisense strand. In another embodiment, the antisense strand comprises four consecutive 2'-modification at the 3'-most end of the antisense strand.

sd-rxRNA$^{nano}$

RNA molecules associated with the invention can be sd ("self-delivering")-rxRNA$^{nano}$ molecules. Such molecules can also be referred to as "nano RNA" or "sd-rxRNA." As used herein, "sd-rxRNA$^{nano}$" molecules are asymmetric chemically modified nucleic acid molecules with double-stranded regions of minimal length such as 8-14 nucleotides. These and other RNAi molecules associated with the invention can contain a variety of chemical modifications on the sense and/or antisense strand and can also be attached to a hydrophobic conjugate such as conventional and advanced sterol-type molecules.

An sd-rxRNA$^{nano}$ molecule can in some aspects includes a guide strand with a minimal length of 16 nucleotides, and a passenger strand, forming a double stranded nucleic acid, having a double stranded region and a single stranded region, the double stranded region having 8-15 nucleotides in length, the single stranded region having 5-12 nucleotides in length, wherein the passenger strand is linked to a lipophilic group, wherein at least 40% of the nucleotides of the double stranded nucleic acid are modified, and wherein the single stranded region has at least 2 phosphorothioate modifications. Position 1 of the guide strand can be 5' phosphorylated and in some embodiments is also 2'O-methyl modified.

An sd-rxRNA$^{nano}$ molecule can in some aspects include a guide strand of 17-21 nucleotides in length that has complementarity to a target gene and a passenger strand of 8-16 nucleotides in length linked at the 3' end to a lipophilic group. The guide strand can have a 3' single stranded region of 2-13 nucleotides in length, wherein one or more nucleotides within the single stranded region has phosphorothioate modifications. The guide strand of such molecules can also be 5' phosphate modified and can contain at least one 2' O-methyl modification or 2'-fluoro modification of one or more C and/or U nucleotides in the double stranded region. The passenger (sense) strand can also contain modifications such as the addition of methyl groups.

Further description of sd-rxRNA$^{nano}$ molecules is incorporated by reference from U.S. Provisional Application No. 61/192,954, entitled "Chemically Modified Polyucleotides and Methods of Using the Same," filed on Sep. 22, 2008, U.S. Provisional Application No. 61/149,946, entitled "Minimum Length Triggers of RNA Interference," filed on Feb. 4, 2009, U.S. Provisional Application No. 61/224,031, entitled "Minimum Length Triggers of RNA Interference," filed on Jul. 8, 2009, and PCT Application No. PCT/US2009/005247, entitled "Reduced Size Self-Delivering RNAi Compounds," filed on Sep. 22, 2009, the disclosure of each of which is incorporated by reference herein in its entirety.

As used herein, "2'-modified ribose sugar" includes those ribose sugars that do not have a 2'-OH group. For example, the 2'-modified ribose sugar may be 2'-O-alkyl nucleotides, 2'-deoxy-2'-fluoro nucleotides, 2'-deoxy nucleotides, 2'-H (deoxyribonucleotides), or combination thereof. In certain embodiments, the 2'-modified nucleotides are pyrimidine nucleotides (e.g., C/U). The 2'-O-alkyl nucleotides may be, for example, 2'-O-methyl nucleotides, or 2'-O-allyl nucleotides.

In another embodiment, dsRNA constructs of the present invention comprise PCSK9 sequences of human or mouse origin. Additionally, in certain preferred embodiments, the sense strands of the dsRNA correspond to regions of the PCSK9 mRNA sequence that is at least about 80%, 85%, 90%, 95%, 97%, or 99% identical between the mouse and human sequences.

In other aspects of the invention, the dsRNA construct significantly (e.g., at least about 40%, 45%, 50%, 55%, 60%, 65%, 70%, 75%, 80%, 85%, 90%, 95% or more) reduces a PCSK9 mRNA level relative to normal (physiological) or physiologically aberrant (e.g., overexpression) levels. In preferred aspects of the invention, the dsRNA construct reduces a PCSK9 mRNA level by at least 60% of a normal level.

In certain embodiments, the dsRNA of the invention with the above-referenced modifications exhibits significantly (e.g., at least about 25%, 30%, 35%, 40%, 45%, 50%, 55%, 60%, 65%, 70%, 75%, 80%, 85%, 90% or more) less "off-target" gene silencing when compared to similar constructs without the specified antisense modification, thus greatly improving the overall specificity of the RNAi reagent or therapeutics.

As used herein, "off-target" gene silencing refers to unintended gene silencing due to, for example, spurious sequence homology between the antisense (guide) sequence and the unintended target mRNA sequence.

In certain embodiments, a suitable dsRNA PCSK9 sequence to be used as an siRNA construct in the present invention adheres to what has been described as having a low or moderate seed complement frequency (SCF). See, for example, Anderson et al. (RNA, 2008, 14: 853-861). SCF refers to the pairing between the hexamer seed region of an siRNA antisense strand (nucleotides 2-7) and complementary sequences in the 3' UTR of mature transcripts. This association has been implicated as a contributing factor in off-targeting effects. As defined herein, siRNA sequences with low (<350) or moderate (~350-6000) incidents of complementation with the 3' UTR (i.e., low or moderate SCF) exhibit less off-targeting effects. Accordingly, in certain preferred embodiments, the subject PCSK9-specific RNAi agents have low to moderate SCF. It should also be understood, however, that while low or moderate SCF is desirable, it is not essential for reduced off-targeting effects. As such, in certain embodiments, a sequence may fall within the range of high SCF (>6000) and still exhibits low off-targeting effects.

According to this aspect of the invention, certain sense or antisense modifications further increase nuclease stability, and/or lower interferon induction, without a significant decrease in RNAi activity (or no decrease in RNAi activity at all).

In certain embodiment of the invention, the dsRNA construct associates with an RNA-induced silencing complex (RISC).

In another embodiment, the dsRNA construct of the present invention is blunt-ended. In other embodiments, 5'- and/or 3'-end overhangs of 1-4 nucleotides may be present on one or both strands.

In further aspects, the present invention contemplates a composition comprising the dsRNA described herein and a pharmaceutically acceptable carrier or diluent.

Another aspect of the invention provides a method for inhibiting the expression of a PCSK9 gene in a mammalian cell, comprising contacting the mammalian cell with any of the subject dsRNA constructs. Another aspect of the invention provides a method for inhibiting the expression of a PCSK9 gene in a mammalian cell, comprising contacting the mammalian cell with a vector expressing at least one strand of any of the subject dsRNA constructs. The method may be carried out in vitro or in vivo, in, for example, mammalian cells in culture, such as a human cell in culture. The target cells (e.g., mammalian cell) may be contacted in the presence of a delivery reagent, such as a lipid (e.g., a cationic lipid), a liposome, beta-glucan, chitosan, polyethyleneimine (PEI), or any combination thereof.

Another aspect of the invention provides a method for inhibiting the expression of a target gene in a mammalian cell, comprising contacting the mammalian cell with a vector expressing at least one strand of the dsRNA according to the present methods.

It is contemplated that different features of the invention, such as the different sense and/or antisense strand modifications, may be combined except when indicated otherwise, in order to create RNAi constructs with multiple advantages or features over the conventional siRNA constructs. Furthermore, it is also contemplated that any of the modifications to the dsRNA as described in U.S. Provisional Application 61/065,335, filed on Feb. 11, 2008, entitled "MODIFIED RNAI POLYNUCLEOTIDES AND USES THEREOF", incorporated herein by reference in its entirety, may be applied to the present compositions and methods.

For example, for all applicable aspects of the invention, the antisense strand may comprise a 2'-modified ribose sugar, such as 2'-O-methyl modified nucleotide, at the 2nd nucleotide on the 5'-end of the antisense strand and, preferably no other modified nucleotides. The dsRNA having such modification may have enhanced target specificity or reduced off-target silencing compared to a similar construct without the 2'-O-methyl modification at said position.

For all applicable aspects of the invention, the antisense strand may comprise at least four consecutive 2'-modified ribose sugars, such as 2'-O-methyl modified, 3'-end nucleotides with non-hydrolyzable internucleotide linkages, such as phosphothioate linkages.

For all applicable aspects of the invention, the 5'-end 12 nucleotides and the 3'-end 10 nucleotides of a 25-mer may be 2'-modified ribose sugars. The number of the modified bases may be adjusted depending on the overall length of the construct. For example, for a 27-mer, the 5'-end 12-14 nucleotides and the 3'-end 10-12 nucleotides may be 2'-modified nucleotides, etc.

For all applicable aspects of the invention, the dsRNA may comprise a mismatch nucleotide at the $2^{nd}$ nucleotide from the 3'-end of the sense strand.

Certain combinations of specific antisense and sense strand modifications may even result in unexpected advantages, as partly manifested by enhanced ability to inhibit target gene expression, enhanced serum stability, and/or increased target specificity, etc.

According to this embodiment of the invention, certain sense strand sequences may be cleaved by the RISC complex loaded with the Dicer-resistant guide sequence, at the position where an equivalent mRNA is cleaved. While not wishing to be bound by any particular theory, this is partly because the sense strand share the same or similar sequence as the target mRNA. Therefore, the subject dsRNA constructs include those with a sense strand that can be cleaved between the 10th and 11th 3'-end nucleotides.

In alternative embodiments, the constructs of the invention may have different lengths. In certain embodiments, the preferred lengths of the construct are 19-49 nucleotides in length. In certain embodiments, the length of the construct is greater than or equal to 22 nucleotides in length. In certain embodiments, the length of the construct is greater than or equal to 25 nucleotides in length. In certain embodiments, the length of the construct is 26, 27, 28, 29, 30, or 31-49 nucleotides in length. Other lengths are also possible, so long as the lower length limit is the minimal length for a Dicer substrate, and the upper limit is a length that generally will not trigger PKR response in a target cell. In certain embodiments, modifications may alter that upper limit such that longer lengths (such as 50, 60, 70, 80, 90, 100 bp) are tolerable.

In certain embodiments, the modified dsRNA may have improved stability in serum and/or cerebral spinal fluid compared to an unmodified dsRNA having the same sequence.

In certain embodiments, the dsRNA does not induce interferon response in primary cells, such as mammalian primary cells, including primary cells from human, mouse and other rodents, and other non-human mammals.

In certain embodiments, the dsRNA may also be used to inhibit expression of a target gene in an invertebrate organism.

To further increase the stability of the subject constructs in vivo, either end of the sense strand and/or the 3'-end of the antisense strand may be blocked by protective group(s). For example, protective groups such as inverted nucleotides, inverted abasic moieties, or amino-end modified nucleotides may be used. Inverted nucleotides may comprise an inverted deoxynucleotide. Inverted abasic moieties may comprise an inverted deoxyabasic moiety, such as a 3',3'-linked or 5',5'-linked deoxyabasic moiety.

In certain embodiments, alternating nucleotides on the ends of the sense and/or antisense strands comprise 2'-modified ribose sugars, and wherein each of the 2'-modified ribose sugars faces an unmodified nucleotide on the opposite strand. In certain embodiment, the first 2'-modified antisense nucleotide is the most 5'-end antisense nucleotide or the 2nd nucleotide from the 5'-end of the antisense strand.

In certain embodiments, the subject double-stranded RNA may be chemically cross-linked at one or more points, or linked by a nucleotide loop structure at one or both ends (e.g., a single-stranded hairpin structure or a circular structure). In one embodiment, the chemical cross-link or the loop of the hairpin structure is at the 3'-end of the antisense strand (e.g., linking the 3'-end of the antisense strand to the 5'-end of the sense strand). In another embodiment, the chemical cross-link or the loop of the hairpin structure is at the 5'-end of the antisense strand (e.g., linking the 3'-end of the sense strand to the 5'-end of the antisense strand. In these embodiments, other structural features of the cross-linked or looped constructs, such as 5'-end and 3'-end modifications on the sense strand and/or the other modifications on the antisense strand, are essentially the same as those for the dsRNA described herein.

Another aspect of the invention provides a method for improving the gene silencing effect of a small interference RNA (siRNA), comprising modifying the sense and/or antisense nucleotides of the siRNA to become any of the subject dsRNA constructs.

Single-Stranded Hairpin Structures

In another embodiment of the invention, the subject PCSK9 sequences are incorporated in the context of a hairpin structure. It has been previously described that a hairpin structure formed from a single-stranded polynucleotide does not require processing, and indeed is not processed by Dicer or other Dicer-like Rnase III enzymes to participate in (RISC-mediated) RNA interference. See U.S. Provisional Application No. 61/135,855, filed Jul. 24, 2008, entitled "SHORT HAIRPIN RNAi CONSTRUCTS AND USES THEREOF," U.S. Provisional Application No. 61/197,768, filed on Oct. 30, 2008, entitled "miniRNA CONSTRUCTS AND USES THEREOF", U.S. Provisional Application No. 61/208,394, filed on Feb. 23, 2009, entitled "RNAI CONTRUCTS AND USES THEREOF," U.S. Provisional Application No. 61/209,429, filed on Mar. 6, 2009, entitled "RNAI CONSTRUCTS AND USES THEREOF," and PCT Application PCT/US2009/004326, filed on Jul. 23, 2009, entitled "RNAI CONSTRUCTS AND USES THEREOF," incorporated herein by reference in their entire contents. The guide strand of such a hairpin structure becomes the single species of active RNAi reagent, and thus facilitates the development of RNAi reagents or therapeutics with higher target specificity, and better-defined biologicial activity and/or pharmacological property.

Another advantages of the miniRNA is the presence of single-stranded region (loop region). In some cases, single-stranded polynucleotides are a better substrates for cellular uptake. Furthermore, in some embodiments, the single-stranded (loop) region is chemically modified. For example, in some embodiments, the chemical modification may comprise phosphothioate. In some other embodiments, the chemical modification comprises 2'OME or 2' Fluoro or 2' deoxy. In yet other embodiments, the chemical modification is a combination of phosphothioates with 2' OMe and 2' Fluoro. In other embodiments, the loop may be completely or partially replaced by a chemical linker that is flexible enough to allow folding back of the duplex polynucleotide.

Thus in another aspect, the invention provides a single-stranded polynucleotide miniRNA construct of 15-49 nucleotides in length, for inhibiting expression of a PCSK9 gene, said polynucleotide comprising: (1) a 5'-stem sequence having a 5'-end, and (2) a 3'-stem sequence having a 3'-end, said 5'-stem sequence and 3'-stem sequence being sufficiently complementary to form a double-stranded stem, and (3) a single-stranded loop bridging the 5'-stem and 3'-stem sequences. The single-stranded loop may be 2-15 nucleotides in length, or preferably 4, 5, 6, 7, 8, 9, 10, or 11 nucleotides in length. The 5'-stem sequence (including any 5'-end overhangs) and at least a portion or all of said single-stranded loop form a guide strand/sequence that is complementary to a transcript of a target gene. Furthermore, the single-stranded polynucleotide miniRNA structure may be (1) resistant to cleavage by Dicer, (2) associates with RISC, and/or (c) inhibits expression of the target gene in a guide sequence-dependent manner.

In another aspect, the invention provides a single-stranded polynucleotide miniRNA construct of 15-49 nucleotides in length, for inhibiting expression of a PCSK9 gene, said polynucleotide comprising: (1) a 5'-stem sequence having a 5'-end, and (2) a 3'-stem sequence having a 3'-end, said 5'-stem sequence and 3'-stem sequence being sufficiently complementary to form a double-stranded stem, and (3) a single-stranded loop bridging the 5'-stem and 3'-stem sequences. The single-stranded loop may be 2-15 nucleotides in length, or preferably 4, 5, 6, 7, 8, 9, 10, 11, 12, 13, or 14 nucleotides in length, or more preferably 4, 5, 6, 7 nucleotides in length. In certain embodiments, the single-stranded loop is 4 or 6 nucleotides in length. In unmodified forms, the preferred length of the miniRNA stem region is around 10-13 bp. In certain embodiments, the double-stranded stem region is at least 11 bp in length, preferably at least 12 bp in length.

In certain embodiments, the guide sequence hybridizes to a target sequence on an mRNA of the PCSK9 gene, wherein the target sequence is selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53-79, 94, 96, 98 and 100. In some embodiments, the target sequence is selected from the group consisting of SEQ ID NOs: 11, 19, 23, 25, 53, 55, 57, 59, 61, 63, 65, 66, 67, 69, 94, 96, 98 and 100.

While not wishing to be bound by any particular theory, it is believed that the duplex/stem length limitation may be partially defined by thermodynamic stability in cellular environments. Thus a group of chemical modifications known to enhance thermodynamic stability of a duplex region may be used to alter stem length. A non-limiting example of these chemical modifications might be LNA (locked nucleic acid) or MGB (minor groove binder). There are other chemical modifications with similar properties in the art. One or more stabilizing chemical modifications might be applied to the duplex region of short miniRNAs and convert otherwise non-functional entities to functional ones. Preferably, the modification is in a non-guide sequence region.

Since chemically modified miniRNA stem length can be as small as 6 base pairs, standard bioinformatics methods may be used to identify perfect or partially perfect inverted repeats (IR) regions and use them as additional PCSK9 target sites for miniRNAs, further to the target PCSK9 sequences identified in the present invention.

The 5'-stem sequence (including any 5'-end overhangs), the single-stranded loop, and at least a portion or all of the 3'-stem sequence form a guide strand/sequence that is complementary to a transcript of a PCSK9 gene. Furthermore, the single-stranded polynucleotide miniRNA structure may be (1) resistant to cleavage by Dicer, (2) associates with RISC, and/or (c) inhibits expression of the PCSK9 gene in a guide sequence-dependent manner.

In certain embodiments, the polynucleotide does not contain any overhangs. In other embodiments, 5'- and/or 3'-end overhangs of 1-6 nucleotides (preferably 1, 2, or 3 nucleotide overhang) may be present on one or both ends of the polynucleotide. The number and/or sequence of nucleotides overhang on one end of the polynucleotide may be the same or different from the other end of the polynucleotide. In certain embodiments, one or more of the overhang nucleotides may contain chemical modification(s), such as phosphothiate or 2'-OMe modification.

In certain embodiments, the polynucleotide is unmodified. In other embodiments, at least one nucleotide is modified. In further embodiments, the modification includes a 2'-H or 2'-modified ribose sugar at the $2^{nd}$ nucleotide from the 5'-end of the guide sequence. The "2nd nucleotide" is defined as the second nucleotide from the 5'-end of the polynucleotide.

As used herein, "2'-modified ribose sugar" includes those ribose sugars that do not have a 2'-OH group. "2'-modified ribose sugar" does not include 2'-deoxyribose (found in unmodified canonical DNA nucleotides). For example, the 2'-modified ribose sugar may be 2'-O-alkyl nucleotides, 2'-deoxy-2'-fluoro nucleotides, 2'-deoxy nucleotides, or combination thereof.

In certain embodiments, the 2'-modified nucleotides are pyrimidine nucleotides (e.g., C/U). Examples of 2'-O-alkyl nucleotides include 2'-O-methyl nucleotides, or 2'-O-allyl nucleotides.

In certain embodiments, the miniRNA polynucleotide of the invention with the above-referenced 5'-end modification exhibits significantly (e.g., at least about 25%, 30%, 35%, 40%, 45%, 50%, 55%, 60%, 65%, 70%, 75%, 80%, 85%, 90% or more) less "off-target" gene silencing when compared to similar constructs without the specified 5'-end modification, thus greatly improving the overall specificity of the RNAi reagent or therapeutics.

According to this aspect of the invention, certain guide strand modifications further increase nuclease stability, and/or lower interferon induction, without significantly decreasing RNAi activity (or no decrease in RNAi activity at all).

For example, for all applicable aspects of the invention, the 5'-stem sequence may comprise a 2'-modified ribose sugar, such as 2'-O-methyl modified nucleotide, at the $2^{nd}$ nucleotide on the 5'-end of the polynucleotide and, preferably no other modified nucleotides. The hairpin structure having such modification may have enhanced target specificity or reduced off-target silencing compared to a similar construct without the 2'-O-methyl modification at said position.

Certain combinations of specific 5'-stem sequence and 3'-stem sequence modifications may result in further unexpected advantages, as partly manifested by enhanced ability to inhibit target gene expression, enhanced serum stability, and/or increased target specificity, etc.

The constructs of the invention may have different lengths. In certain embodiments, the preferred lengths of the miniRNA construct are 15-49 nucleotides in length. In certain embodiments, the length of the miniRNA construct is 25 or 26 nucleotides in length. Other lengths are also possible, so long as the double-stranded stem does not exceed a maximum length causing it to be a Dicer substrate. In certain preferred aspects, the maximum length of the double-stranded stem does not exceed 21 base pairs. In another aspect, the maximum length of the double-stranded stem does not exceed 19 base pairs. Additionally, the double-stranded stem may be shorter than 10 base pairs without negatively affecting the RNAi capability of the hairpin construct. In other embodiments, the length of the single-stranded loop may be varied to allow for enhanced stability, for example.

In certain embodiments, the guide strand comprises a 2'-O-methyl modified nucleotide at the $2^{nd}$ nucleotide on the 5'-end of the guide strand and no other modified nucleotides.

In certain embodiments, the modified hairpin structure may have improved stability in serum and/or cerebral spinal fluid compared to an unmodified hairpin structures having the same sequence.

In other embodiments, at least the first 10 nucleotides from the 5'-end of the polynucleotide are 100% complementary to the PCSK9 gene transcript. More preferably, at least the first 12 nucleotides from the 5'-end of the polynucleotide are 100% complementary to the PCSK9 gene transcript. In certain preferred embodiments, about the first 12 to 15 nucleotides from the 5'-end of the polynucleotide are 100% complementary to the PCSK9 gene transcript.

In certain embodiments, only nucleotides 2 to 17 of the guide sequence/strand is complementary to the PCSK9 sequence. The sequence complementarity may be partial, preferably, the guide sequence can hybridize to the PCSK9 sequence under the physiological condition of the cell or under high stringency condition.

As described herein, a nucleic acid molecule is "hybridizable" to another nucleic acid molecule, such as a cDNA, genomic DNA, or RNA, when a single-stranded form of the nucleic acid molecule can anneal to the other micleic acid molecule under the appropriate conditions of temperature and solution ionic strength (see Sambrook et al. *Molecular Cloning: A Laboratory Manual*, Second Edition (1989) Cold Spring Harbor Laboratory Press, Cold Spring Harbor, N.Y.). The conditions of temperature and ionic strength determine the "stringency" of the hybridization. Low stringency hybridization conditions correspond to a $T_m$ (melting temperature) of 55° C., e.g., 5×SSC, 0.1% SDS, 0.25% milk, and no formamide; or 30% formamide, 5×SSC, 0.5% SDS. Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC. SSC is 0.15 M NaCl, 0.015 M Na-citrate.

"High stringency conditions" are understood to encompass conditions of hybridization which allow hybridization of structurally related, but not structurally dissimilar, nucleic acids. The term "stringent" is a term of art which is understood by the skilled artisan to describe any of a number of alternative hybridization and wash conditions which allow annealing of only highly complementary nucleic acids.

Exemplary high stringent hybridization conditions is equivalent to about 20-27° C. below the melting temperature ($T_m$) of the DNA duplex formed in about 1 M salt. Many equivalent procedures exist and several popular molecular cloning manuals describe suitable conditions for stringent hybridization and, furthermore, provide formulas for calculating the length of hybrids expected to be stable under these conditions (see e.g. *Current Protocols in Molecular Biology*, John Wiley & Sons, N.Y. (1989), 6.3.1-6 or 13.3.6; or pages 9.47-9.57 of Sambrook, et al. (1989) *Molecular Cloning*, $2^{nd}$ ed., Cold Spring Harbor Press).

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.51). For hybridization with shorter nucleic acids, i.e., oligonucleotides, the position of mismatches becomes more important, and the length of the oligonucleotide determines its specificity (see Sambrook et al., supra, 11.8). A minimum length for a hybridizable nucleic acid is at least about 10 nucleotides; preferably at least about 15 nucleotides; and more preferably the length is at least about 20 nucleotides.

Unless specified, the term "standard hybridization conditions" or "physiological conditions" refers to a $T_m$ of about 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2×SSC, at 42° C. in 50% formamide, 4×SSC, or under conditions that afford levels of hybridization equivalent to those observed under either of these two conditions.

Suitable hybridization conditions for oligonucleotides (e.g., for oligonucleotide probes or primers) are typically somewhat different than for full-length nucleic acids (e.g., full-length cDNA), because of the oligonucleotides' lower melting temperature. Because the melting temperature of oligonucleotides will depend on the length of the oligonucleotide sequences involved, suitable hybridization temperatures will vary depending upon the oligonucleotide molecules used. Exemplary temperatures may be 37° C. (for 14-base oligonucleotides), 48° C. (for 17-base oligonucleotides), 55° C. (for 20-base oligonucleotides) and 60° C. (for 23-base oligonucleotides). Exemplary suitable hybridization conditions for oligonucleotides include washing in 6×SSC, 0.05% sodium pyrophosphate, or other conditions that afford equivalent levels of hybridization.

In certain embodiments, the hairpin structure does not induce interferon response in primary cells, such as mammalian primary cells, including primary cells from human, mouse and other rodents, and other non-human mammals. In certain embodiments, the hairpin structure may also be used to inhibit expression of a PCSK9 gene in an invertebrate organism.

To further increase the stability of the subject constructs in vivo, the 3'-end of the hairpin structure may be blocked by protective group(s). For example, protective groups such as inverted nucleotides, inverted abasic moieties, or amino-end modified nucleotides may be used. Inverted nucleotides may comprise an inverted deoxynucleotide. Inverted abasic moieties may comprise an inverted deoxyabasic moiety, such as a 3',3'-linked or 5',5'-linked deoxyabasic moiety.

The invention includes methods to inhibit expression of a PCSK9 gene either in a cell in vitro, or in vivo. As such, the polynucleotide hairpin constructs of the invention are useful for treating a patient with a disease characterized by the overexpression of a PCSK9 gene. In other embodiments, the polynucleotide hairpin constructs of the invention are useful for treating a condition that would benefit from inhibition of a PCSK9 gene below physiological levels.

The PCSK9 gene can be endogenous or exogenous (e.g., introduced into a cell by a virus or using recombinant DNA technology) to a cell. Such methods may include introduction of RNA into a cell in an amount sufficient to inhibit expression of the PCSK9 gene, where the RNA is a hairpin structure. By way of example, such an RNA molecule may have a guide strand that is complementary to the nucleotide sequence of the PCSK9 gene, such that the composition inhibits expression of the PCSK9 gene. As described in the foregoing embodiments, the guide strand may be formed by the 5'-stem sequence (including any 5'-end overhangs) and all or a portion of the single-stranded loop region. Alternatively, the guide strand may be formed by the 5'-stem sequence (including any 5'-end overhangs), the entire loop region, and all or a portion of the 3'-stem sequence.

The invention also relates to vectors expressing the subject hairpin constructs, and cells comprising such vectors or the subject hairpin constructs. The cell may be a mammalian cell in vivo or in culture, such as a human cell.

The invention further relates to compositions comprising the subject hairpin constructs, and a pharmaceutically acceptable carrier or diluent.

Another aspect of the invention provides a method for inhibiting the expression of a target gene in a mammalian cell, comprising contacting the mammalian cell with any of the subject hairpin constructs.

The method may be carried out in vitro, ex vivo, or in vivo, in, for example, mammalian cells in culture, such as a human cell in culture.

The target cells (e.g., mammalian cell) may be contacted in the presence of a delivery reagent, such as a lipid (e.g., a cationic lipid) or a liposome.

Another aspect of the invention provides a method for inhibiting the expression of a PCSK9 gene in a mammalian cell, comprising contacting the mammalian cell with a vector expressing the subject hairpin constructs.

Generally, in certain aspects, the RNAi structures of the present invention mediate sequence-dependent gene silencing by a microRNA mechanism. As used herein, the term "microRNA" ("miRNA"), also referred to in the art as "small temporal RNAs" ("stRNAs"), refers to a small (10-50 nucleotide) RNA which are genetically encoded (e.g., by viral, mammalian, or plant genomes) and are capable of directing or mediating RNA silencing. An "miRNA disorder" shall refer to a disease or disorder characterized by an aberrant expression or activity of an miRNA.

microRNAs are involved in down-regulating target genes in critical pathways, such as development and cancer, in mice, worms and mammals. Gene silencing through a microRNA mechanism is achieved by specific yet imperfect base-pairing of the miRNA and its target messenger RNA (mRNA). Various mechanisms may be used in microRNA-mediated down-regulation of target mRNA expression.

miRNAs are noncoding RNAs of approximately 22 nucleotides which can regulate gene expression at the post transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof. Naturally-occurring miRNAs are expressed by endogenous genes in vivo and are processed from a hairpin or stem-loop precursor (pre-miRNA or pri-miRNAs) by Dicer or other RNAses. miRNAs can exist transiently in vivo as a double-stranded duplex but only one strand is taken up by the RISC complex to direct gene silencing.

Another pathway that uses small RNAs as sequence-specific regulators is the RNA interference (RNAi) pathway, which is an evolutionarily conserved response to the presence of double-stranded RNA (dsRNA) in the cell. The dsRNAs are cleaved into ~20-base pair (bp) duplexes of small-interfering RNAs (siRNAs) by Dicer. These small RNAs get assembled into multiprotein effector complexes called RNA-induced silencing complexes (RISCs). The siRNAs then guide the cleavage of target mRNAs with perfect complementarity.

Some aspects of biogenesis, protein complexes, and function are shared between the siRNA pathway and the miRNA pathway. The subject RNAi constructs may mimic the dsRNA in the siRNA mechanism, or the microRNA in the miRNA mechanism.

As described herein, a PCSK9 gene or protein includes the full-length version as well as any naturally occurring fragments thereof. Additionally, a PCSK9 gene or protein includes any naturally occurring isoforms of PCSK9.

More detailed aspects of the invention are described in the sections below.

II. Duplex Structure

Duplex Characteristics

Double-stranded oligonucleotides of the invention may be formed by two separate complementary nucleic acid strands. Duplex formation can occur either inside or outside the cell containing the target gene.

As used herein, the term "double-stranded" includes one or more nucleic acid molecules comprising a region of the molecule in which at least a portion of the nucleomonomers are complementary and hydrogen bond to form a duplex.

As used herein, the term "duplex" includes the region of the double-stranded nucleic acid molecule(s) that is (are) hydrogen bonded to a complementary sequence. Double-stranded oligonucleotides of the invention may comprise a nucleotide sequence that is sense to a target gene and a, complementary sequence that is antisense to the target gene. The sense and antisense nucleotide sequences correspond to the target gene sequence, e.g., are identical or are sufficiently identical to effect target gene inhibition (e.g., are about at least about 98% identical, 96% identical, 94%, 90% identical, 85% identical, or 80% identical) to the target gene sequence.

In certain embodiments, the double-stranded oligonucleotide of the invention is double-stranded over its entire length, i.e., with no overhanging single-stranded sequence at either end of the molecule, i.e., is blunt-ended. In other embodiments, the individual nucleic acid molecules can be of different lengths. In other words, a double-stranded oligonucleotide of the invention is not double-stranded over its entire length. For instance, when two separate nucleic acid molecules are used, one of the molecules, e.g., the first molecule comprising an antisense sequence, can be longer than the second molecule hybridizing thereto (leaving a portion of the molecule single-stranded). Likewise, when a single nucleic acid molecule is used a portion of the molecule at either end can remain single-stranded.

In one embodiment, a double-stranded oligonucleotide of the invention contains mismatches and/or loops or bulges, but is double-stranded over at least about 70% of the length of the oligonucleotide. In another embodiment, a double-stranded oligonucleotide of the invention is double-stranded over at least about 80% of the length of the oligonucleotide. In another embodiment, a double-stranded oligonucleotide of the invention is double-stranded over at least about 90%-95% of the length of the oligonucleotide. In another embodiment, a double-stranded oligonucleotide of the invention is double-stranded over at least about 96%-98% of the length of the oligonucleotide. In certain embodiments, the double-stranded oligonucleotide of the invention contains at least or up to 1, 2, 3, 4, 5, 6, 7, 8, 9, 10, 11, 12, 13, 14, or 15 mismatches.

Hairpin Characteristics

In a first embodiment, the hairpin structures of the present invention include a nucleic acid comprising a single-stranded RNA, such as a shRNA. The hairpin structure can include a double-stranded stem region formed from a 5'-stem sequence having a 5'-end ("5'-stem sequence") and a 3'-stem sequence having a 3'-end ("3'-stem sequence") that is complementary to the 5'-stem sequence. The hairpin structure can further include a single-stranded loop region. In a related embodiment, the single-stranded polynucleotide is a DNA strand comprising one or more modified deoxyribonucleotides. In yet another related embodiment, the single-stranded polynucleotide is an XNA strand, such as a peptide nucleic acid (PNA) strand or locked nucleic acid (LNA) strand. Further still, the single-stranded polynucleotide is a DNA/RNA hybrid.

Preferably the 5'-stem sequence and 3'-stem sequence are at least substantially complementary to each other, and more preferably about 100% complementary to each other. More preferably, the 5'-stem sequence and 3'-stem sequence are each 5 to 19 nucleotides, inclusive, in length. Alternatively, the 5'-stem sequence and 3'-stem sequence are each 10 to 19 nucleotides, inclusive, in length. Additionally, the 5'-stem sequence and 3'-stem sequence within any hairpin of the invention can be the same length, or differ in length by less than about 5 bases, which as persons skilled in the art are aware can appear in a hairpin structure as one or more bulge(s). Furthermore, preferably the loop structure is about 2 to 15 nucleotides in length, and more preferably 4-11 nucleotides.

Preferably, overhangs, if any, comprise between 1 to 6 bases. The overhangs can be unmodified, or can contain one or more specificity or stabilizing modifications, such as a halogen or O-alkyl modification of the 2' position, or internucleotide modifications such as phosphorothioate, phosphorodithioate, or methylphosphonate modifications. The overhangs can be ribonucleic acid, deoxyribonucleic acid, or a combination of ribonucleic acid and deoxyribonucleic acid. In the case of an overhang at the 5'-end of the polynucleotide, it is preferred that the modification(s) to the 5'-terminal nucleotide, if any, does not affect the RNAi capability of the hairpin construct. Such a modification can be, for example, a phosphorothioate.

As used herein, the term "double-stranded stem" includes one or more nucleic acid molecules comprising a region of the molecule in which at least a portion of the nucleomonomers are complementary and hydrogen bond to form a double-stranded region.

In other embodiments, the 3'-stem sequence comprises one or more universal base-pairing nucleotides.

In certain embodiments, a double-stranded stem of the hairpin construct contains mismatches and/or loops or bulges, but is double-stranded over at least about 50% of the length of the double-stranded stem. In another embodiment, a double-stranded stem of the invention is double-stranded over at least about 60% of the length of the stem. In another embodiment, a double-stranded stem of the hairpin construct is double-stranded over at least about 70% of the length of the stem. In another embodiment, a double-stranded stem of the hairpin is double-stranded over at least about 80% of the length of the stem. In another embodiment, a double-stranded stem of the hairpin construct is double-stranded over at least about 90%-95% of the length of the double-stranded stem. In another embodiment, a double-stranded stem of the hairpin construct is double-stranded over at least about 96%-98% of the length of the stem. In certain embodiments, the double-stranded stem of the hairpin construct contains at least or up to 1, 2, 3, 4, 5, 6, 7, 8, 9, 10, 11, 12, 13, 14, or 15 mismatches.

Modifications

The nucleotides of the invention may be modified at various locations, including the sugar moiety, the phosphodiester linkage, and/or the base.

Sugar moieties include natural, unmodified sugars, e.g., monosaccharide (such as pentose, e.g., ribose, deoxyribose), modified sugars and sugar analogs. In general, possible modifications of nucleomonomers, particularly of a sugar moiety, include, for example, replacement of one or more of the hydroxyl groups with a halogen, a heteroatom, an aliphatic group, or the functionalization of the hydroxyl group as an ether, an amine, a thiol, or the like.

One particularly useful group of modified nucleomonomers are 2'-O-methyl nucleotides. Such 2'-O-methyl nucleotides may be referred to as "methylated," and the corresponding nucleotides may be made from unmethylated nucleotides followed by alkylation or directly from methylated nucleotide reagents. Modified nucleomonomers may be used in combination with unmodified nucleomonomers. For example, an oligonucleotide of the invention may contain both methylated and unmethylated nucleomonomers.

Some exemplary modified nucleomonomers include sugar- or backbone-modified ribonucleotides. Modified ribonucleotides may contain a nonnaturally occurring base (instead of a naturally occurring base), such as uridines or cytidines modified at the 5'-position, e.g., 5'-(2-amino)propyl uridine and 5'-bromo uridine; adenosines and guanosines modified at the 8-position, e.g., 8-bromo guanosine; deaza nucleotides, e.g., 7-deaza-adenosine; and N-alkylated nucleotides, e.g., N6-methyl adenosine. Also, sugar-modified ribonucleotides may have the 2'-OH group replaced by a H, alxoxy (or OR), R or alkyl, halogen, SH, SR, amino (such as $NH_2$, NHR, $NR_2$,), or CN group, wherein R is lower alkyl, alkenyl, or alkynyl.

Modified ribonucleotides may also have the phosphoester group connecting to adjacent ribonucleotides replaced by a modified group, e.g., of phosphothioate group. More generally, the various nucleotide modifications may be combined.

In one embodiment, sense oligomers may have 2'-modifications on the ends (e.g., 2 on each end, 3 on each end, and 4 on each end, etc.; as well as 1 on one end, 2 on one end, 3 on one end, and 4 on one end, etc.; and even unbalanced combinations such as 12 on one end and 10 on the other end, etc.). Likewise, the antisense strand may have 2'-modifications on the ends (1 on each end, 2 on each end, 3 on each end, and 4 on each end, and so on; as well as 1 on one end, 2 on one end, 3 on one end, and 4 on one end, and so on; and even unbalanced combinations such as 1 on one end and 2 on the other end, and so on). In preferred aspects, the 2'-modifications are 2'-O-methyl modifications in the sense RNA strand and/or the antisense strand.

According to the instant invention, the sense strand can tolerate many 2'-modifications (such as 2'-O-methyl modifications), so long as the central linkages are unmodified. As used herein, "central" is not limited to mean the geometric mid-point of the sense strand. Rather, it can include any location between the 5'-end portion and the 3'-end portion of the sense strand. The 5'-end portion and the 3'-end portion of the sense strand need not be symmetrical.

Thus, in certain embodiments, the sense strand is not completely modified (i.e., at least one or more sense strand nucleotide(s) are unmodified). In certain embodiments, the unmodified sense strand nucleotides are in the central portion of the sense strand, or between the stretch of modified sense strand nucleotides on the 5'-end and the stretch of modified sense strand nucleotides on the 3'-end.

Also according to the instant invention, the sense strand tolerance for 2'-modification is not necessarily symmetrical. Rather, asymmetrical configurations may be desirable when using, for example, a sense strand of 25 or 26 nucleotides.

2'-mofications add nuclease stability, and reduce interferon induction, and are easier to synthesize. Thus it may be desirable to include more such 2'-modified ribose sugars (especially 2'-O-methyl modified) on the sense strand, so long as the teachings of the instant invention is followed to preserve RNAi activity.

In some embodiments of the present invention, the subject highly modified sense strands may be combined with either unmodified or lightly modified antisense strands to allow maximum guide strand activity.

To further maximize endo- and exo-nuclease resistance, in addition to the use of 2'-modified nucleomonomers in the ends, inter-nucleomonomer linkages other than phosphodiesters may be used. For example, such end blocks may be used alone or in conjunction with phosphothioate linkages between the 2'-O-methly linkages. Preferred 2'-modified nucleomonomers are 2'-modified end nucleotides.

Although the antisense strand may be substantially identical to at least a portion of the target PCSK9 gene (or genes), at least with respect to the base pairing properties, the sequence need not be perfectly identical to be useful. Generally, higher homology can be used to compensate for the use of a shorter antisense gene. In some cases, the antisense strand generally will be substantially identical (although in antisense orientation) to the PCSK9 target gene.

One particular example of a composition of the invention has end-blocks on both ends of a sense oligonucleotide and only the 3'-end of an antisense oligonucleotide. Without wishing to be bound by theory, a 2'-O-modified sense strand may work less well than its unmodified version, possibly because it is not efficiently unwound. Thus, in certain embodiments, mismatches may be introduced into specific positions of the sense strand (modified 2'-O-methyl sense strand, or even unmodified sense strand) to facilitate easier loading into the RISC complex.

In some embodiments, the length of the sense strand can be 30, 29, 28, 27, 26, 25, 24, 23, 22, 21, 20, 19, or 18 nucleotides. Similarly, the length of the antisense strand can be 30, 29, 28, 27, 26, 25, 24, 23, 22, 21, 20, 19, or 18 nucleotides. Further, when a double-stranded nucleic acid molecule is formed from such sense and antisense molecules, the resulting duplex may have blunt ends or overhangs of 0, 1, 2, 3, 4, 5, 6, 7, 8, 9, 10, 11, 12, 13, or 14 nucleotides on one end or independently on each end. Further, double stranded nucleic acid molecules of the invention may be composed of a sense strand and an antisense strand wherein these strands are of lengths described above, and are of the same or different lengths, but share only 10, 11, 12, 13, 14, 15, 16, 17, 18, 19, or 20 nucleotides of sequence complementarity. By way of illustration, in a situation where the sense strand is 20 nucleotides in length and the antisense is 25 nucleotides in length and the two strands share only 15 nucleotides of sequence complementarity, a double stranded nucleic acid molecules may be formed with a 10 nucleotide overhang on one end and a 5 nucleotide overhang on the other end.

The use of 2'-O-methyl RNA may also be beneficially in circumstances in which it is desirable to minimize cellular stress responses. RNA having 2'-O-methyl nucleomonomers may not be recognized by cellular machinery that is thought to recognize unmodified RNA. The use of 2'-O-methylated or partially 2'-O-methylated RNA may avoid the interferon response to double-stranded nucleic acids, while maintaining target RNA inhibition. This may be useful, for example, for avoiding the interferon or other cellular stress responses, both in short RNAi (e.g., siRNA) sequences that induce the interferon response, and in longer RNAi sequences that may induce the interferon response.

Overall, modified sugars may include D-ribose, 2'-O-alkyl (including 2'-O-methyl and 2'-O-ethyl), i.e., 2'-alkoxy, 2'-amino, 2'-S-alkyl, 2'-halo (including 2'-fluoro), 2'-methoxyethoxy, 2'-allyloxy (—OCH$_2$CH=CH$_2$), 2'-propargyl, 2'-propyl, ethynyl, ethenyl, propenyl, and cyano and the like. In one embodiment, the sugar moiety can be a hexose and incorporated into an oligonucleotide as described (Augustyns, K., et al., *Nucl. Acids. Res.* 18:4711 (1992)). Exemplary nucleomonomers can be found, e.g., in U.S. Pat. No. 5,849,902, incorporated by reference herein.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, unless otherwise specified, the term alkyl includes both "unsubstituted alkyls" and "substituted alkyls," the latter of which refers to alkyl moieties having independently selected substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids. The term "n-alkyl" means a straight chain (i.e., unbranched) unsubstituted alkyl group.

The term "alkenyl" includes unsaturated aliphatic groups analogous in length and possible substitution to the alkyls described above, but that contain at least one double bond. For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, unless otherwise specified, the term alkenyl includes both "unsubstituted alkenyls" and "substituted alkenyls," the latter of which refers to alkenyl moieties having independently selected substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, unless otherwise specified, the term alkynyl includes both "unsubstituted alkynyls" and "substituted alkynyls," the latter of which refers to alkynyl moieties having independently selected substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with independently selected groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "heteroatom" includes atoms of any element other than carbon or hydrogen. Preferred heteroatoms are nitrogen, oxygen, sulfur and phosphorus.

The term "hydroxy" or "hydroxyl" includes groups with an —OH or —O$^-$ (with an appropriate counterion).

The term "halogen" includes fluorine, bromine, chlorine, iodine, etc. The term "perhalogenated" generally refers to a moiety wherein all hydrogens are replaced by halogen atoms.

The term "substituted" includes independently selected substituents which can be placed on the moiety and which allow the molecule to perform its intended function. Examples of substituents include alkyl, alkenyl, alkynyl, aryl, $(CR'R'')_{0-3}NR'R''$, $(CR'R'')_{0-3}CN$, $NO_2$, halogen, $(CR'R'')_{0-3}C(halogen)_3$, $(CR'R'')_{0-3}CH(halogen)_2$, $(CR'R'')_{0-3}CH_2(halogen)$, $(CR'R'')_{0-3}CONR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-2}R'$, $(CR'R'')_{0-3}O(CR'R'')_{0-3}H$, $(CR'R'')_{0-3}COR'$, $(CR'R'')_{0-3}CO_2R'$, or $(CR'R'')_{0-3}OR'$ groups; wherein each R' and R'' are each independently hydrogen, a $C_1$-$C_5$ alkyl, $C_2$-$C_5$ alkenyl, $C_2$-$C_5$ alkynyl, or aryl group, or R' and R'' taken together are a benzylidene group or a —$(CH_2)_2O(CH_2)_2$— group.

The term "amine" or "amino" includes compounds or moieties in which a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups.

The term "ether" includes compounds or moieties which contain an oxygen bonded to two different carbon atoms or heteroatoms. For example, the term includes "alkoxyalkyl," which refers to an alkyl, alkenyl, or alkynyl group covalently bonded to an oxygen atom which is covalently bonded to another alkyl group.

The term "base" includes the known purine and pyrimidine heterocyclic bases, deazapurines, and analogs (including heterocyclic substituted analogs, e.g., aminoethyoxy phenoxazine), derivatives (e.g., 1-alkyl-, 1-alkenyl-, heteroaromatic- and 1-alkynyl derivatives) and tautomers thereof. Examples of purines include adenine, guanine, inosine, diaminopurine, and xanthine and analogs (e.g., 8-oxo-N-6-methyladenine or 7-diazaxanthine) and derivatives thereof. Pyrimidines include, for example, thymine, uracil, and cytosine, and their analogs (e.g., 5-methylcytosine, 5-methyluracil, 5-(1-propynyl)uracil, 5-(1-propynyl)cytosine and 4,4-ethanocytosine). Other examples of suitable bases include non-purinyl and non-pyrimidinyl bases such as 2-aminopyridine and triazines.

In a preferred embodiment, the nucleomonomers of an oligonucleotide of the invention are RNA nucleotides. In another preferred embodiment, the nucleomonomers of an oligonucleotide of the invention are modified RNA nucleotides. Thus, the oligunucleotides contain modified RNA nucleotides.

The term "nucleoside" includes bases which are covalently attached to a sugar moiety, preferably ribose or deoxyribose. Examples of preferred nucleosides include ribonucleosides and deoxyribonucleosides. Nucleosides also include bases linked to amino acids or amino acid analogs which may comprise free carboxyl groups, free amino groups, or protecting groups. Suitable protecting groups are well known in the art (see P. G. M. Wuts and T. W. Greene, "Protective Groups in Organic Synthesis", $2^{nd}$ Ed., Wiley-Interscience, New York, 1999).

The term "nucleotide" includes nucleosides which further comprise a phosphate group or a phosphate analog.

As used herein, the term "linkage" includes a naturally occurring, unmodified phosphodiester moiety (—O—($PO^{2-}$)—O—) that covalently couples adjacent nucleomonomers. As used herein, the term "substitute linkage" includes any analog or derivative of the native phosphodiester group that covalently couples adjacent nucleomonomers. Substitute linkages include phosphodiester analogs, e.g., phosphorothioate, phosphorodithioate, and P-ethyoxyphosphodiester, P-ethoxyphosphodiester, P-alkyloxyphosphotriester, methylphosphonate, and nonphosphorus containing linkages, e.g., acetals and amides. Such substitute linkages are known in the art (e.g., Bjergarde et al. 1991. Nucleic Acids Res. 19:5843; Caruthers et al. 1991. Nucleosides Nucleotides. 10:47). In certain embodiments, non-hydrolizable linkages are preferred, such as phosphorothiate linkages.

In certain embodiments, oligonucleotides of the invention comprise 3' and 5' termini (except for circular oligonucleotides). In one embodiment, the 3' and 5' termini of an oligonucleotide can be substantially protected from nucleases e.g., by modifying the 3' or 5' linkages (e.g., U.S. Pat. No. 5,849,902 and WO 98/13526). For example, oligonucleotides can be made resistant by the inclusion of a "blocking group." The term "blocking group" as used herein refers to substituents (e.g., other than OH groups) that can be attached to oligonucleotides or nucleomonomers, either as protecting groups or coupling groups for synthesis (e.g., FITC, propyl ($CH_2$—$CH_2$—$CH_3$), glycol (—O—$CH_2$—$CH_2$—O—) phosphate ($PO_3^{2-}$), hydrogen phosphonate, or phosphoramidite). "Blocking groups" also include "end blocking groups" or "exonuclease blocking groups" which protect the 5' and 3' termini of the oligonucleotide, including modified nucleotides and non-nucleotide exonuclease resistant structures.

Exemplary end-blocking groups include cap structures (e.g., a 7-methylguanosine cap), inverted nucleomonomers, e.g., with 3'-3' or 5'-5' end inversions (see, e.g., Ortiagao et al. 1992. *Antisense Res. Dev.* 2:129), methylphosphonate, phosphoramidite, non-nucleotide groups (e.g., non-nucleotide linkers, amino linkers, conjugates) and the like. The 3' terminal nucleomonomer can comprise a modified sugar moiety. The 3' terminal nucleomonomer comprises a 3'-O that can optionally be substituted by a blocking group that prevents 3'-exonuclease degradation of the oligonucleotide. For example, the 3'-hydroxyl can be esterified to a nucleotide through a 3'→3' internucleotide linkage. For example, the alkyloxy radical can be methoxy, ethoxy, or isopropoxy, and preferably, ethoxy. Optionally, the 3'→3' linked nucleotide at the 3' terminus can be linked by a substitute linkage. To reduce nuclease degradation, the 5' most 3'→5' linkage can be a modified linkage, e.g., a phosphorothioate or a P-alkyloxyphosphotriester linkage. Preferably, the two 5' most 3'→5' linkages are modified linkages. Optionally, the 5' terminal hydroxy moiety can be esterified with a phosphorus containing moiety, e.g., phosphate, phosphorothioate, or P-ethoxyphosphate.

In one embodiment, the sense strand of an oligonucleotide comprises a 5' group that allows for RNAi activity but which renders the sense strand inactive in terms of gene targeting. Preferably, such a 5' modifying group is a phosphate group or a group larger than a phosphate group. Oligonucleotides of this type often exhibit increased specificity for a target gene in a cell that corresponds to the nucleotide sequence of the antisense strand. This is because the sense strand in such an oligonucleotide is often rendered incapable of mediating cleavage of any nucleotide sequence it might bind to non-specifically and thus will not inactivate any other genes in the cell. Thus, observed decrease in the expression of a PCSK9 gene within a cell transfected with such an oligonucleotide will often be attributed to the direct or indirect effect of the antisense strand. Thus, according to another embodiment, the invention provides a method of increasing the specificity of an oligonucleotide for a target PCSK9 gene in a cell, wherein said oligonucleotide comprises a sense strand and an antisense strand, wherein both the sense strand and the antisense strand are capable of binding to corresponding nucleotide sequences if present in said cell, said method comprising the step of modifying the 5' terminal hydroxy moiety of said sense strand with a phosphate group or a group larger than a phosphate group prior to contacting said oligonucleotide with said cell so as to render said sense strand incapable of mediating cleavage of any nucleotide sequence it might bind to non-specifically and thus will not inactivate any other genes in the cell.

Another way to increase target gene specificity, or to reduce off-target silencing effect, is to introduce a 2'-modification (such as the 2'-O methyl modification) at a position corresponding to the second 5'-end nucleotide of the Dicer-cleaved 21-mer. Applicants' discovery allows the positioning of this 2'-modification in the Dicer-resistant dsRNA, thus enabling one to design better siRNA constructs with less or no off-target silencing.

In one embodiment, a double-stranded oligonucleotide of the invention can comprise (i.e., be a duplex of) one nucleic acid molecule which is DNA and one nucleic acid molecule which is RNA. Antisense sequences of the invention can be "chimeric oligonucleotides" which comprise an RNA-like and a DNA-like region.

The language "RNase H activating region" includes a region of an oligonucleotide, e.g., a chimeric oligonucleotide, that is capable of recruiting RNase H to cleave the target RNA strand to which the oligonucleotide binds. Typically, the RNase activating region contains a minimal core (of at least about 3-5, typically between about 3-12, more typically, between about 5-12, and more preferably between about 5-10 contiguous nucleomonomers) of DNA or DNA-like nucleomonomers. (See, e.g., U.S. Pat. No. 5,849,902). Preferably, the RNase H activating region comprises about nine contiguous deoxyribose containing nucleomonomers.

The language "non-activating region" includes a region of an antisense sequence, e.g., a chimeric oligonucleotide, that does not recruit or activate RNase H. Preferably, a non-activating region does not comprise phosphorothioate DNA. The oligonucleotides of the invention comprise at least one non-activating region. In one embodiment, the non-activating region can be stabilized against nucleases or can provide specificity for the target by being complementary to the target and forming hydrogen bonds with the target nucleic acid molecule, which is to be bound by the oligonucleotide.

In one embodiment, at least a portion of the contiguous polynucleotides are linked by a substitute linkage, e.g., a phosphorothioate linkage.

In certain embodiments, most or all of the sense strand nucleotides (2'-modified or not) are linked by phopshorothiaote linkages. Such constructs tend to have improved pharmacokinetics due to their higher affinity for serum proteins. The phosphothiaote linkages in the sense strand generally do not interfere with guide strand activity, once the latter is loaded into RISC.

Antisense sequences of the present invention may include "morpholino oligonucleotides." Morpholino oligonucleotides are non-ionic and function by an RNase H-independent mechanism. Each of the 4 genetic bases (Adenine, Cytosine, Guanine, and Thymine/Uracil) of the morpholino oligonucleotides is linked to a 6-membered morpholine ring. Morpholino oligonucleotides are made by joining the 4 different subunit types by, e.g., non-ionic phosphorodiamidate inter-subunit linkages. Morpholino oligonucleotides have many advantages including: complete resistance to nucleases (Antisense & Nucl. Acid Drug Dev. 1996. 6:267); predictable targeting (Biochemica Biophysica Acta. 1999. 1489:141); reliable activity in cells (Antisense & Nucl. Acid Drug Dev. 1997. 7:63); excellent sequence specificity (Antisense & Nucl. Acid Drug Dev. 1997. 7:151); minimal non-antisense activity (Biochemica Biophysica Acta. 1999. 1489:141); and simple osmotic or scrape delivery (Antisense & Nucl. Acid Drug Dev. 1997. 7:291). Morpholino oligonucleotides are also preferred because of their non-toxicity at high doses. A discussion of the preparation of morpholino oligonucleotides can be found in Antisense & Nucl. Acid Drug Dev. 1997. 7:187.

III. Synthesis

Oligonucleotides of the invention can be synthesized by any method known in the art, e.g., using enzymatic synthesis and/or chemical synthesis. The oligonucleotides can be synthesized in vitro (e.g., using enzymatic synthesis and chemical synthesis) or in vivo (using recombinant DNA technology well known in the art).

In a preferred embodiment, chemical synthesis is used for modified polynucleotides. Chemical synthesis of linear oligonucleotides is well known in the art and can be achieved by solution or solid phase techniques. Preferably, synthesis is by solid phase methods. Oligonucleotides can be made by any of several different synthetic procedures including the phosphoramidite, phosphite triester, H-phosphonate, and phosphotriester methods, typically by automated synthesis methods.

Oligonucleotide synthesis protocols are well known in the art and can be found, e.g., in U.S. Pat. No. 5,830,653; WO 98/13526; Stec et al. 1984. *J. Am. Chem. Soc.* 106:6077; Stec et al. 1985. *J. Org. Chem.* 50:3908; Stec et al. *J. Chromatog.* 1985. 326:263; LaPlanche et al. 1986. *Nucl. Acid. Res.* 1986. 14:9081; Fasman G. D., 1989. Practical Handbook of Biochemistry and Molecular Biology. 1989. CRC Press, Boca Raton, Fla.; Lamone. 1993. *Biochem. Soc. Trans.* 21:1; U.S. Pat. Nos. 5,013,830; 5,214,135; 5,525,719; Kawasaki et al. 1993. *J. Med. Chem.* 36:831; WO 92/03568; U.S. Pat. Nos. 5,276,019; and 5,264,423.

The synthesis method selected can depend on the length of the desired oligonucleotide and such choice is within the skill of the ordinary artisan. For example, the phosphoramidite and phosphite triester method can produce oligonucleotides having 175 or more nucleotides, while the H-phosphonate method works well for oligonucleotides of less than 100 nucleotides. If modified bases are incorporated into the oligonucleotide, and particularly if modified phosphodiester linkages are used, then the synthetic procedures are altered as needed according to known procedures. In this regard, Uhlmann et al. (1990, *Chemical Reviews* 90:543-584) provide references and outline procedures for making oligonucleotides with modified bases and modified phosphodiester linkages. Other exemplary methods for making oligonucleotides are taught in Sonveaux. 1994. "Protecting Groups in Oligonucleotide Synthesis"; Agrawal. *Methods in Molecular Biology* 26:1. Exemplary synthesis methods are also taught in "Oligonucleotide Synthesis—A Practical Approach" (Gait, M. J. IRL Press at Oxford University Press. 1984). Moreover, linear oligonucleotides of defined sequence, including some sequences with modified nucleotides, are readily available from several commercial sources.

The oligonucleotides may be purified by polyacrylamide gel electrophoresis, or by any of a number of chromatographic methods, including gel chromatography and high pressure liquid chromatography. To confirm a nucleotide sequence, especially unmodified nucleotide sequences, oligonucleotides may be subjected to DNA sequencing by any of the known procedures, including Maxam and Gilbert sequencing, Sanger sequencing, capillary electrophoresis sequencing, the wandering spot sequencing procedure or by using selective chemical degradation of oligonucleotides bound to Hybond paper. Sequences of short oligonucleotides can also be analyzed by laser desorption mass spectroscopy or by fast atom bombardment (McNeal, et al., 1982, *J. Am. Chem. Soc.* 104:976; Viari, et al., 1987, *Biomed. Environ. Mass Spectrom.* 14:83; Grotjahn et al., 1982, *Nuc. Acid Res.* 10:4671). Sequencing methods are also available for RNA oligonucleotides.

The quality of oligonucleotides synthesized can be verified by testing the oligonucleotide by capillary electrophoresis and denaturing strong anion HPLC (SAX-HPLC) using, e.g., the method of Bergot and Egan. 1992. *J. Chrom.* 599:35.

Other exemplary synthesis techniques are well known in the art (see, e.g., Sambrook et al., Molecular Cloning: a Laboratory Manual, Second Edition (1989); DNA Cloning, Volumes I and II (D N Glover Ed. 1985); Oligonucleotide Synthesis (M J Gait Ed, 1984; Nucleic Acid Hybridisation (B D Hames and S J Higgins eds. 1984); A Practical Guide to Molecular Cloning (1984); or the series, Methods in Enzymology (Academic Press, Inc.)).

In certain embodiments, the subject RNAi constructs or at least portions thereof are transcribed from expression vectors encoding the subject constructs. Any art recognized vectors may be use for this purpose. The transcribed RNAi constructs may be isolated and purified, before desired modifications (such as replacing an unmodified sense strand with a modified one, etc.) are carried out.

IV. Delivery/Carrier

Uptake of Oligonucleotides by Cells

Oligonucleotides and oligonucleotide compositions are contacted with (i.e., brought into contact with, also referred to herein as administered or delivered to) and taken up by one or more cells or a cell lysate. The term "cells" includes prokaryotic and eukaryotic cells, preferably vertebrate cells, and, more preferably, mammalian cells. In a preferred embodiment, the oligonucleotide compositions of the invention are contacted with human cells.

Oligonucleotide compositions of the invention can be contacted with cells in vitro, e.g., in a test tube or culture dish, (and may or may not be introduced into a subject) or in vivo, e.g., in a subject such as a mammalian subject.

Oligonucleotides are taken up by cells at a slow rate by endocytosis, but endocytosed oligonucleotides are generally sequestered and not available, e.g., for hybridization to a target nucleic acid molecule. In one embodiment, cellular uptake can be facilitated by electroporation or calcium phosphate precipitation. However, these procedures are only useful for in vitro or ex vivo embodiments, are not convenient and, in some cases, are associated with cell toxicity.

In another embodiment, delivery of oligonucleotides into cells can be enhanced by suitable art recognized methods including calcium phosphate, DMSO, glycerol or dextran, electroporation, or by transfection, e.g., using cationic, anionic, or neutral lipid compositions or liposomes using methods known in the art (see e.g., WO 90/14074; WO 91/16024; WO 91/17424; U.S. Pat. No. 4,897,355; Bergan et al. 1993. *Nucleic Acids Research*. 21:3567). Enhanced delivery of oligonucleotides can also be mediated by the use of vectors (See e.g., Shi, Y. 2003. Trends Genet. 2003 Jan. 19:9; Reichhart J. Metal. Genesis. 2002. 34(1-2):1604, Yu et al. 2002. Proc. Natl. Acad. Sci. USA 99:6047; Sui et al. 2002. Proc. Natl. Acad. Sci. USA 99:5515) viruses, polyamine or polycation conjugates using compounds such as polylysine, protamine, or Ni, N12-bis(ethyl)spermine (see, e.g., Bartzatt, R. et al. 1989. *Biotechnol. Appl. Biochem.* 11:133; Wagner E. et al. 1992. *Proc. Natl. Acad. Sci.* 88:4255).

The optimal protocol for uptake of oligonucleotides will depend upon a number of factors, the most crucial being the type of cells that are being used. Other factors that are important in uptake include, but are not limited to, the nature and concentration of the oligonucleotide, the confluence of the cells, the type of culture the cells are in (e.g., a suspension culture or plated) and the type of media in which the cells are grown.

Conjugating Agents

Conjugating agents bind to the oligonucleotide in a covalent manner. In one embodiment, oligonucleotides can be derivatized or chemically modified by binding to a conjugating agent to facilitate cellular uptake. For example, covalent linkage of a cholesterol moiety to an oligonucleotide can improve cellular uptake by 5- to 10-fold which in turn improves DNA binding by about 10-fold (Boutorin et al., 1989, *FEBS Letters* 254:129-132). Conjugation of octyl, dodecyl, and octadecyl residues enhances cellular uptake by 3-, 4-, and 10-fold as compared to unmodified oligonucleotides (Vlassov et al., 1994, Biochimica et Biophysica Acta 1197:95-108). Similarly, derivatization of oligonucleotides with poly-L-lysine can aid oligonucleotide uptake by cells (Schell, 1974, *Biochem. Biophys. Acta* 340:323, and Lemaitre et al., 1987, *Proc. Natl. Acad. Sci. USA* 84:648).

Certain protein carriers can also facilitate cellular uptake of oligonucleotides, including, for example, serum albumin, nuclear proteins possessing signals for transport to the nucleus, and viral or bacterial proteins capable of cell membrane penetration. Therefore, protein carriers are useful when associated with or linked to the oligonucleotides. Accordingly, the present invention provides for derivatization of oligonucleotides with groups capable of facilitating cellular uptake, including hydrocarbons and non-polar groups, cholesterol, long chain alcohols (i.e., hexanol), poly-L-lysine and proteins, as well as other aryl or steroid groups and polycations having analogous beneficial effects, such as phenyl or naphthyl groups, quinoline, anthracene or phenanthracene groups, fatty acids, fatty alcohols and sesquiterpenes, diterpenes, and steroids. A major advantage of using conjugating agents is to increase the initial membrane interaction that leads to a greater cellular accumulation of oligonucleotides.

Other conjugating agents include various vitamins, such as fat soluble vitamins, which may be used as a conjugate to deliver RNAi constructs specifically into adipose tissue—the primary location where these vitamins are stored. These vitamin-based conjugating agents may be especially useful for targeting certain metabolic disease targets, such as diabetes/obesity. Of the fat soluble vitamins, such as vitamins A, D, E, K, etc., vitamin K may be preferred in some embodiments, as there is no known upper intake level (although large doses could lead to breakdown of red blood cells and possibly to liver disease). In comparison, vitamins A and D have more defined toxicity and established upper intake levels.

In certain embodiments, gamma carboxyglutamic acid residues may be conjugated to the subject RNAi constructs to increased their membrane stickiness, and/or to slow clearance and improve general uptake (infra).

Certain conjugating agents that may be used with the instant constructs include those described in WO04048545A2 and US20040204377A1 (all incorporated herein by their entireties), such as a Tat peptide, a sequence substantially similar to the sequence of SEQ ID NO: 12 of WO04048545A2 and US20040204377A1, a homeobox (hox) peptide, a MTS, VP22, MPG, at least one dendrimer (such as PAMAM), etc.

Other conjugating agents that may be used with the instant constructs include those described in WO07089607A2 (incorporated herein), which describes various nanotransporters and delivery complexes for use in delivery of nucleic acid molecules (such as the subject dsRNA constructs) and/or other pharmaceutical agents in vivo and in vitro. Using such delivery complexes, the subject dsRNA can be delivered while conjugated or associated with a nanotransporter comprising a core conjugated with at least one functional surface group. The core may be a nanoparticle, such as a dendrimer (e.g., a polylysine dendrimer). The core may also be a nanotube, such as a single walled nanotube or a multi-walled nanotube. The functional surface group is at least one of a lipid, a cell type specific targeting moiety, a fluorescent molecule, and a charge controlling molecule. For example, the targeting moiety may be a tissue-selective peptide. The lipid may be an oleoyl lipid or derivative thereof. Exemplary nanotransporter include NOP-7 or HBOLD.

Encapsulating Agents

Encapsulating agents entrap oligonucleotides within vesicles. In another embodiment of the invention, an oligonucleotide may be associated with a carrier or vehicle, e.g., liposomes or micelles, although other carriers could be used, as would be appreciated by one skilled in the art. Liposomes are vesicles made of a lipid bilayer having a structure similar to biological membranes. Such carriers are used to facilitate the cellular uptake or targeting of the oligonucleotide, or improve the oligonucleotide's pharmacokinetic or toxicologic properties.

For example, the oligonucleotides of the present invention may also be administered encapsulated in liposomes, pharmaceutical compositions wherein the active ingredient is contained either dispersed or variously present in corpuscles consisting of aqueous concentric layers adherent to lipidic layers. The oligonucleotides, depending upon solubility, may be present both in the aqueous layer and in the lipidic layer, or in what is generally termed a liposomic suspension. The hydrophobic layer, generally but not exclusively, comprises phopholipids such as lecithin and sphingomyelin, steroids such as cholesterol, more or less ionic surfactants such as diacetylphosphate, stearylamine, or phosphatidic acid, or other materials of a hydrophobic nature. The diameters of the liposomes generally range from about 15 nm to about 5 microns.

The use of liposomes as drug delivery vehicles offers several advantages. Liposomes increase intracellular stability, increase uptake efficiency and improve biological activity. Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver nucleic acids to cells and that the nucleic acids remain biologically active. For example, a lipid delivery vehicle originally designed as a research tool, such as Lipofectin or LIPOFECTAMINE™ 2000, can deliver intact nucleic acid molecules to cells.

Specific advantages of using liposomes include the following: they are non-toxic and biodegradable in composition; they display long circulation half-lives; and recognition molecules can be readily attached to their surface for targeting to tissues. Finally, cost-effective manufacture of liposome-based pharmaceuticals, either in a liquid suspension or lyophilized product, has demonstrated the viability of this technology as an acceptable drug delivery system.

Complexing Agents

Complexing agents bind to the oligonucleotides of the invention by a strong but non-covalent attraction (e.g., an electrostatic, van der Waals, pi-stacking, etc. interaction). In one embodiment, oligonucleotides of the invention can be complexed with a complexing agent to increase cellular uptake of oligonucleotides. An example of a complexing agent includes cationic lipids. Cationic lipids can be used to deliver oligonucleotides to cells.

The term "cationic lipid" includes lipids and synthetic lipids having both polar and non-polar domains and which are capable of being positively charged at or around physiological pH and which bind to polyanions, such as nucleic acids, and facilitate the delivery of nucleic acids into cells. In general cationic lipids include saturated and unsaturated alkyl and alicyclic ethers and esters of amines, amides, or derivatives thereof. Straight-chain and branched alkyl and alkenyl groups of cationic lipids can contain, e.g., from 1 to about 25 carbon atoms. Preferred straight chain or branched alkyl or alkene groups have six or more carbon atoms. Alicyclic groups include cholesterol and other steroid groups. Cationic lipids can be prepared with a variety of counterions (anions) including, e.g., Cl$^-$, Br$^-$, I$^-$, F$^-$, acetate, trifluoroacetate, sulfate, nitrite, and nitrate.

Examples of cationic lipids include polyethylenimine, polyamidoamine (PAMAM) starburst dendrimers, Lipofectin (a combination of DOTMA and DOPE), Lipofectase, LIPOFECTAMINE™ (e.g., LIPOFECTAMINE™ 2000), DOPE, Cytofectin (Gilead Sciences, Foster City, Calif.), and Eufectins (JBL, San Luis Obispo, Calif.). Exemplary cationic liposomes can be made from N-[1-(2,3-dioleoloxy)-propyl]-N,N,N-trimethylammonium chloride (DOTMA), N-[1-(2,3-dioleoloxy)-propyl]-N,N,N-trimethylammonium methylsulfate (DOTAP), 3β-[N—(N',N'-dimethylaminoethane)carbamoyl]cholesterol (DC-Chol), 2,3,-dioleyloxy-N-[2 (sperminecarboxamido)ethyl]-N,N-dimethyl-1-propan-aminium trifluoroacetate (DOSPA), 1,2-dimyristyloxypropyl-3-dimethyl-hydroxyethyl ammonium bromide; and dimethyldioctadecylammonium bromide (DDAB). The cationic lipid N-(1-(2,3-dioleyloxy)propyl)-N,N,N-trimethylammonium chloride (DOTMA), for example, was found to increase 1000-fold the antisense effect of a phosphothioate oligonucleotide. (Vlassov et al., 1994, Biochimica et Biophysica Acta 1197:95-108). Oligonucleotides can also be complexed with, e.g., poly (L-lysine) or avidin and lipids may, or may not, be included in this mixture, e.g., steryl-poly (L-lysine).

Cationic lipids have been used in the art to deliver oligonucleotides to cells (see, e.g., U.S. Pat. Nos. 5,855,910; 5,851,548; 5,830,430; 5,780,053; 5,767,099; Lewis et al. 1996. *Proc. Natl. Acad. Sci. USA* 93:3176; Hope et al. 1998. *Molecular Membrane Biology* 15:1). Other lipid compositions which can be used to facilitate uptake of the instant oligonucleotides can be used in connection with the claimed methods. In addition to those listed supra, other lipid compositions are also known in the art and include, e.g., those taught in U.S. Pat. No. 4,235,871; U.S. Pat. Nos. 4,501,728; 4,837,028; 4,737,323.

In one embodiment lipid compositions can further comprise agents, e.g., viral proteins to enhance lipid-mediated transfections of oligonucleotides (Kamata, et al., 1994. *Nucl. Acids. Res.* 22:536). In another embodiment, oligonucleotides are contacted with cells as part of a composition comprising an oligonucleotide, a peptide, and a lipid as taught, e.g., in U.S. Pat. No. 5,736,392. Improved lipids have also been described which are serum resistant (Lewis, et al., 1996. *Proc. Natl. Acad. Sci.* 93:3176). Cationic lipids and other complexing agents act to increase the number of oligonucleotides carried into the cell through endocytosis.

In another embodiment N-substituted glycine oligonucleotides (peptoids) can be used to optimize uptake of oligonucleotides. Peptoids have been used to create cationic lipid-like compounds for transfection (Murphy, et al., 1998. *Proc. Natl. Acad. Sci.* 95:1517). Peptoids can be synthesized using standard methods (e.g., Zuckermann, R. N., et al. 1992. *J. Am. Chem. Soc.* 114:10646; Zuckermann, R. N., et al. 1992. *Int. J. Peptide Protein Res.* 40:497). Combinations of cationic lipids and peptoids, liptoids, can also be used to optimize uptake of the subject oligonucleotides (Hunag, et al., 1998. *Chemistry and Biology.* 5:345). Liptoids can be synthesized by elaborating peptoid oligonucleotides and coupling the amino terminal submonomer to a lipid via its amino group (Hunag, et al., 1998. *Chemistry and Biology.* 5:345).

It is known in the art that positively charged amino acids can be used for creating highly active cationic lipids (Lewis et al. 1996. *Proc. Natl. Acad. Sci. USA.* 93:3176). In one embodiment, a composition for delivering oligonucleotides of the invention comprises a number of arginine, lysine, histidine or ornithine residues linked to a lipophilic moiety (see e.g., U.S. Pat. No. 5,777,153).

In another embodiment, a composition for delivering oligonucleotides of the invention comprises a peptide having from between about one to about four basic residues. These basic residues can be located, e.g., on the amino terminal, C-terminal, or internal region of the peptide. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine (can also be considered non-polar), asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Apart from the basic amino acids, a majority or all of the other residues of the peptide can be selected from the non-basic amino acids, e.g., amino acids other than lysine, arginine, or histidine. Preferably a preponderance of neutral amino acids with long neutral side chains are used.

In one embodiment, a composition for delivering oligonucleotides of the invention comprises a natural or synthetic polypeptide having one or more gamma carboxyglutamic acid residues, or γ-Gla residues. These gamma carboxyglutamic acid residues may enable the polypeptide to bind to each other and to membrane surfaces. In other words, a polypeptide having a series of γ-Gla may be used as a general delivery modality that helps an RNAi construct to stick to whatever membrane to which it comes in contact. This may at least slow RNAi constructs from being cleared from the blood stream and enhance their chance of homing to the target.

The gamma carboxyglutamic acid residues may exist in natural proteins (for example, prothrombin has 10 γ-Gla residues). Alternatively, they can be introduced into the purified, recombinantly produced, or chemically synthesized polypeptides by carboxylation using, for example, a vitamin K-dependent carboxylase. The gamma carboxyglutamic acid residues may be consecutive or non-consecutive, and the total number and location of such gamma carboxyglutamic acid residues in the polypeptide can be regulated/fine tuned to achieve different levels of "stickiness" of the polypeptide.

In one embodiment, the cells to be contacted with an oligonucleotide composition of the invention are contacted with a mixture comprising the oligonucleotide and a mixture comprising a lipid, e.g., one of the lipids or lipid compositions described supra for between about 12 hours to about 24 hours. In another embodiment, the cells to be contacted with an oligonucleotide composition are contacted with a mixture comprising the oligonucleotide and a mixture comprising a lipid, e.g., one of the lipids or lipid compositions described supra for between about 1 and about five days. In one embodiment, the cells are contacted with a mixture comprising a lipid and the oligonucleotide for between about three days to as long as about 30 days. In another embodiment, a mixture comprising a lipid is left in contact with the cells for at least about five to about 20 days. In another embodiment, a mixture comprising a lipid is left in contact with the cells for at least about seven to about 15 days.

For example, in one embodiment, an oligonucleotide composition can be contacted with cells in the presence of a lipid such as cytofectin CS or GSV (available from Glen Research; Sterling, Va.), GS3815, GS2888 for prolonged incubation periods as described herein.

In one embodiment, the incubation of the cells with the mixture comprising a lipid and an oligonucleotide composition does not reduce the viability of the cells. Preferably, after the transfection period the cells are substantially viable. In one embodiment, after transfection, the cells are between at least about 70% and at least about 100% viable. In another embodiment, the cells are between at least about 80% and at least about 95% viable. In yet another embodiment, the cells are between at least about 85% and at least about 90% viable.

In one embodiment, oligonucleotides are modified by attaching a peptide sequence that transports the oligonucleotide into a cell, referred to herein as a "transporting peptide." In one embodiment, the composition includes an oligonucleotide which is complementary to a target nucleic acid molecule encoding the protein, and a covalently attached transporting peptide.

The language "transporting peptide" includes an amino acid sequence that facilitates the transport of an oligonucleotide into a cell. Exemplary peptides which facilitate the transport of the moieties to which they are linked into cells are known in the art, and include, e.g., HIV TAT transcription factor, lactoferrin, Herpes VP22 protein, and fibroblast growth factor 2 (Pooga et al. 1998. *Nature Biotechnology.* 16:857; and Derossi et al. 1998. *Trends in Cell Biology.* 8:84; Elliott and O'Hare. 1997. Cell 88:223).

Oligonucleotides can be attached to the transporting peptide using known techniques, e.g., (Prochiantz, A. 1996. *Curr. Opin. Neurobiol.* 6:629; Derossi et al. 1998. *Trends Cell Biol.* 8:84; Troy et al. 1996. *J. Neurosci.* 16:253), Vives et al. 1997. *J. Biol. Chem.* 272:16010). For example, in one embodiment, oligonucleotides bearing an activated thiol group are linked via that thiol group to a cysteine present in a transport peptide (e.g., to the cysteine present in the β turn between the second and the third helix of the antennapedia homeodomain as taught, e.g., in Derossi et al. 1998. *Trends Cell Biol.* 8:84; Prochiantz. 1996. *Current Opinion in Neurobiol.* 6:629; Allinquant et al. 1995. J. Cell Biol. 128:919). In another embodiment, a Boc-Cys-(Npys)OH group can be coupled to the transport peptide as the last (N-terminal) amino acid and an oligonucleotide bearing an SH group can be coupled to the peptide (Troy et al. 1996. *J. Neurosci.* 16:253).

In one embodiment, a linking group can be attached to a nucleomonomer and the transporting peptide can be covalently attached to the linker. In one embodiment, a linker can function as both an attachment site for a transporting peptide and can provide stability against nucleases. Examples of suitable linkers include substituted or unsubstituted $C_1$-$C_{20}$ alkyl chains, $C_2$-$C_{20}$ alkenyl chains, $C_2$-$C_{20}$ alkynyl chains, peptides, and heteroatoms (e.g., S, O, NH, etc.). Other exemplary linkers include bifunctional crosslinking agents such as sulfosuccinimidyl-4-(maleimidophenyl)-butyrate (SMPB) (see, e.g., Smith et al. Biochem J 1991.276: 417-2).

In one embodiment, oligonucleotides of the invention are synthesized as molecular conjugates which utilize receptor-mediated endocytotic mechanisms for delivering genes into cells (see, e.g., Bunnell et al. 1992. *Somatic Cell and Molecular Genetics.* 18:559, and the references cited therein).

Targeting Agents

The delivery of oligonucleotides can also be improved by targeting the oligonucleotides to a cellular receptor. The targeting moieties can be conjugated to the oligonucleotides or attached to a carrier group (i.e., poly(L-lysine) or liposomes) linked to the oligonucleotides. This method is well suited to cells that display specific receptor-mediated endocytosis.

For instance, oligonucleotide conjugates to 6-phosphomannosylated proteins are internalized 20-fold more efficiently by cells expressing mannose 6-phosphate specific receptors than free oligonucleotides. The oligonucleotides may also be coupled to a ligand for a cellular receptor using a biodegradable linker. In another example, the delivery construct is mannosylated streptavidin which forms a tight complex with biotinylated oligonucleotides. Mannosylated streptavidin was found to increase 20-fold the internalization of biotinylated oligonucleotides. (Vlassov et al. 1994. *Biochimica et Biophysica Acta* 1197:95-108).

In addition specific ligands can be conjugated to the polylysine component of polylysine-based delivery systems. For example, transferrin-polylysine, adenovirus-polylysine, and influenza virus hemagglutinin HA-2 N-terminal fusogenic peptides-polylysine conjugates greatly enhance receptor-mediated DNA delivery in eucaryotic cells. Mannosylated glycoprotein conjugated to poly(L-lysine) in aveolar macrophages has been employed to enhance the cellular uptake of oligonucleotides. Liang et al. 1999. *Pharmazie* 54:559-566.

Because malignant cells have an increased need for essential nutrients such as folic acid and transferrin, these nutrients can be used to target oligonucleotides to cancerous cells. For example, when folic acid is linked to poly(L-lysine) enhanced oligonucleotide uptake is seen in promyelocytic leukaemia (HL-60) cells and human melanoma (M-14) cells. Ginobbi et al. 1997. *Anticancer Res.* 17:29. In another example, liposomes coated with maleylated bovine serum albumin, folic acid, or ferric protoporphyrin IX, show enhanced cellular uptake of oligonucleotides in murine macrophages, KB cells, and 2.2.15 human hepatoma cells. Liang et al. 1999. *Pharmazie* 54:559-566.

Liposomes naturally accumulate in the liver, spleen, and reticuloendothelial system (so-called, passive targeting). By coupling liposomes to various ligands such as antibodies or protein A, they can be actively targeted to specific cell populations. For example, protein A-bearing liposomes may be pretreated with H-2K specific antibodies which are targeted to the mouse major histocompatibility complex-encoded H-2K protein expressed on L cells. (Vlassov et al. 1994. *Biochimica et Biophysica Acta* 1197:95-108).

V. Administration

The optimal course of administration or delivery of the oligonucleotides may vary depending upon the desired result and/or on the subject to be treated. As used herein "administration" refers to contacting cells with oligonucleotides and can be performed in vitro or in vivo. The dosage of oligonucleotides may be adjusted to optimally reduce expression of a protein translated from a target nucleic acid molecule, e.g., as measured by a readout of RNA stability or by a therapeutic response, without undue experimentation.

For example, expression of the protein encoded by the nucleic acid target can be measured to determine whether or not the dosage regimen needs to be adjusted accordingly. In addition, an increase or decrease in RNA or protein levels in a cell or produced by a cell can be measured using any art recognized technique. By determining whether transcription has been decreased, the effectiveness of the oligonucleotide in inducing the cleavage of a target RNA can be determined.

Any of the above-described oligonucleotide compositions can be used alone or in conjunction with a pharmaceutically acceptable carrier. As used herein, "pharmaceutically acceptable carrier" includes appropriate solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, it can be used in the therapeutic compositions. Supplementary active ingredients can also be incorporated into the compositions.

Oligonucleotides may be incorporated into liposomes or liposomes modified with polyethylene glycol or admixed with cationic lipids for parenteral administration. Incorporation of additional substances into the liposome, for example, antibodies reactive against membrane proteins found on specific target cells, can help target the oligonucleotides to specific cell types.

Moreover, the present invention provides for administering the subject oligonucleotides with an osmotic pump providing continuous infusion of such oligonucleotides, for example, as described in Rataiczak et al. (1992 *Proc. Natl. Acad. Sci. USA* 89:11823-11827). Such osmotic pumps are commercially available, e.g., from Alzet Inc. (Palo Alto, Calif.). Topical administration and parenteral administration in a cationic lipid carrier are preferred.

With respect to in vivo applications, the formulations of the present invention can be administered to a patient in a variety of forms adapted to the chosen route of administration, e.g., parenterally, orally, or intraperitoneally. Parenteral administration, which is preferred, includes administration by the following routes: intravenous; intramuscular; interstitially; intraarterially; subcutaneous; intra ocular; intrasynovial; trans epithelial, including transdermal; pulmonary via inhalation; ophthalmic; sublingual and buccal; topically, including ophthalmic; dermal; ocular; rectal; and nasal inhalation via insufflation.

Pharmaceutical preparations for parenteral administration include aqueous solutions of the active compounds in water-soluble or water-dispersible form. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, or dextran, optionally, the suspension may also contain stabilizers. The oligonucleotides of the invention can be formulated in liquid solutions, preferably in physiologically compatible buffers such as Hank's solution or Ringer's solution. In addition, the oligonucleotides may be formulated in solid form and redissolved or suspended immediately prior to use. Lyophilized forms are also included in the invention.

Pharmaceutical preparations for topical administration include transdermal patches, ointments, lotions, creams, gels, drops, sprays, suppositories, liquids and powders. In addition, conventional pharmaceutical carriers, aqueous, powder or oily bases, or thickeners may be used in pharmaceutical preparations for topical administration.

Pharmaceutical preparations for oral administration include powders or granules, suspensions or solutions in water or non-aqueous media, capsules, sachets or tablets. In addition, thickeners, flavoring agents, diluents, emulsifiers, dispersing aids, or binders may be used in pharmaceutical preparations for oral administration.

For transmucosal or transdermal administration, penetrants appropriate to the barrier to be permeated are used in the formulation. Such penetrants are known in the art, and include, for example, for transmucosal administration bile salts and fusidic acid derivatives, and detergents. Transmucosal administration may be through nasal sprays or using suppositories. For oral administration, the oligonucleotides are formulated into conventional oral administration forms such as capsules, tablets, and tonics. For topical administration, the oligonucleotides of the invention are formulated into ointments, salves, gels, or creams as known in the art.

Drug delivery vehicles can be chosen e.g., for in vitro, for systemic, or for topical administration. These vehicles can be designed to serve as a slow release reservoir or to deliver their contents directly to the target cell. An advantage of using some direct delivery drug vehicles is that multiple molecules are delivered per uptake. Such vehicles have been shown to increase the circulation half-life of drugs that would otherwise be rapidly cleared from the blood stream. Some examples of such specialized drug delivery vehicles which fall into this category are liposomes, hydrogels, cyclodextrins, biodegradable nanocapsules, and bioadhesive microspheres.

The described oligonucleotides may be administered systemically to a subject. Systemic absorption refers to the entry of drugs into the blood stream followed by distribution throughout the entire body. Administration routes which lead to systemic absorption include: intravenous, subcutaneous, intraperitoneal, and intranasal. Each of these administration routes delivers the oligonucleotide to accessible diseased cells. Following subcutaneous administration, the therapeutic agent drains into local lymph nodes and proceeds through the lymphatic network into the circulation. The rate of entry into the circulation has been shown to be a function of molecular weight or size. The use of a liposome or other drug carrier localizes the oligonucleotide at the lymph node. The oligonucleotide can be modified to diffuse into the cell, or the liposome can directly participate in the delivery of either the unmodified or modified oligonucleotide into the cell.

The chosen method of delivery will result in entry into cells. Preferred delivery methods include liposomes (10-400 nm), hydrogels, controlled-release polymers, and other pharmaceutically applicable vehicles, and microinjection or electroporation (for ex vivo treatments).

The pharmaceutical preparations of the present invention may be prepared and formulated as emulsions. Emulsions are usually heterogeneous systems of one liquid dispersed in another in the form of droplets usually exceeding 0.1 µm in diameter. The emulsions of the present invention may contain excipients such as emulsifiers, stabilizers, dyes, fats, oils, waxes, fatty acids, fatty alcohols, fatty esters, humectants, hydrophilic colloids, preservatives, and anti-oxidants may also be present in emulsions as needed. These excipients may be present as a solution in either the aqueous phase, oily phase or itself as a separate phase.

Examples of naturally occurring emulsifiers that may be used in emulsion formulations of the present invention include lanolin, beeswax, phosphatides, lecithin and acacia. Finely divided solids have also been used as good emulsifiers especially in combination with surfactants and in viscous preparations. Examples of finely divided solids that may be used as emulsifiers include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

Examples of preservatives that may be included in the emulsion formulations include methyl paraben, propyl paraben, quaternary ammonium salts, benzalkonium chloride, esters of p-hydroxybenzoic acid, and boric acid. Examples of antioxidants that may be included in the emulsion formulations include free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

In one embodiment, the compositions of oligonucleotides are formulated as microemulsions. A microemulsion is a system of water, oil and amphiphile which is a single optically isotropic and thermodynamically stable liquid solution. Typically microemulsions are prepared by first dispersing an oil in an aqueous surfactant solution and then adding a sufficient amount of a 4th component, generally an intermediate chain-length alcohol to form a transparent system.

Surfactants that may be used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (S0750), decaglycerol decaoleate (DA0750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules.

Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain ($C_8$-$C_{12}$) mono, di, and tri-glycerides, polyoxyethylated glyceryl fatty acid esters, fatty alcohols, polyglycolized glycerides, saturated polyglycolized $C_8$-$C_{10}$ glycerides, vegetable oils and silicone oil.

Microemulsions are particularly of interest from the standpoint of drug solubilization and the enhanced absorption of drugs. Lipid based microemulsions (both oil/water and water/oil) have been proposed to enhance the oral bioavailability of drugs.

Microemulsions offer improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11:1385; Ho et al., J. Pharm. Sci., 1996, 85:138-143). Microemulsions have also been effective in the transdermal delivery of active components in both cosmetic and pharmaceutical applications. It is expected that the microemulsion compositions and formulations of the present invention will facilitate the increased systemic absorption of oligonucleotides from the gastrointestinal tract, as well as improve the local cellular uptake of oligonucleotides within the gastrointestinal tract, vagina, buccal cavity and other areas of administration.

In an embodiment, the present invention employs various penetration enhancers to affect the efficient delivery of nucleic acids, particularly oligonucleotides, to the skin of animals. Even non-lipophilic drugs may cross cell membranes if the membrane to be crossed is treated with a penetration enhancer. In addition to increasing the diffusion of non-lipophilic drugs across cell membranes, penetration enhancers also act to enhance the permeability of lipophilic drugs.

Five categories of penetration enhancers that may be used in the present invention include: surfactants, fatty acids, bile salts, chelating agents, and non-chelating non-surfactants. Other agents may be utilized to enhance the penetration of the administered oligonucleotides include: glycols such as ethylene glycol and propylene glycol, pyrrols such as 2-15 pyrrol, azones, and terpenes such as limonene, and menthone.

The oligonucleotides, especially in lipid formulations, can also be administered by coating a medical device, for example, a catheter, such as an angioplasty balloon catheter, with a cationic lipid formulation. Coating may be achieved, for example, by dipping the medical device into a lipid formulation or a mixture of a lipid formulation and a suitable solvent, for example, an aqueous-based buffer, an aqueous solvent, ethanol, methylene chloride, chloroform and the like. An amount of the formulation will naturally adhere to the surface of the device which is subsequently administered to a patient, as appropriate. Alternatively, a lyophilized mixture of a lipid formulation may be specifically bound to the surface of the device. Such binding techniques are described, for example, in K. Ishihara et al., Journal of Biomedical Materials Research, Vol. 27, pp. 1309-1314 (1993), the disclosures of which are incorporated herein by reference in their entirety.

The useful dosage to be administered and the particular mode of administration will vary depending upon such factors as the cell type, or for in vivo use, the age, weight and the particular animal and region thereof to be treated, the particular oligonucleotide and delivery method used, the therapeutic or diagnostic use contemplated, and the form of the formulation, for example, suspension, emulsion, micelle or liposome, as will be readily apparent to those skilled in the art. Typically, dosage is administered at lower levels and increased until the desired effect is achieved. When lipids are used to deliver the oligonucleotides, the amount of lipid compound that is administered can vary and generally depends upon the amount of oligonucleotide agent being administered. For example, the weight ratio of lipid compound to oligonucleotide agent is preferably from about 1:1 to about 15:1, with a weight ratio of about 5:1 to about 10:1 being more preferred. Generally, the amount of cationic lipid compound which is administered will vary from between about 0.1 milligram (mg) to about 1 gram (g). By way of general guidance, typically between about 0.1 mg and about 10 mg of the particular oligonucleotide agent, and about 1 mg to about 100 mg of the lipid compositions, each per kilogram of patient body weight, is administered, although higher and lower amounts can be used.

The agents of the invention are administered to subjects or contacted with cells in a biologically compatible form suitable for pharmaceutical administration. By "biologically compatible form suitable for administration" is meant that the oligonucleotide is administered in a form in which any toxic effects are outweighed by the therapeutic effects of the oligonucleotide. In one embodiment, oligonucleotides can be administered to subjects. Examples of subjects include mammals, e.g., humans and other primates; cows, pigs, horses, and farming (agricultural) animals; dogs, cats, and other domesticated pets; mice, rats, and transgenic non-human animals.

Administration of an active amount of an oligonucleotide of the present invention is defined as an amount effective, at dosages and for periods of time necessary to achieve the desired result. For example, an active amount of an oligonucleotide may vary according to factors such as the type of cell, the oligonucleotide used, and for in vivo uses the disease state, age, sex, and weight of the individual, and the ability of the oligonucleotide to elicit a desired response in the individual. Establishment of therapeutic levels of oligonucleotides within the cell is dependent upon the rates of uptake and efflux or degradation. Decreasing the degree of degradation prolongs the intracellular half-life of the oligonucleotide. Thus, chemically-modified oligonucleotides, e.g., with modification of the phosphate backbone, may require different dosing.

The exact dosage of an oligonucleotide and number of doses administered will depend upon the data generated experimentally and in clinical trials. Several factors such as the desired effect, the delivery vehicle, disease indication, and the route of administration, will affect the dosage. Dosages can be readily determined by one of ordinary skill in the art and formulated into the subject pharmaceutical compositions. Preferably, the duration of treatment will extend at least through the course of the disease symptoms. Dosage regima may be adjusted to provide the optimum therapeutic response. For example, the oligonucleotide may be repeatedly administered, e.g., several doses may be administered daily or the dose may be proportionally reduced as indicated by the exigencies of the therapeutic situation. One of ordinary skill in the art will readily be able to determine appropriate doses and schedules of administration of the subject oligonucleotides, whether the oligonucleotides are to be administered to cells or to subjects.

VI. Therapeutic Use

By inhibiting the expression of a PCSK9 gene, the oligonucleotide compositions of the present invention can be used to treat any disease involving the expression of a PCSK9 protein. The inhibition of a PCSK9 gene includes any fragments and isoforms of PCSK9. Diseases that can be treated by oligonucleotide compositions in accordance with the present methods include, just to illustrate: metabolic diseases, traits, or conditions in a subject or organism. In one embodiment, the metabolic disease is selected from the group consisting of diabetis (e.g., type I and/or type II diabetis), insulin resistance, obesity, or related conditions, including but not limited to sleep apnea, hiatal hernia, reflux esophagisitis, osteoarthritis, gout, cancers associated with weight gain, gallstones, kidney stones, pulmonary hypertension, infertility, cardiovascular disease, above normal weight, and above normal lipid levels, uric acid levels, or oxalate levels.

Some specific examples of conditions that may benefit from the inhibition of PCSK9 include, for example, metabolic disorders, traits and conditions, including but not limited to hyperlipidemia, hypercholesterolemia, cardiovascular disease, atherosclerosis, hypertension, diabetes (e.g., type I and/or type II diabetis), insulin resistance, obesity and/or any other diseases, traits, and conditions that are related to PCSK9 gene expression or activity. Metabolic disorders, or metabolic syndrome, is described by accepted synonyms, which includes, but is not limited to, syndrome X, insulin resistance syndrome, insulin-resistant hypertension, the metabolic hypertensive syndrome, dysmetabolic syndrome, hyperlipidemia, hypercholesterolemia, cardiovascular disease, atherosclerosis, hypertension, diabetes (e.g., type I and/or type II diabetes), insulin resistance, and obesity. Components of the metabolic syndrome include, but is not limited to, glucose intolerance, impaired glucose tolerance, impaired fasting serum glucose, impaired fasting blood glucose, hyperinsulinemia, pre-diabetes, visceral obesity, hypertriglyceridemia, elevated serum concentrations of free fatty acids, elevated serum concentrations of C-reactive protein, elevated serum concentrations of lipoprotein(a), elevated serum concentrations of homocysteine, elevated serum concentrations of small, dense low-density lipoprotein (LDL)-cholesterol, elevated serum concentrations of lipoprotein-associated phospholipase (A2), reduced serum concentrations of high density lipoprotein (HDL)-cholesterol, reduced serum concentrations of HDL(2b)-cholesterol, reduced serum concentrations of adiponectin, adipogenesis, and albuminuria. Furthermore, the present disclosure may be beneficial and applies to any other diseases, traits, and conditions that are related to PCSK9 gene expression of activity.

In one embodiment, in vitro treatment of cells with oligonucleotides can be used for ex vivo therapy of cells removed from a subject (e.g., for treatment of leukemia or viral infection) or for treatment of cells which did not originate in the subject, but are to be administered to the subject (e.g., to eliminate transplantation antigen expression on cells to be transplanted into a subject). In addition, in vitro treatment of cells can be used in non-therapeutic settings, e.g., to evaluate gene function, to study gene regulation and protein synthesis or to evaluate improvements made to oligonucleotides designed to modulate gene expression or protein synthesis. In vivo treatment of cells can be useful in certain clinical settings where it is desirable to inhibit the expression of a protein. There are numerous medical conditions for which antisense therapy is reported to be suitable (see, e.g., U.S. Pat. No. 5,830,653) as well as respiratory syncytial virus infection (WO 95/22,553) influenza virus (WO 94/23,028), and malignancies (WO 94/08,003). Other examples of clinical uses of antisense sequences are reviewed, e.g., in Glaser. 1996. *Genetic Engineering News* 16:1. Exemplary targets for cleavage by oligonucleotides include, e.g., protein kinase Cα, ICAM-1, c-raf kinase, p53, c-myb, and the bcr/abl fusion gene found in chronic myelogenous leukemia.

The practice of the present invention will employ, unless otherwise indicated, conventional techniques of cell biology, cell culture, molecular biology, microbiology, recombinant DNA, and immunology, which are within the skill of the art. Such techniques are explained fully in the literature. See, for example, *Molecular Cloning A Laboratory Manual*, 2nd Ed., ed. by Sambrook, J. et al. (Cold Spring Harbor Laboratory Press (1989)); *Short Protocols in Molecular Biology*, 3rd Ed., ed. by Ausubel, F. et al. (Wiley, N.Y. (1995)); *DNA Cloning*, Volumes I and II (D. N. Glover ed., 1985); *Oligonucleotide Synthesis* (M. J. Gait ed. (1984)); Mullis et al. U.S. Pat. No. 4,683,195; *Nucleic Acid Hybridization* (B. D. Hames & S. J. Higgins eds. (1984)); the treatise, *Methods In Enzymology* (Academic Press, Inc., N.Y.); *Immunochemical Methods In Cell And Molecular Biology* (Mayer and Walker, eds., Academic Press, London (1987)); *Handbook Of Experimental Immunology*, Volumes I-IV (D. M. Weir and C. C. Blackwell, eds. (1986)); and Miller, J. *Experiments in Molecular Genetics* (Cold Spring Harbor Press, Cold Spring Harbor, N.Y. (1972)).

EXAMPLES

The invention now being generally described, it will be more readily understood by reference to the following examples, which are included merely for purposes of illustration of certain aspects and embodiments of the present invention, and are not intended to limit the invention. Although the examples below demonstrate silencing of PCSK9 using a select number of siRNA duplexes having particular chemistry, it is understood that any of the RNA chemistry described herein may be applied for the present methods.

Example 1

RNA Screen to Identify Lead Sequences within PCSK9

HeLaS3 cells were transfected at 0.1 nM active RNA concentration. Target mRNA was measured 48 hours post-transfection using the methods described below. Four duplexes: duplex 1 (corresponding to SEQ ID NOs:11 and 12), duplex 2 (corresponding to SEQ ID NOs:19 and 20), duplex 3 (corresponding to SEQ ID NOs:23 and 24) and duplex 4 (corresponding to SEQ ID NOs:25 and 26) were chosen as lead hits based on their activity, seed complement frequency (SCF), and homology to the mouse PCSK9 gene, as described below.

All duplexes used in the examples described herein are modified on the sense strand, but not on the antisense (guide) strand. The sense strands have been modified to include 2'OMe on 12 of the 5'-most end nucleotides and on 10 of the 3'-most nucleotides. The antisense strand complements the sense strand to form a blunt-ended duplex of 25 base-pairs.

Transfections were performed in HeLaS3 cells using LIPOFECTAMINE™ RNAiMax (Invitrogen) following the manufacture's procedures. In all studies, duplex candidates were co-transfected with non-targeting Luciferase control siRNA (Invitrogen) to a constant total concentration of 25 nM to allow for efficient complexing of the siRNAs and LIPOFECTAMINE™ RNAiMAX. Target mRNA levels were measured using a bDNA assay (Panomics QUANTI-GENE®) 48 hours post-transfection. In this assay, PCSK9 mRNA was normalized to Cyclophilin B (PPIB) mRNA.

The bDNA assay is a sandwich nucleic acid hybridization method that uses bDNA molecules to amplify signal from captured target RNA. According to the manufacturer, bDNA technology forms the basis of the FDA-approved clinical diagnostic VERSANT 3.0 assays for HIV, HCV and HBV viral load, that are offered commercially by Siemens and have been in use for over a decade. Another advantage of bDNA assays is that RNA is measured directly from the sample source, without RNA purification or enzymatic manipulation, thereby avoiding inefficiencies and variability introduced by or errors inherent to these processes.

The results were plotted and are shown in FIG. 1, which depicts the entire length of the PCSK9 gene. Each bar represents the silencing efficacy of a particular 25 base pair siRNA duplex which targets a region on PCSK9. It was found, for example, that duplex sequences spanning the positions 1035~1052 of PCSK9 are effective silencers. Generally, duplexes which effectively reduced target mRNA expression by more than 60% at a 0.1 nM dose were selected, which are listed in Table 1. However, sequences having low to moderate SCF are preferred, though not necessary, for the purpose of reducing potential off-targeting effects, as confirmed bioinformatically by Anderson et al. Additionally, to allow ease of pre-clinical testing in mice, sequences that lie in regions that share high sequence homology between human and mouse sequences (e.g, those that are at least 90% homologous to the corresponding mouse sequence) are preferable.

Interestingly, sequences derived by public algorithms predicted to be silencing sequences were found to be inactive in our assays, which demonstrates the need for experimental testing to identify actual silencing sequences. For example, the sequence beginning at position 3143 of human PCSK9 CAGAGGAAGAAACCUGGAACCAGAG (SEQ ID NO:92) as well as the sequence beginning at position 3180 CCAAGCUCACACAGCAGGAACUGAG (SEQ ID NO:93) were each predicted, by public algorithms, to be effective silencing sequences. However, these sequences were in fact found to be inactive.

TABLE 1

Sequences that effectively reduced target mRNA expression by more than 60% at 0.1 nM in initial screen.

| Start Site | Sense Sequence (5'-3') | AntiSense Sequence (5'-3') | <40% expression remaining at 0.1 nM | Seed region freq. |
|---|---|---|---|---|
| 246 | GCCUCUAGGUCUCCUCGCCAGGACA (SEQ ID NO: 1) | UGUCCUGGCGAGGAGACCUAGAGGC (SEQ ID NO: 2) | Yes (18.51%) | 5382 |
| 255 | AGAGGUUGCUGUCCUGGCGAGGAGA (SEQ ID NO: 3) | UCUCCUCGCCAGGACAGCAACCUCU (SEQ ID NO: 4) | Yes (20.14%) | 6649 |
| 834 | GGUGUAUCUCCUAGACACCAGCAUA (SEQ ID NO: 5) | UAUGCUGGUGUCUAGGAGAUACACC (SEQ ID NO: 6) | Yes (24.25%) | 5860 |
| 842 | UCACUCUGUAUGCUGGUGUCUAGGA (SEQ ID NO: 7) | UCCUAGACACCAGCAUACAGAGUGA (SEQ ID NO: 8) | Yes (39.76%) | 3676 |
| 891 | CACAUUCUCGAAGUCGGUGACCAUG (SEQ ID NO: 9) | CAUGGUCACCGACUUCGAGAAUGUG (SEQ ID NO: 10) | Yes (34.58%) | 3724 |
| 944 | GACAGGCCAGCAAGUGUGACAGUCA (SEQ ID NO: 11) | UGACUGUCACACUUGCUGGCCUGUC (SEQ ID NO: 12) | Yes (13.80%) | 4091 |
| 945 | ACAGGCCAGCAAGUGUGACAGUCAU (SEQ ID NO: 13) | AUGACUGUCACACUUGCUGGCCUGU (SEQ ID NO: 14) | Yes (13.95%) | 5161 |
| 946 | CAGGCCAGCAAGUGUGACAGUCAUG (SEQ ID NO: 15) | CAUGACUGUCACACUUGCUGGCCUG (SEQ ID NO: 16) | Yes (18.39%) | 4766 |
| 949 | GCCAGCAAGUGUGACAGUCAUGGCA (SEQ ID NO: 17) | UGCCAUGACUGUCACACUUGCUGGC (SEQ ID NO: 18) | Yes (17.92%) | 4819 |
| 1035 | CAGCCUGCGCGUGCUCAACUGCCAA (SEQ ID NO: 19) | UUGGCAGUUGAGCACGCGCAGGCUG (SEQ ID NO: 20) | Yes (34.50%) | 7591 |
| 1085 | UCAUAGGCCUGGAGUUUAUUCGGAA (SEQ ID NO: 21) | UUCCGAAUAAACUCCAGGCCUAUGA (SEQ ID NO: 22) | Yes (12.40%) | 1002 |
| 1086 | CAUAGGCCUGGAGUUUAUUCGGAAA (SEQ ID NO: 23) | UUUCCGAAUAAACUCCAGGCCUAUG (SEQ ID NO: 24) | Yes (26.62%) | 1049 |
| 1352 | AAGAGGUCCACACAGCGGCCAAAGU (SEQ ID NO: 25) | ACUUUGGCCGCUGUGUGGACCUCUU (SEQ ID NO: 26) | Yes (18.66%) | 6941 |
| 2702 | AUGCCUGGCACGGAACAAGAGCUCA (SEQ ID NO: 27) | UGAGCUCUUGUUCCGUGCCAGGCAU (SEQ ID NO: 28) | Yes (39.86%) | 4539 |
| 2710 | AGGAUUGAAUGCCUGGCACGGAACA (SEQ ID NO: 29) | UGUUCCGUGCCAGGCAUUCAAUCCU (SEQ ID NO: 30) | Yes (30.82%) | 805 |
| 2728 | CAAUCCUCAGGUCUCCACCAAGGAG (SEQ ID NO: 31) | CUCCUUGGUGGAGACCUGAGGAUUG (SEQ ID NO: 32) | Yes (37.10%) | 5872 |
| 2901 | GCUUUCUGGAUGGCAUCUAGCCAGA (SEQ ID NO: 33) | UCUGGCUAGAUGCCAUCCAGAAAGC (SEQ ID NO: 34) | Yes (28.77%) | 7443 |
| 2974 | CCUGAGCCACCUUUACUCUGCUCUA (SEQ ID NO: 35) | UAGAGCAGAGUAAAGGUGGCUCAGG (SEQ ID NO: 36) | Yes (32.34%) | 6734 |
| 2992 | UGCUAGCACAGCCUGGCAUAGAGCA (SEQ ID NO: 37) | UGCUCUAUGCCAGGCUGUGCUAGCA (SEQ ID NO: 38) | Yes (34.83%) | 3198 |
| 3192 | AGCAGGAACUGAGCCAGAAACGCAG (SEQ ID NO: 39) | CUGCGUUUCUGGCUCAGUUCCUGCU (SEQ ID NO: 40) | Yes (22.51%) | 1054 |
| 3303 | GAACACAGACCAGGAAGCUCGGUGA (SEQ ID NO: 41) | UCACCGAGCUUCCUGGUCUGUGUUC (SEQ ID NO: 42) | Yes (15.77%) | 1195 |
| 3319 | AUCGUUCUGCCAUCACUCACCGAGC (SEQ ID NO: 43) | GCUCGGUGAGUGAUGGCAGAACGAU (SEQ ID NO: 44) | Yes (35.72%) | 1402 |
| 3337 | AGUUCCAUGCCUGCAGGCAUCGUUC (SEQ ID NO: 45) | GAACGAUGCCUGCAGGCAUGGAACU (SEQ ID NO: 46) | Yes (29.83%) | 1051 |
| 3389 | ACUGGCCUGGCGGAGAUGCUUCUAA (SEQ ID NO: 47) | UUAGAAGCAUCUCCGCCAGGCCAGU (SEQ ID NO: 48) | Yes (33.07%) | 5063 |

TABLE 1-continued

Sequences that effectively reduced target mRNA expression by more than 60% at 0.1 nM in initial screen.

| Start Site | Sense Sequence (5'-3') | AntiSense Sequence (5'-3') | <40% expression remaining at 0.1 nM | Seed region freq. |
|---|---|---|---|---|
| 3393 | GCCUGGCGGAGAUGCUUCUAAGGCA (SEQ ID NO: 49) | UGCCUUAGAAGCAUCUCCGCCAGGC (SEQ ID NO: 50) | Yes (29.92%) | 2866 |
| 3394 | AUGCCUUAGAAGCAUCUCCGCCAGG (SEQ ID NO: 51) | CCUGGCGGAGAUGCUUCUAAGGCAU (SEQ ID NO: 52) | Yes (34.49%) | 1844 |

Example 2

$EC_{50}$ Analysis of siRNA Duplexes Based Off of Lead Duplex Sequences (Duplexes 1-4)

$EC_{50}$ analyses were performed with duplexes whose sequences are based off of select duplexes from Example 1 (i.e., duplexes 1-4). In the RNA screen above, duplexes which effectively reduced target mRNA expression by more than 60% at a 0.1 nM dose were used to design and test additional duplexes. Additional selection factors are described in Example 1. The additional sequences derived from the initial selected sequences are shown in Table 2, and the efficacy of each duplex is presented below. Table 2 compares each human sequence to the corresponding mouse sequence; mismatches, if any, are underlined and bolded in the mouse sequence.

Figure 2A:
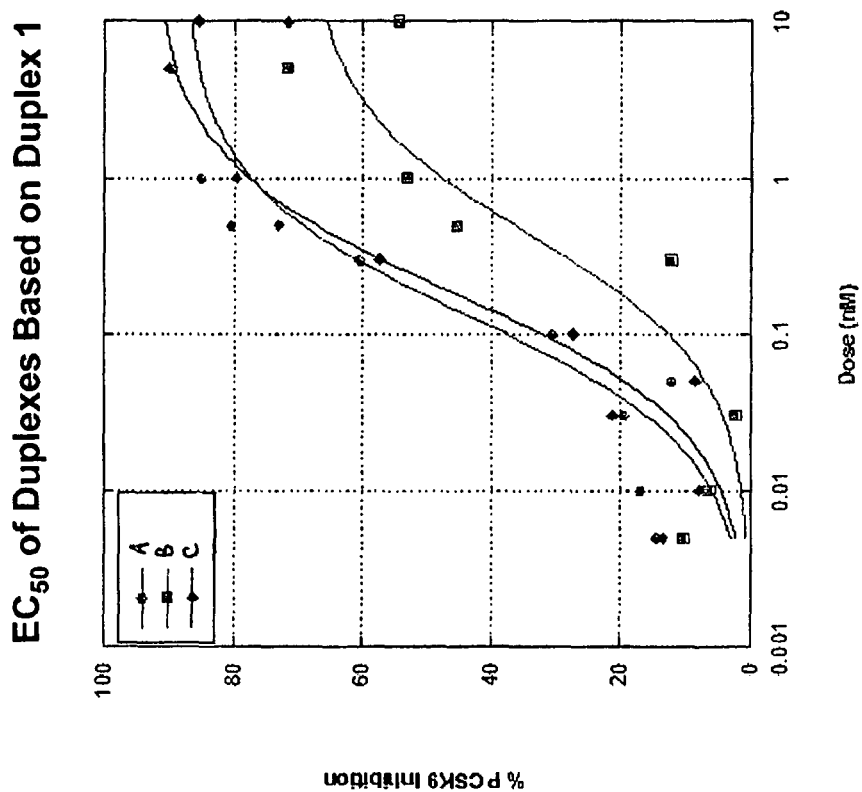
FIG. 2A shows an $EC_{50}$ analysis of PCSK9 siRNA duplexes that recognize target sequences corresponding to SEQ ID NO:53 (indicated as "A"), SEQ ID NO:55 (indicated as "B") and SEQ ID NO:57 (indicated as "C"), based off of sequences surrounding the duplex 1 site identified in the RNA screen. PCSK9 expression was measured using a bDNA hybridization assay (Panomics) 48 hours post-transfection.

FIG. 2A shows the results of duplexes that are based off of duplex 1. These duplexes recognize target sequences that correspond to SEQ ID NOs:53, 55 and 57 (see Table 2 below). PCSK9 expression was measured using cDNA hybridization assay as described above at 48 hours post-transfection. The average $EC_{50}$ values of these duplexes are as follows:

SEQ ID NO:53: 0.133 nM±0.045 nM
SEQ ID NO:55: 0.438 nM±0.230 nM
SEQ ID NO:57: 0.187 nM±0.043 nM

Figure 2B:
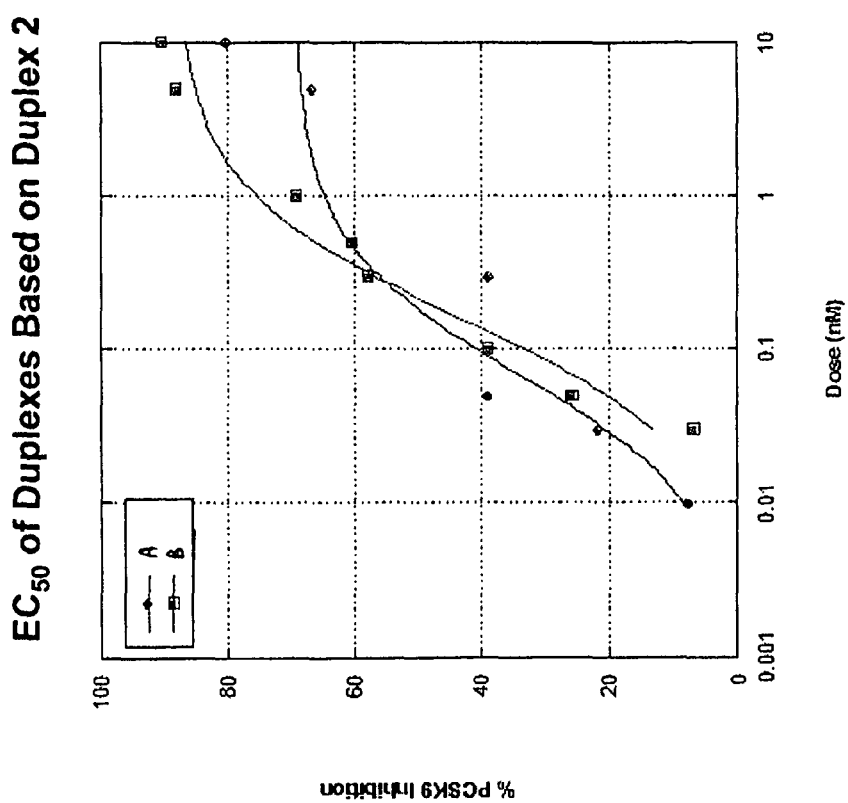
FIG. 2B shows an $EC_{50}$ analysis of PCSK9 siRNA duplexes that recognize target sequences corresponding to SEQ ID NO:59 (indicated as "A") and SEQ ID NO:61 (indicated as "B") based off of sequences surrounding the duplex 2 site identified in the RNA screen. PCSK9 expression was measured using a bDNA hybridization assay (Panomics) 48 hours post-transfection.

FIG. 2B shows the results of duplexes that are based off of duplex 2. These duplexes recognize target sequences that correspond to SEQ ID NOs:59 and 61 (see Table 2 below). PCSK9 expression was measured using cDNA hybridization assay as described above at 48 hours post-transfection. The average $EC_{50}$ values of these duplexes are as follows:

SEQ ID NO:59: 0.070 nM±0.35 nM
SEQ ID NO:61: 0.164 nM±0.032 nM

Figure 2C:
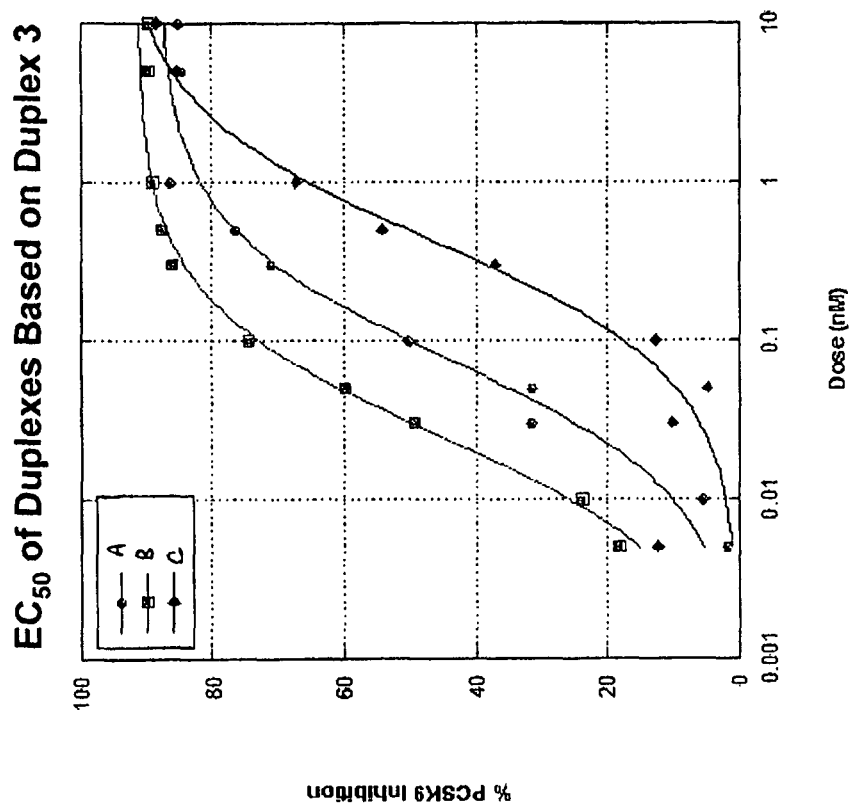
FIG. 2C shows an $EC_{50}$ analysis of PCSK9 siRNA duplexes that recognize target sequences corresponding to SEQ ID NO:63 (indicated as "A"), SEQ ID NO:65 (indicated as "B") and SEQ ID NO:66 (indicated as "C") based off of sequences surrounding the duplex 3 site identified in the RNA screen. PCSK9 expression was measured using a bDNA hybridization assay (Panomics) 48 hours post-transfection.

FIG. 2C shows the results of duplexes that are based off of duplex 3. These duplexes recognize target sequences that correspond to SEQ ID NOs:63, 65 and 66(see Table 2 below). PCSK9 expression was measured using cDNA hybridization assay as described above at 48 hours post-transfection. The average $EC_{50}$ values of these duplexes are as follows:

SEQ ID NO:63: 0.075 nM±0.009 nM
SEQ ID NO:65: 0.025 nM±0.001 nM
SEQ ID NO:66: 0.428 nM±0.076 nM

Figure 2D:
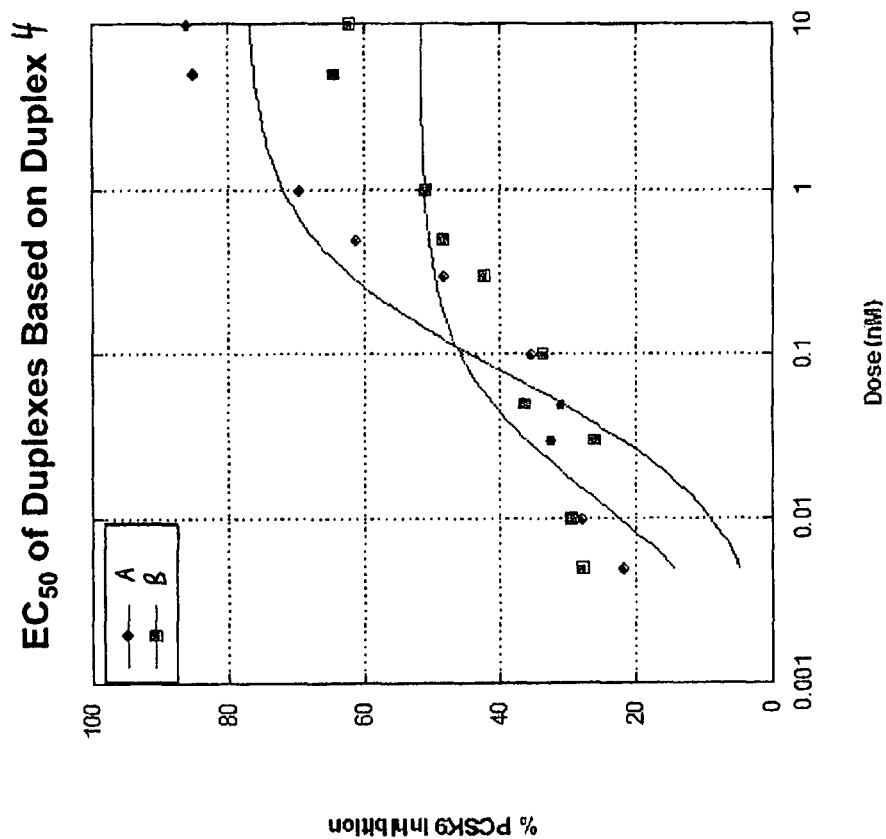
FIG. 2D shows an $EC_{50}$ analysis of PCSK9 siRNA duplexes that recognize target sequences corresponding to SEQ ID NO:67 (indicated as "A") and SEQ ID NO:69 (indicated as "B") based off of sequences surrounding the duplex 4 site identified in the RNA screen. PCSK9 expression was measured using a bDNA hybridization assay (Panomics) 48 hours post-transfection.

FIG. 2D shows the results of duplexes that are based off of duplex 4. These duplexes recognize target sequences that correspond to SEQ ID NOs:67 and 69(see Table 2 below). PCSK9 expression was measured using cDNA hybridization assay as described above at 48 hours post-transfection. The average $EC_{50}$ values of these duplexes are as follows:

SEQ ID NO:67: 0.075 nM±0.032 nM
SEQ ID NO:69: 0.013 nM±0.007 nM

TABLE 2

Additional sequences derived from duplexes 1-4 selected based on initial RNA screen.

| Start Site (H) | Human Sense Sequence (5'-3') | Start Site (M) | Homology to Mouse | Seed region freq. | AVG $EC_{50}$ Value (nM) |
|---|---|---|---|---|---|
| 944 | GACAGGCCAGCAAGTGTGACAGTCA (SEQ ID NO: 53) human GACAGGCGAGCAAGTGTGACAGCCA (SEQ ID NO: 54) mouse | 1077 | 92% (2 MM, 1 in seed) | 4091 | 0.133 |
| 942 | CAGACAGGCCAGCAAGTGTGACAGT (SEQ ID NO: 55) human CAGACAGGCGAGCAAGTGTGACAGC (SEQ ID NO: 56) mouse | 1075 | 92% (2 MM in non-seed) | 5754 | 0.438 |
| 941 | ACAGACAGGCCAGCAAGTGTGACAG (SEQ ID NO: 57) human ACAGACAGGCGAGCAAGTGTGACAG (SEQ ID NO: 58) mouse | 1074 | 96% (1 MM in non-seed) | 5052 | 0.187 |
| 1031 | TGCGCAGCCTGCGCGTGCTCAACTG (SEQ ID NO: 59) human TGCACAGCCTGCGTGTGCTCAACTG (SEQ ID NO: 60) mouse | 1164 | 92% (2 MM in non-seed) | 4138 | 0.070 |

TABLE 2-continued

Additional sequences derived from duplexes 1-4 selected based on initial RNA screen.

| Start Site (H) | Human Sense Sequence (5'-3') | Start Site (M) | Homology to Mouse | Seed region freq. | AVG EC$_{50}$ Value (nM) |
|---|---|---|---|---|---|
| 1040 | TGCGCGTGCTCAACTGCCAAGGGAA (SEQ ID NO: 61) human<br>TGCGTGTGCTCAACTGTCAAGGGAA (SEQ ID NO: 62) mouse | 1173 | 92% (2 MM in non-seed) | 6442 | 0.164 |
| 1086 | CATAGGCCTGGAGTTTATTCGGAAA (SEQ ID NO: 63) human<br>CATAGGCCTGGAGTTTATTCGGAAG (SEQ ID NO: 64) mouse | 1219 | 96% (1 MM in non-seed) | 1049 | 0.075 |
| 1085 | TCATAGGCCTGGAGTTTATTCGGAA (SEQ ID NO: 65) human<br>TCATAGGCCTGGAGTTTATTCGGAA (SEQ ID NO: 65) mouse | 1218 | 100 | 1002 | 0.025 |
| 1084 | CTCATAGGCCTGGAGTTTATTCGGA (SEQ ID NO: 66) human<br>CTCATAGGCCTGGAGTTTATTCGGA (SEQ ID NO: 66) mouse | 1217 | 100 | 762 | 0.428 |
| 1353 | CTTTGGCCGCTGTGTGGACCTCTTT (SEQ ID NO: 67) human<br>TTTTGGACGCTGTGTGGATCTCTTT (SEQ ID NO: 68) mouse | 1486 | 88% (3 MM, 1 in seed) | 7262 | 0.075 |
| 1354 | TTTGGCCGCTGTGTGGACCTCTTTG (SEQ ID NO: 69) human<br>TTTGGACGCTGTGTGGATCTCTTTG (SEQ ID NO: 70) mouse | 1487 | 92% (2 MM in non-seed) | 8082 | 0.013 |
| 940 | CACAGACAGGCCAGCAAGTGTGACA (SEQ ID NO: 71) human<br>CACAGACAGGCGAGCAAGTGTGACA (SEQ ID NO: 72) mouse | 1079 | 96% (1 MM in non-seed) | 5549 | 2.13 |
| 939 | CCACAGACAGGCCAGCAAGTGTGAC (SEQ ID NO: 73) human<br>CCACAGACAGGCGAGCAAGTGTGAC (SEQ ID NO: 74) mouse | 1072 | 96% (1 MM in non-seed) | 5788 | 4.36 |
| 1030 | ATGCGCAGCCTGCGCGTGCTCAACT (SEQ ID NO: 75) human<br>CTGCACAGCCTGCGTGTGCTCAACT (SEQ ID NO: 76) mouse | 1163 | 88% (2 MM in non-seed) | 3443 | 1.17 |
| 1083 | CCTCATAGGCCTGGAGTTTATTCGG (SEQ ID NO: 77) human<br>CCTCATAGGCCTGGAGTTTATTCGG (SEQ ID NO: 77) mouse | 1216 | 100 | 683 | 1.00 |
| 1355 | TTGGCCGCTGTGTGGACCTCTTTGC (SEQ ID NO: 78) human<br>TTGGACGCTGTGTGGATCTCTTTGC (SEQ ID NO: 79) mouse | 1488 | 92% (2 MM in non-seed) | 7934 | 1.17 |

"Start Site (H)" and "Start Site (M)" indicate the starting position of each sequence in the human or mouse PCSK9, respectively.

Example 3

EC$_{50}$ Comparison of Lead siRNA Duplexes Selected for Future Studies

Figure 3:
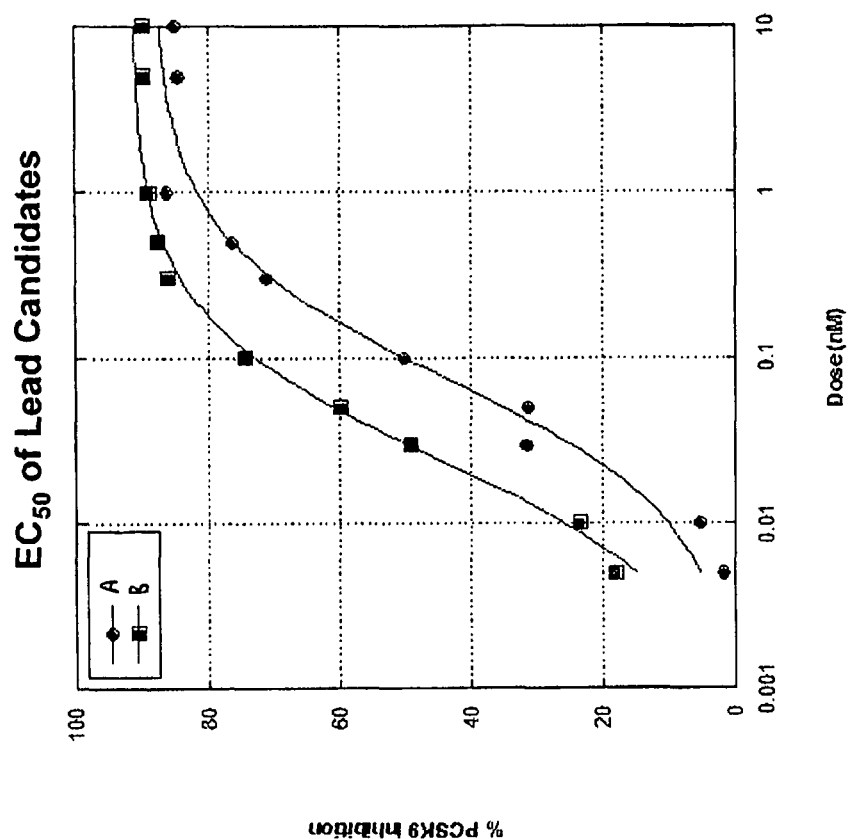
FIG. 3 shows an $EC_{50}$ analysis of two lead PCSK9 duplexes that recognize target sequences corresponding to SEQ ID NO:63 (indicated as "A") and SEQ ID NO:65 (indicated as "B"). PCSK9 expression was measured using a bDNA hybridization assay (Panomics) 48 hours post-transfection.

Two lead duplexes that recognize target sequences corresponding to SEQ ID NOs:63 and 65 were selected for future studies in mice. A side-by-side comparison of their EC$_{50}$ is shown in FIG. 3. The assay conditions for this analysis are similar to those described in Examples 1 and 2. The EC$_{50}$ values of these duplexes are as follows:

SEQ ID NO:63: 0.075 nM±0.009 nM
SEQ ID NO:65: 0.025 nM±0.001 nM

The average EC$_{50}$ values for all duplexes evaluated in Examples 2 and 3 are shown in Table 2.

Example 4

Optimization of RNAi Molecules sd-rxRNA molecules were generated targeting PCSK9. Target sequences included SEQ ID NOs:94, 96, 98 and 100. The sense and antisense strands of sd-rxRNA molecules were modified to optimize silencing. Examples of unmodified sense strand sequences correspond to SEQ ID NOs:94, 96, 98 and 100. Examples of unmodified antisense strand sequences correspond to SEQ ID NOs:95, 97, 99 and 101. Table 3 presents examples of modified sense and antisense strand sequences. Modifications include addition of methyl groups, referred to as "m," conjugation to a cholesterol group, referred to as "chol," addition of a 5' phosphate group, referred to as "5'-P," addition of a fluoro group, referred to as "F" or "f" and addition of a phosphorothioate linkage, referred to as "*".

TABLE 3

Optimized sd-rxRNA molecules

| Sense strand | Guide strand | % Silencing | EC50 (nM) |
|---|---|---|---|
| AGmUmUmUAmUmUmCGGAA-chol (SEQ ID NO: 84) | 5'-P-mU(2'-F-U)(2'-F-C)(2'-F-C)GAA(2'-F-U)AAAfCfU*fC*fC*A*G*G*C (SEQ ID NO: 85) | 70% | 0.025 |
| mCAAGmUGmUGAmCAGmU-chol (SEQ ID NO: 86) | 5'-P-mA(2'-F-C)(2'-F-U)G(2'-F-U)(2'-F-C)A(2'-F-C)A(2'-F-C)fUfUG*fC*fU*G*G*fC*C (SEQ ID NO: 87) | 50% | 0.438 |
| GGAGmUmUAmUmUmCGGAA-chol (SEQ ID NO: 88) | 5'-P-mU(2'-F-U)(2'-F-C)(2'-F-C)GAA(2'-F-U)AAAfCfU*fC*fC*A*G*G*C (SEQ ID NO: 89) | 72% | |
| mCAAGmUGmUGAmCAGmUmCA-chol (SEQ ID NO: 90) | 5'-P-mUGA(2'-F-C)(2'-F-U)G(2'-F-U)(2'-F-C)A(2g-F-C)AfCfU*fU*G*fC*fU*G*G (SEQ ID NO: 91) | 53% | |

Figure 4:
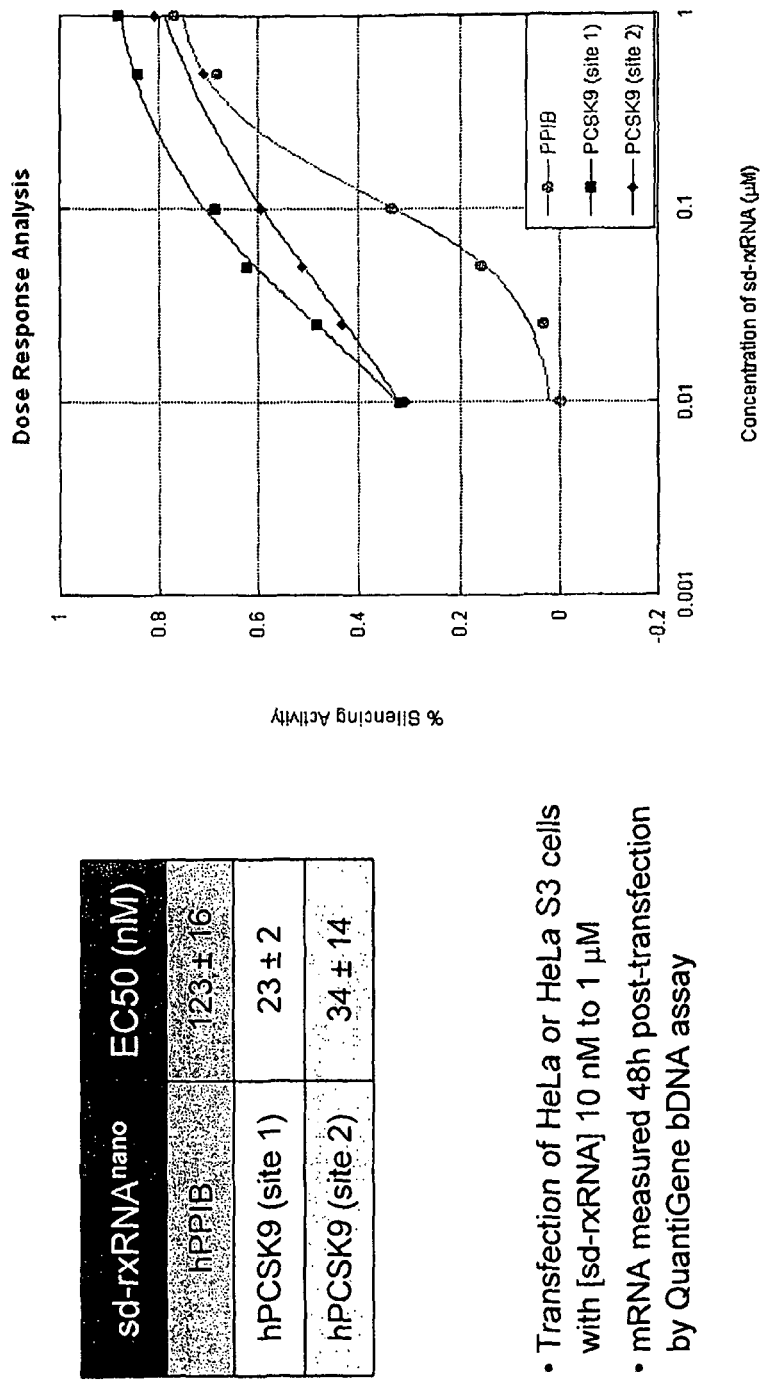
FIG. 4 shows a dose-response curve indicating silencing of PCSK9 expression achieved through transfection of HeLa or HeLa S3 cells with sd-rxRNA.

A dose-response experiment was performed in which HeLa S3 cells (ATCC, Manassas, Va.) were transfected using passive uptake transfection (in the absence of a delivery vehicle) with sd-rxRNAs targeting PCSK9 at varying concentrations in Accell Media (Dharmacon, Lafayette, Colo.). 48 hrs post transfection, cells were lysed and mRNA levels were determined using the Quantigene bDNA assay (Panomics, Fremont, Calif.) according to manufacturer's instructions. Data were normalized to a luciferase targeting control sd-rxRNA. Data from this dose-response experiment is presented in FIG. 4 indicating potent gene silencing using sd-rxRNA molecules to target PCSK9.

The invention claimed is:

1. An RNAi construct for inhibiting expression of a PCSK9 gene, comprising a double-stranded RNA (dsRNA) construct of 25-27 base pairs in length, the dsRNA comprising: (1) a sense strand having a 5'-end and a 3'-end, wherein the sense strand comprises SEQ ID NO: 59, and wherein the sense strand comprises 12-14 and 10-12 consecutive 2'-modified ribose sugars at the 5'-end and the 3'-end nucleotides, respectively, and (2) an antisense strand having a 5'-end and a 3'-end, which hybridizes to the sense strand.

2. The RNAi construct of claim 1, wherein the RNAi construct comprises one or more hydrophobic modifications.

3. The RNAi construct of claim 1, wherein the double stranded RNA (dsRNA) construct is 25 or 26 nucleotides in length.

4. A composition comprising the RNAi construct of claim 1, and a pharmaceutically acceptable carrier or diluent.

5. A method for inhibiting the expression of a PCSK9 gene in a mammalian cell, comprising contacting the mammalian cell with the RNAi construct of claim 1.

6. An RNAi construct for inhibiting expression of a PCSK9 gene, comprising a double-stranded RNA (dsRNA) construct of 2-27 base pairs in length, the dsRNA comprising: (1) a sense strand having a 5'-end and a 3'-end, wherein the sense strand comprises SEQ ID NO: 67 or 69, and wherein the sense strand comprises 12-14 and 10-12 consecutive 2'-modified ribose sugars at the 5'-end and the 3'-end nucleotides, respectively, and (2) an antisense strand having a 5'-end and a 3'-end, which hybridizes to the sense strand.

7. The RNAi construct of claim 6, wherein the RNAi construct comprises one or more hydrophobic modifications.

8. The RNAi construct of claim 6, wherein the double stranded RNA (dsRNA) construct is 25 or 26 nucleotides in length.

9. A composition comprising the RNAi construct of claim 6, and a pharmaceutically acceptable carrier or diluent.

10. A method for inhibiting the expression of a PCSK9 gene in a mammalian cell, comprising contacting the mammalian cell with the RNAi construct of claim 6.

* * * * *

UNITED STATES PATENT AND TRADEMARK OFFICE
CERTIFICATE OF CORRECTION

| | |
|---|---|
| PATENT NO. | : 9,493,774 B2 |
| APPLICATION NO. | : 13/143275 |
| DATED | : November 15, 2016 |
| INVENTOR(S) | : Joanne Kamens et al. |

It is certified that error appears in the above-identified patent and that said Letters Patent is hereby corrected as shown below:

On the Title Page

Assignee: In the address of the Assignee, "Marlsborough, MA (US)" should be replaced to read --Marlborough, MA (US)--

In the Claims

In Claim 6, at Column 104, Line 29: "construct of 2-27base pairs in length" should be replaced to read --construct of 25-27 base pairs in length--

Signed and Sealed this
Fourth Day of April, 2017

Michelle K. Lee
*Director of the United States Patent and Trademark Office*

SEQUENCE LISTING

<160> NUMBER OF SEQ ID NOS: 101

<210> SEQ ID NO 1
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 1
gccucuaggu cuccucgcca ggaca                25

<210> SEQ ID NO 2
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 2
uguccuggcg aggagaccua gaggc                25

<210> SEQ ID NO 3
<211> LENGTH: 25

```
<212> TYPE: RNA
<213> ORGANISM: Artificial sequence
<220> FEATURE:
<223> OTHER INFORMATION: Synthetic oligonucleotide

<400> SEQUENCE: 3
agagguugcu guccuggcga ggaga                                          25

<210> SEQ ID NO 4
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 4
ucuccucgcc aggacagcaa ccucu                                          25

<210> SEQ ID NO 5
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 5
gguguaucuc cuagacacca gcaua                                          25

<210> SEQ ID NO 6
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 6
uaugcuggug ucuaggagau acacc                                          25

<210> SEQ ID NO 7
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 7
ucacucugua ugcugguguc uagga                                          25

<210> SEQ ID NO 8
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 8
uccuagacac cagcauacag aguga                                          25

<210> SEQ ID NO 9
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 9
```

```
cacauucucg aagucgguga ccaug                                              25

<210> SEQ ID NO 10
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 10
cauggucacc gacuucgaga augug                                              25

<210> SEQ ID NO 11
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 11
gacaggccag caagugugac aguca                                              25

<210> SEQ ID NO 12
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 12
ugacugucac acuugcuggc cuguc                                              25

<210> SEQ ID NO 13
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 13
acaggccagc aagugugaca gucau                                              25

<210> SEQ ID NO 14
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 14
augacuguca cacuugcugg ccugu                                              25

<210> SEQ ID NO 15
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 15
caggccagca agugugacag ucaug                                              25

<210> SEQ ID NO 16
<211> LENGTH: 25
<212> TYPE: RNA
<213> ORGANISM: Artificial sequence
```

```
<220> FEATURE:
<223> OTHER INFORMATION: Synthetic oligonucleotide

<400> SEQUENCE: 16
caugacuguc acacuugcug gccug                                              25

<210> SEQ ID NO 17
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 17
gccagcaagu gugacaguca uggca                                              25

<210> SEQ ID NO 18
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 18
ugccaugacu gucacacuug cuggc                                              25

<210> SEQ ID NO 19
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 19
cagccugcgc gugcucaacu gccaa                                              25

<210> SEQ ID NO 20
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 20
uuggcaguug agcacgcgca ggcug                                              25

<210> SEQ ID NO 21
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 21
ucauaggccu ggaguuuauu cggaa                                              25

<210> SEQ ID NO 22
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 22
uuccgaauaa acuccaggcc uauga                                              25
```

```
<210> SEQ ID NO 23
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 23
cauaggccug gaguuuauuc ggaaa                                              25

<210> SEQ ID NO 24
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 24
uuuccgaaua aacuccaggc cuaug                                              25

<210> SEQ ID NO 25
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 25 aagagguccea cacagcggcc aaagu                                             25

<210> SEQ ID NO 26
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 26
acuuuggccg cuguguggac cucuu                                              25

<210> SEQ ID NO 27
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 27
augccuggca cggaacaaga gcuca                                              25

<210> SEQ ID NO 28
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 28
ugagcucuug uuccgugcca ggcau                                              25

<210> SEQ ID NO 29
<211> LENGTH: 25
<212> TYPE: RNA
<213> ORGANISM: Artificial sequence
<220> FEATURE:
<223> OTHER INFORMATION: Synthetic oligonucleotide
```

<400> SEQUENCE: 29
aggauugaau gccuggcacg gaaca                                          25

<210> SEQ ID NO 30
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 30 uguccgugc caggcauuca auccu                                           25

<210> SEQ ID NO 31
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 31
caauccucag gucuccacca aggag                                          25

<210> SEQ ID NO 32
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 32
cuccuuggug gagaccugag gauug                                          25

<210> SEQ ID NO 33
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 33
gcuuucugga uggcaucuag ccaga                                          25

<210> SEQ ID NO 34
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 34
ucuggcuaga ugccauccag aaagc                                          25

<210> SEQ ID NO 35
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 35
ccugagccac cuuuacucug cucua                                          25

<210> SEQ ID NO 36

```
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 36
uagagcagag uaaagguggc ucagg                                              25

<210> SEQ ID NO 37
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 37
ugcuagcaca gccuggcaua gagca                                              25

<210> SEQ ID NO 38
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 38
ugcucuaugc caggcugugc uagca                                              25

<210> SEQ ID NO 39
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 39
agcaggaacu gagccagaaa cgcag                                              25

<210> SEQ ID NO 40
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 40
cugcguuucu ggcucaguuc cugcu                                              25

<210> SEQ ID NO 41
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 41
gaacacagac caggaagcuc gguga                                              25

<210> SEQ ID NO 42
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 42
```
ucaccgagcu uccggucug uguuc                                         25

<210> SEQ ID NO 43
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 43
aucguucugc caucacucac cgagc                                        25

<210> SEQ ID NO 44
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 44
gcucggugag ugauggcaga acgau                                        25

<210> SEQ ID NO 45
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 45
aguuccaugc cugcaggcau cguuc                                        25

<210> SEQ ID NO 46
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 46
gaacgaugcc ugcaggcaug gaacu                                        25

<210> SEQ ID NO 47
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 47
acuggccugg cggagaugcu ucuaa                                        25

<210> SEQ ID NO 48
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 48
uuagaagcau cuccgccagg ccagu                                        25

<210> SEQ ID NO 49
<211> LENGTH: 25
<212> TYPE: RNA

```
<213> ORGANISM: Artificial sequence
<220> FEATURE:
<223> OTHER INFORMATION: Synthetic oligonucleotide

<400> SEQUENCE: 49
gccuggcgga gaugcuucua aggca                                          25

<210> SEQ ID NO 50
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 50
ugccuuagaa gcaucuccgc caggc                                          25

<210> SEQ ID NO 51
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 51
augccuuaga agcaucuccg ccagg                                          25

<210> SEQ ID NO 52
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 52
ccuggcggag augcuucuaa ggcau                                          25

<210> SEQ ID NO 53
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 53
gacaggccag caagtgtgac agtca                                          25

<210> SEQ ID NO 54
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 54
gacaggcgag caagtgtgac agcca                                          25

<210> SEQ ID NO 55
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 55
cagacaggcc agcaagtgtg acagt                                          25
```

<210> SEQ ID NO 56
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 56
cagacaggcg agcaagtgtg acagc                                    25

<210> SEQ ID NO 57
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 57
acagacaggc cagcaagtgt gacag                                    25

<210> SEQ ID NO 58
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 58
acagacaggc gagcaagtgt gacag                                    25

<210> SEQ ID NO 59
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 59
tgcgcagcct gcgcgtgctc aactg                                    25

<210> SEQ ID NO 60
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 60
tgcacagcct gcgtgtgctc aactg                                    25

<210> SEQ ID NO 61
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 61
tgcgcgtgct caactgccaa gggaa                                    25

<210> SEQ ID NO 62
<211> LENGTH: 25
<212> TYPE: DNA
<213> ORGANISM: Artificial sequence
<220> FEATURE:

<223> OTHER INFORMATION: Synthetic oligonucleotide

<400> SEQUENCE: 62
tgcgtgtgct caactgtcaa gggaa                                               25

<210> SEQ ID NO 63
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 63
cataggcctg gagtttattc ggaaa                                               25

<210> SEQ ID NO 64
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 64
cataggcctg gagtttattc ggaag                                               25

<210> SEQ ID NO 65
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 65
tcataggcct ggagtttatt cggaa                                               25

<210> SEQ ID NO 66
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 66
ctcataggcc tggagtttat tcgga                                               25

<210> SEQ ID NO 67
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 67
ctttggccgc tgtgtggacc tcttt                                               25

<210> SEQ ID NO 68
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 68
ttttggacgc tgtgtggatc tcttt                                               25

```
<210> SEQ ID NO 69
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 69
tttggccgct gtgtggacct ctttg                                          25

<210> SEQ ID NO 70
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 70
tttggacgct gtgtggatct ctttg                                          25

<210> SEQ ID NO 71
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 71
cacagacagg ccagcaagtg tgaca                                          25

<210> SEQ ID NO 72
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 72
cacagacagg cgagcaagtg tgaca                                          25

<210> SEQ ID NO 73
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 73
ccacagacag gccagcaagt gtgac                                          25

<210> SEQ ID NO 74
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 74
ccacagacag gcgagcaagt gtgac                                          25

<210> SEQ ID NO 75
<211> LENGTH: 25
<212> TYPE: DNA
<213> ORGANISM: Artificial sequence
<220> FEATURE:
<223> OTHER INFORMATION: Synthetic oligonucleotide
```

-continued

<210> SEQ ID NO 75
<400> SEQUENCE: 75
atgcgcagcc tgcgcgtgct caact                                    25

<210> SEQ ID NO 76
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 76
ctgcacagcc tgcgtgtgct caact                                    25

<210> SEQ ID NO 77
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 77
cctcataggc ctggagttta ttcgg                                    25

<210> SEQ ID NO 78
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 78
ttggccgctg tgtggacctc tttgc                                    25

<210> SEQ ID NO 79
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 79
ttggacgctg tgtggatctc tttgc                                    25

<210> SEQ ID NO 80
<211> LENGTH: 3636
<212> TYPE: DNA
<213> ORGANISM: Homo sapiens
<220> FEATURE:
<221> NAME/KEY: CDS
<222> LOCATION: (292)..(2370)

<400> SEQUENCE: 80
cagcgacgtc gaggcgctca tggttgcagg cgggcgccgc cgttcagttc agggtctgag      60
cctggaggag tgagccaggc agtgagactg gctcgggcgg gccgggacgc gtcgttgcag     120
cagcggctcc cagctcccag ccaggattcc gcgcgcccct tcacgcgccc tgctcctgaa     180
cttcagctcc tgcacagtcc tccccaccgc aaggctcaag gcgccgcggg cgtggaccgc     240
gcacggcctc taggtctcct cgccaggaca gcaacctctc cctggccct c atg ggc       297
                                                        Met Gly
                                                          1 acc gtc agc tcc agg cgg tcc tgg tgg ccg ctg cca ctg ctg ctg ctg       345
Thr Val Ser Ser Arg Arg Ser Trp Trp Pro Leu Pro Leu Leu Leu Leu
          5                  10                  15

-continued

| | | |
|---|---|---|
| ctg ctg ctg ctc ctg ggt ccc gcg ggc gcc cgt gcg cag gag gac gag<br>Leu Leu Leu Leu Leu Gly Pro Ala Gly Ala Arg Ala Gln Glu Asp Glu<br>20  25  30 | 393 |
| gac ggc gac tac gag gag ctg gtg cta gcc ttg cgt tcc gag gag gac<br>Asp Gly Asp Tyr Glu Glu Leu Val Leu Ala Leu Arg Ser Glu Glu Asp<br>35  40  45  50 | 441 |
| ggc ctg gcc gaa gca ccc gag cac gga acc aca gcc acc ttc cac cgc<br>Gly Leu Ala Glu Ala Pro Glu His Gly Thr Thr Ala Thr Phe His Arg<br>55  60  65 | 489 |
| tgc gcc aag gat ccg tgg agg ttg cct ggc acc tac gtg gtg gtg ctg<br>Cys Ala Lys Asp Pro Trp Arg Leu Pro Gly Thr Tyr Val Val Val Leu<br>70  75  80 | 537 |
| aag gag gag acc cac ctc tcg cag tca gag cgc act gcc cgc cgc ctg<br>Lys Glu Glu Thr His Leu Ser Gln Ser Glu Arg Thr Ala Arg Arg Leu<br>85  90  95 | 585 |
| cag gcc cag gct gcc cgc cgg gga tac ctc acc aag atc ctg cat gtc<br>Gln Ala Gln Ala Ala Arg Arg Gly Tyr Leu Thr Lys Ile Leu His Val<br>100  105  110 | 633 |
| ttc cat ggc ctt ctt cct ggc ttc ctg gtg aag atg agt ggc gac ctg<br>Phe His Gly Leu Leu Pro Gly Phe Leu Val Lys Met Ser Gly Asp Leu<br>115  120  125  130 | 681 |
| ctg gag ctg gcc ttg aag ttg ccc cat gtc gac tac atc gag gag gac<br>Leu Glu Leu Ala Leu Lys Leu Pro His Val Asp Tyr Ile Glu Glu Asp<br>135  140  145 | 729 |
| tcc tct gtc ttt gcc cag agc atc ccg tgg aac ctg gag cgg att acc<br>Ser Ser Val Phe Ala Gln Ser Ile Pro Trp Asn Leu Glu Arg Ile Thr<br>150  155  160 | 777 |
| cct cca cgg tac cgg gcg gat gaa tac cag ccc ccc gac gga ggc agc<br>Pro Pro Arg Tyr Arg Ala Asp Glu Tyr Gln Pro Pro Asp Gly Gly Ser<br>165  170  175 | 825 |
| ctg gtg gag gtg tat ctc cta gac acc agc ata cag agt gac cac cgg<br>Leu Val Glu Val Tyr Leu Leu Asp Thr Ser Ile Gln Ser Asp His Arg<br>180  185  190 | 873 |
| gaa atc gag ggc agg gtc atg gtc acc gac ttc gag aat gtg ccc gag<br>Glu Ile Glu Gly Arg Val Met Val Thr Asp Phe Glu Asn Val Pro Glu<br>195  200  205  210 | 921 |
| gag gac ggg acc cgc ttc cac aga cag gcc agc aag tgt gac agt cat<br>Glu Asp Gly Thr Arg Phe His Arg Gln Ala Ser Lys Cys Asp Ser His<br>215  220  225 | 969 |
| ggc acc cac ctg gca ggg gtg gtc agc ggc cgg gat gcc ggc gtg gcc<br>Gly Thr His Leu Ala Gly Val Val Ser Gly Arg Asp Ala Gly Val Ala<br>230  235  240 | 1017 |
| aag ggt gcc agc atg cgc agc ctg cgc gtg ctc aac tgc caa ggg aag<br>Lys Gly Ala Ser Met Arg Ser Leu Arg Val Leu Asn Cys Gln Gly Lys<br>245  250  255 | 1065 |
| ggc acg gtt agc ggc acc ctc ata ggc ctg gag ttt att cgg aaa agc<br>Gly Thr Val Ser Gly Thr Leu Ile Gly Leu Glu Phe Ile Arg Lys Ser<br>260  265  270 | 1113 |
| cag ctg gtc cag cct gtg ggg cca ctg gtg gtg ctg ctg ccc ctg gcg<br>Gln Leu Val Gln Pro Val Gly Pro Leu Val Val Leu Leu Pro Leu Ala<br>275  280  285  290 | 1161 |
| ggt ggg tac agc cgc gtc ctc aac gcc gcc tgc cag cgc ctg gcg agg<br>Gly Gly Tyr Ser Arg Val Leu Asn Ala Ala Cys Gln Arg Leu Ala Arg<br>295  300  305 | 1209 |
| gct ggg gtc gtg ctg gtc acc gct gcc ggc aac ttc cgg gac gat gcc<br>Ala Gly Val Val Leu Val Thr Ala Ala Gly Asn Phe Arg Asp Asp Ala<br>310  315  320 | 1257 |
| tgc ctc tac tcc cca gcc tca gct ccc gag gtc atc aca gtt ggg gcc<br>Cys Leu Tyr Ser Pro Ala Ser Ala Pro Glu Val Ile Thr Val Gly Ala<br>325  330  335 | 1305 |

```
acc aat gcc caa gac cag ccg gtg acc ctg ggg act ttg ggg acc aac    1353
Thr Asn Ala Gln Asp Gln Pro Val Thr Leu Gly Thr Leu Gly Thr Asn
    340             345                 350 ttt ggc cgc tgt gtg gac ctc ttt gcc cca ggg gag gac atc att ggt    1401
Phe Gly Arg Cys Val Asp Leu Phe Ala Pro Gly Glu Asp Ile Ile Gly
355                 360                 365                 370 gcc tcc agc gac tgc agc acc tgc ttt gtg tca cag agt ggg aca tca    1449
Ala Ser Ser Asp Cys Ser Thr Cys Phe Val Ser Gln Ser Gly Thr Ser
                375                 380                 385 cag gct gct gcc cac gtg gct ggc att gca gcc atg atg ctg tct gcc    1497
Gln Ala Ala Ala His Val Ala Gly Ile Ala Ala Met Met Leu Ser Ala
            390                 395                 400 gag ccg gag ctc acc ctg gcc gag ttg agg cag aga ctg atc cac ttc    1545
Glu Pro Glu Leu Thr Leu Ala Glu Leu Arg Gln Arg Leu Ile His Phe
        405                 410                 415 tct gcc aaa gat gtc atc aat gag gcc tgg ttc cct gag gac cag cgg    1593
Ser Ala Lys Asp Val Ile Asn Glu Ala Trp Phe Pro Glu Asp Gln Arg
    420                 425                 430 gta ctg acc ccc aac ctg gtg gcc gcc ctg ccc ccc agc acc cat ggg    1641
Val Leu Thr Pro Asn Leu Val Ala Ala Leu Pro Pro Ser Thr His Gly
435                 440                 445                 450 gca ggt tgg cag ctg ttt tgc agg act gta tgg tca gca cac tcg ggg    1689
Ala Gly Trp Gln Leu Phe Cys Arg Thr Val Trp Ser Ala His Ser Gly
                455                 460                 465 cct aca cgg atg gcc aca gcc gtc gcc cgc tgc gcc cca gat gag gag    1737
Pro Thr Arg Met Ala Thr Ala Val Ala Arg Cys Ala Pro Asp Glu Glu
            470                 475                 480 ctg ctg agc tgc tcc agt ttc tcc agg agt ggg aag cgg cgg ggc gag    1785
Leu Leu Ser Cys Ser Ser Phe Ser Arg Ser Gly Lys Arg Arg Gly Glu
        485                 490                 495 cgc atg gag gcc caa ggg ggc aag ctg gtc tgc cgg gcc cac aac gct    1833
Arg Met Glu Ala Gln Gly Gly Lys Leu Val Cys Arg Ala His Asn Ala
    500                 505                 510 ttt ggg ggt gag ggt gtc tac gcc att gcc agg tgc tgc ctg cta ccc    1881
Phe Gly Gly Glu Gly Val Tyr Ala Ile Ala Arg Cys Cys Leu Leu Pro
515                 520                 525                 530 cag gcc aac tgc agc gtc cac aca gct cca cca gct gag gcc agc atg    1929
Gln Ala Asn Cys Ser Val His Thr Ala Pro Pro Ala Glu Ala Ser Met
                535                 540                 545 ggg acc cgt gtc cac tgc cac caa cag ggc cac gtc ctc aca ggc tgc    1977
Gly Thr Arg Val His Cys His Gln Gln Gly His Val Leu Thr Gly Cys
            550                 555                 560 agc tcc cac tgg gag gtg gag gac ctt ggc acc cac aag ccg cct gtg    2025
Ser Ser His Trp Glu Val Glu Asp Leu Gly Thr His Lys Pro Pro Val
        565                 570                 575 ctg agg cca cga ggt cag ccc aac cag tgc gtg ggc cac agg gag gcc    2073
Leu Arg Pro Arg Gly Gln Pro Asn Gln Cys Val Gly His Arg Glu Ala
    580                 585                 590 agc atc cac gct tcc tgc tgc cat gcc cca ggt ctg gaa tgc aaa gtc    2121
Ser Ile His Ala Ser Cys Cys His Ala Pro Gly Leu Glu Cys Lys Val
595                 600                 605                 610 aag gag cat gga atc ccg gcc cct cag gag cag gtg acc gtg gcc tgc    2169
Lys Glu His Gly Ile Pro Ala Pro Gln Glu Gln Val Thr Val Ala Cys
                615                 620                 625 gag gag ggc tgg acc ctg act ggc tgc agt gcc ctc cct ggg acc tcc    2217
Glu Glu Gly Trp Thr Leu Thr Gly Cys Ser Ala Leu Pro Gly Thr Ser
            630                 635                 640 cac gtc ctg ggg gcc tac gcc gta gac aac acg tgt gta gtc agg agc    2265
His Val Leu Gly Ala Tyr Ala Val Asp Asn Thr Cys Val Val Arg Ser
```

-continued

```
                  645                 650                 655
cgg gac gtc agc act aca ggc agc acc agc gaa ggg gcc gtg aca gcc        2313
Arg Asp Val Ser Thr Thr Gly Ser Thr Ser Glu Gly Ala Val Thr Ala
    660                 665                 670 gtt gcc atc tgc tgc cgg agc cgg cac ctg gcg cag gcc tcc cag gag        2361
Val Ala Ile Cys Cys Arg Ser Arg His Leu Ala Gln Ala Ser Gln Glu
675                 680                 685                 690 ctc cag tga cagccccatc ccaggatggg tgtctgggga gggtcaaggg                2410
Leu Gln ctggggctga gctttaaaat ggttccgact tgtccctctc tcagccctcc atggcctggc      2470
acgaggggat gggatgctt ccgcctttcc ggggctgctg gcctggccct tgagtggggc       2530
agcctccttg cctggaactc actcactctg ggtgcctcct ccccaggtgg aggtgccagg      2590
aagctccctc cctcactgtg gggcatttca ccattcaaac aggtcgagct gtgctcgggt     2650
gctgccagct gctcccaatg tgccgatgtc cgtgggcaga atgactttta ttgagctctt     2710
gttccgtgcc aggcattcaa tcctcaggtc tccaccaagg aggcaggatt cttcccatgg     2770
ataggggagg gggcggtagg ggctgcaggg acaaacatcg ttgggggggtg agtgtgaaag    2830 gtgctgatgg ccctcatctc cagctaactg tggagaagcc cctggggggct ccctgattaa    2890 tggaggctta gctttctgga tggcatctag ccagaggctg agacaggtg cgcccctggt      2950 ggtcacaggc tgtgccttgg tttcctgagc acctttact ctgctctatg ccaggctgtg      3010
ctagcaacac ccaaaggtgg cctgcgggga gccatcacct aggactgact cggcagtgtg     3070
cagtggtgca tgcactgtct cagccaaccc gctccactac ccggcagggt acacattcgc     3130 accctactt cacagaggaa gaaacctgga accagagggg gcgtgcctgc caagctcaca      3190
cagcaggaac tgagccagaa acgcagattg ggctggctct gaagccaagc ctcttcttac     3250
ttcacccggc tgggctcctc attttttacgg gtaacagtga ggctgggaag gggaacacag    3310
accaggaagc tcggtgagtg atggcagaac gatgcctgca ggcatggaac ttttttccgtt    3370 atcacccagg cctgattcac tggcctggcg gagatgcttc taaggcatgg tcgggggaga    3430
gggccaacaa ctgtccctcc ttgagccacca gccccaccca agcaagcaga catttatctt    3490
ttgggtctgt cctctctgtt gccttttttac agccaacttt tctagacctg ttttgctttt    3550
gtaacttgaa gatattatt ctgggttttg tagcattttt attaatatgg tgacttttta      3610
aaataaaaac aaacaaacgt tgtcct                                           3636
```

<210> SEQ ID NO 81
<211> LENGTH: 692
<212> TYPE: PRT
<213> ORGANISM: Homo sapiens

<400> SEQUENCE: 81

Met Gly Thr Val Ser Ser Arg Arg Ser Trp Trp Pro Leu Pro Leu Leu
1               5                   10                  15

Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg

-continued

```
                85                  90                  95
Arg Leu Gln Ala Gln Ala Ala Arg Arg Gly Tyr Leu Thr Lys Ile Leu
            100                 105                 110
His Val Phe His Gly Leu Leu Pro Gly Phe Leu Val Lys Met Ser Gly
            115                 120                 125
Asp Leu Leu Glu Leu Ala Leu Lys Leu Pro His Val Asp Tyr Ile Glu
            130                 135                 140
Glu Asp Ser Ser Val Phe Ala Gln Ser Ile Pro Trp Asn Leu Glu Arg
145                 150                 155                 160
Ile Thr Pro Pro Arg Tyr Arg Ala Asp Glu Tyr Gln Pro Pro Asp Gly
                165                 170                 175
Gly Ser Leu Val Glu Val Tyr Leu Leu Asp Thr Ser Ile Gln Ser Asp
            180                 185                 190
His Arg Glu Ile Glu Gly Arg Val Met Val Thr Asp Phe Glu Asn Val
            195                 200                 205
Pro Glu Glu Asp Gly Thr Arg Phe His Arg Gln Ala Ser Lys Cys Asp
        210                 215                 220
Ser His Gly Thr His Leu Ala Gly Val Val Ser Gly Arg Asp Ala Gly
225                 230                 235                 240
Val Ala Lys Gly Ala Ser Met Arg Ser Leu Arg Val Leu Asn Cys Gln
                245                 250                 255
Gly Lys Gly Thr Val Ser Gly Thr Leu Ile Gly Leu Glu Phe Ile Arg
            260                 265                 270
Lys Ser Gln Leu Val Gln Pro Val Gly Pro Leu Val Val Leu Leu Pro
        275                 280                 285
Leu Ala Gly Gly Tyr Ser Arg Val Leu Asn Ala Ala Cys Gln Arg Leu
        290                 295                 300
Ala Arg Ala Gly Val Val Leu Val Thr Ala Ala Gly Asn Phe Arg Asp
305                 310                 315                 320
Asp Ala Cys Leu Tyr Ser Pro Ala Ser Ala Pro Glu Val Ile Thr Val
                325                 330                 335
Gly Ala Thr Asn Ala Gln Asp Gln Pro Val Thr Leu Gly Thr Leu Gly
            340                 345                 350
Thr Asn Phe Gly Arg Cys Val Asp Leu Phe Ala Pro Gly Glu Asp Ile
        355                 360                 365
Ile Gly Ala Ser Ser Asp Cys Ser Thr Cys Phe Val Ser Gln Ser Gly
        370                 375                 380
Thr Ser Gln Ala Ala Ala His Val Ala Gly Ile Ala Ala Met Met Leu
385                 390                 395                 400
Ser Ala Glu Pro Glu Leu Thr Leu Ala Glu Leu Arg Gln Arg Leu Ile
                405                 410                 415
His Phe Ser Ala Lys Asp Val Ile Asn Glu Ala Trp Phe Pro Glu Asp
            420                 425                 430
Gln Arg Val Leu Thr Pro Asn Leu Val Ala Ala Leu Pro Pro Ser Thr
        435                 440                 445
His Gly Ala Gly Trp Gln Leu Phe Cys Arg Thr Val Trp Ser Ala His
        450                 455                 460
Ser Gly Pro Thr Arg Met Ala Thr Ala Val Ala Arg Cys Ala Pro Asp
465                 470                 475                 480
Glu Glu Leu Leu Ser Cys Ser Ser Phe Ser Arg Ser Gly Lys Arg Arg
                485                 490                 495
Gly Glu Arg Met Glu Ala Gln Gly Gly Lys Leu Val Cys Arg Ala His
            500                 505                 510
```

-continued

```
Asn Ala Phe Gly Gly Glu Gly Val Tyr Ala Ile Ala Arg Cys Cys Leu
            515                 520                 525
Leu Pro Gln Ala Asn Cys Ser Val His Thr Ala Pro Pro Ala Glu Ala
        530                 535                 540
Ser Met Gly Thr Arg Val His Cys His Gln Gly His Val Leu Thr
545                 550                 555                 560
Gly Cys Ser Ser His Trp Glu Val Glu Asp Leu Gly Thr His Lys Pro
                565                 570                 575
Pro Val Leu Arg Pro Arg Gly Gln Pro Asn Gln Cys Val Gly His Arg
            580                 585                 590
Glu Ala Ser Ile His Ala Ser Cys Cys His Ala Pro Gly Leu Glu Cys
        595                 600                 605
Lys Val Lys Glu His Gly Ile Pro Ala Pro Gln Glu Gln Val Thr Val
    610                 615                 620
Ala Cys Glu Glu Gly Trp Thr Leu Thr Gly Cys Ser Ala Leu Pro Gly
625                 630                 635                 640
Thr Ser His Val Leu Gly Ala Tyr Ala Val Asp Asn Thr Cys Val Val
                645                 650                 655
Arg Ser Arg Asp Val Ser Thr Thr Gly Ser Thr Ser Glu Gly Ala Val
            660                 665                 670
Thr Ala Val Ala Ile Cys Cys Arg Ser Arg His Leu Ala Gln Ala Ser
        675                 680                 685
Gln Glu Leu Gln
    690
```

<210> SEQ ID NO 82
<211> LENGTH: 3512
<212> TYPE: DNA
<213> ORGANISM: Mus musculus
<220> FEATURE:
<221> NAME/KEY: CDS
<222> LOCATION: (416)..(2500)

<400> SEQUENCE: 82

```
tggggattaa gagggggggaa tgtaacaggt cccgtttgca gcccaattag gatttggggt      60
tttgtcctca ctctgagcgt catttgacgc tgtctgggga gggcgaggcc gaaacctgat     120
cctttagtac cggggcccgt taatgtttaa tcagagagga tcttccgatg gggctcgggg     180
tggcgtgatc tcccggcccc caggcgtcca gtacccacac cccagaaggc ttccaccttc     240
acgtggacgc gcaggctgcc ggtgggctcc cgttctctct ctctttctga ggctagagga     300
ctgagccagt ccttggctcc ccagagacat cacggcccgc agccccggag ccaagtgccc     360
cgagtcccag gcgtccatgt ccttcccgag gccgcgcgca cctctcctcg ccccg atg     418
                                                              Met
                                                                1 ggc acc cac tgc tct gcg tgg ctg cgg tgg ccg ctg ttg ccg ctg ttg     466
Gly Thr His Cys Ser Ala Trp Leu Arg Trp Pro Leu Leu Pro Leu Leu
              5                  10                  15 ccg ccg ctg ctg ctg ctg ttg ctg cta ctg tgc ccc acc ggc gct ggt     514
Pro Pro Leu Leu Leu Leu Leu Leu Leu Cys Pro Thr Gly Ala Gly
         20                  25                  30 gcc cag gac gag gat gga gat tat gaa gag ctg atg ctc gcc ctc ccg     562
Ala Gln Asp Glu Asp Gly Asp Tyr Glu Glu Leu Met Leu Ala Leu Pro
     35                  40                  45 tcc cag gag gat ggc ctg gct gat gag gcc gca cat gtg gcc acc gcc     610
Ser Gln Glu Asp Gly Leu Ala Asp Glu Ala Ala His Val Ala Thr Ala
50                  55                  60                  65
```

```
acc ttc cgc cgt tgc tcc aag gag gcc tgg agg ctg cca gga acc tac        658
Thr Phe Arg Arg Cys Ser Lys Glu Ala Trp Arg Leu Pro Gly Thr Tyr
            70                  75                  80 att gtg gtg ctg atg gag gag acc cag agg cta cag att gaa caa act        706
Ile Val Val Leu Met Glu Glu Thr Gln Arg Leu Gln Ile Glu Gln Thr
        85                  90                  95 gcc cac cgc ctg cag acc cgg gct gcc cgc cgg ggc tat gtc atc aag        754
Ala His Arg Leu Gln Thr Arg Ala Ala Arg Arg Gly Tyr Val Ile Lys
    100                 105                 110 gtt cta cat atc ttt tat gac ctc ttc cct ggc ttc ttg gtg aag atg        802
Val Leu His Ile Phe Tyr Asp Leu Phe Pro Gly Phe Leu Val Lys Met
115                 120                 125 agc agt gac ctg ttg ggc ctg gcc ctg aag ttg ccc cat gtg gag tac        850
Ser Ser Asp Leu Leu Gly Leu Ala Leu Lys Leu Pro His Val Glu Tyr
130                 135                 140                 145 att gag gaa gac tcc ttt gtc ttc gcc cag agc atc cca tgg aac ctg        898
Ile Glu Glu Asp Ser Phe Val Phe Ala Gln Ser Ile Pro Trp Asn Leu
            150                 155                 160 gag cga att atc cca gca tgg cac cag aca gag gaa gac cgc tcc cct        946
Glu Arg Ile Ile Pro Ala Trp His Gln Thr Glu Glu Asp Arg Ser Pro
        165                 170                 175 gat gga agc agc cag gtg gag gtg tat ctc tta gat acc agc atc cag        994
Asp Gly Ser Ser Gln Val Glu Val Tyr Leu Leu Asp Thr Ser Ile Gln
    180                 185                 190 ggt gcc cat cgg gag att gag ggc agg gtc acc atc acc gac ttc aac       1042
Gly Ala His Arg Glu Ile Glu Gly Arg Val Thr Ile Thr Asp Phe Asn
195                 200                 205 agc gtg ccg gag gag gat ggg aca cgc ttc cac aga cag gcg agc aag       1090
Ser Val Pro Glu Glu Asp Gly Thr Arg Phe His Arg Gln Ala Ser Lys
210                 215                 220                 225 tgt gac agc cac ggc acc cac ctg gca ggt gtg gtc agc ggc cgg gat       1138
Cys Asp Ser His Gly Thr His Leu Ala Gly Val Val Ser Gly Arg Asp
            230                 235                 240 gct ggt gtg gcc aag ggc acc agc ctg cac agc ctg cgt gtg ctc aac       1186
Ala Gly Val Ala Lys Gly Thr Ser Leu His Ser Leu Arg Val Leu Asn
        245                 250                 255 tgt caa ggg aag ggc aca gtc agc ggc acc ctc ata ggc ctg gag ttt       1234
Cys Gln Gly Lys Gly Thr Val Ser Gly Thr Leu Ile Gly Leu Glu Phe
    260                 265                 270 att cgg aag agt cag cta atc cag ccc tcg ggg cca ctc gtg gtt ctg       1282
Ile Arg Lys Ser Gln Leu Ile Gln Pro Ser Gly Pro Leu Val Val Leu
275                 280                 285 ctg ccc ctg gcc ggt ggg tat agc cgc atc ctc aac gct gcc tgc cgg       1330
Leu Pro Leu Ala Gly Gly Tyr Ser Arg Ile Leu Asn Ala Ala Cys Arg
290                 295                 300                 305 cac ctg gcg agg act ggg gtg gtg ctg gtt gca gca gct ggg aac ttc       1378
His Leu Ala Arg Thr Gly Val Val Leu Val Ala Ala Ala Gly Asn Phe
            310                 315                 320 cgg gac gac gcc tgc ctc tac tcc cca gct tct gct cca gag gtc atc       1426
Arg Asp Asp Ala Cys Leu Tyr Ser Pro Ala Ser Ala Pro Glu Val Ile
        325                 330                 335 aca gtc ggg gcc acg aat gcc cag gac cag cca gtt acc ttg ggg act       1474
Thr Val Gly Ala Thr Asn Ala Gln Asp Gln Pro Val Thr Leu Gly Thr
    340                 345                 350 ttg ggg act aat ttt gga cgc tgt gtg gat ctc ttt gcc ccc ggg aag       1522
Leu Gly Thr Asn Phe Gly Arg Cys Val Asp Leu Phe Ala Pro Gly Lys
355                 360                 365 gac atc atc gga gcg tcc agt gac tgc agc aca tgc ttc atg tca cag       1570
Asp Ile Ile Gly Ala Ser Ser Asp Cys Ser Thr Cys Phe Met Ser Gln
```

```
            370                 375                 380                 385
agt ggg acc tca cag gct gct gcc cac gtg gcc ggc att gtg gct cgg           1618
Ser Gly Thr Ser Gln Ala Ala Ala His Val Ala Gly Ile Val Ala Arg
                    390                 395                 400 atg ctg agc cgg gag ccc aca ctt acc ctg gcc gag ctg cgg cag agg           1666
Met Leu Ser Arg Glu Pro Thr Leu Thr Leu Ala Glu Leu Arg Gln Arg
            405                 410                 415 ctg atc cac ttc tct acc aaa gac gtc atc aac atg gcc tgg ttc cct           1714
Leu Ile His Phe Ser Thr Lys Asp Val Ile Asn Met Ala Trp Phe Pro
        420                 425                 430 gag gac cag cag gtg ctg acc ccc aac ctg gtg gcc aca ctg ccc ccc           1762
Glu Asp Gln Gln Val Leu Thr Pro Asn Leu Val Ala Thr Leu Pro Pro
    435                 440                 445 agc acc cat gag aca ggc ggg cag ctg ctc tgt agg acg gtg tgg tcg           1810
Ser Thr His Glu Thr Gly Gly Gln Leu Leu Cys Arg Thr Val Trp Ser
450                 455                 460                 465 gca cac tcg ggg ccc act cga aca gct aca gct aca gcc cgc tgt gcc           1858
Ala His Ser Gly Pro Thr Arg Thr Ala Thr Ala Thr Ala Arg Cys Ala
                470                 475                 480 cca gaa gag gag ctg ctg agc tgc tcc agc ttc tcc agg agc ggg agg           1906
Pro Glu Glu Glu Leu Leu Ser Cys Ser Ser Phe Ser Arg Ser Gly Arg
            485                 490                 495 cgt cgt ggt gat tgg att gag gcc ata gga ggc cag cag gtc tgc aag           1954
Arg Arg Gly Asp Trp Ile Glu Ala Ile Gly Gly Gln Gln Val Cys Lys
        500                 505                 510 gcc ctc aat gca ttt ggg ggt gag ggt gtc tat gcc gtc gcg aga tgc           2002
Ala Leu Asn Ala Phe Gly Gly Glu Gly Val Tyr Ala Val Ala Arg Cys
    515                 520                 525 tgc ctg gtt ccc cgt gcc aac tgc agc atc cac aac acc cct gca gcc           2050
Cys Leu Val Pro Arg Ala Asn Cys Ser Ile His Asn Thr Pro Ala Ala
530                 535                 540                 545 aga gct ggc ctg gag acc cat gtc cac tgc cac cag aag gac cat gtt           2098
Arg Ala Gly Leu Glu Thr His Val His Cys His Gln Lys Asp His Val
                550                 555                 560 ctc aca ggc tgc agc ttc cat tgg gaa gtg gaa gac ctt agt gtc cgg           2146
Leu Thr Gly Cys Ser Phe His Trp Glu Val Glu Asp Leu Ser Val Arg
            565                 570                 575 agg cag cct gcg ctg agg tcc aga cgt cag cct ggc cag tgc gtt ggc           2194
Arg Gln Pro Ala Leu Arg Ser Arg Arg Gln Pro Gly Gln Cys Val Gly
        580                 585                 590 cac cag gcg gcc agt gtc tat gct tcc tgc tgc cat gcc cca ggg ctg           2242
His Gln Ala Ala Ser Val Tyr Ala Ser Cys Cys His Ala Pro Gly Leu
    595                 600                 605 gaa tgc aaa atc aag gag cat ggg atc tca ggt cct tca gag cag gtc           2290
Glu Cys Lys Ile Lys Glu His Gly Ile Ser Gly Pro Ser Glu Gln Val
610                 615                 620                 625 act gtg gcc tgc gaa gca gga tgg acc ctg act gga tgc aat gtg ctc           2338
Thr Val Ala Cys Glu Ala Gly Trp Thr Leu Thr Gly Cys Asn Val Leu
                630                 635                 640 cct ggg gca tcc ctc act ctg gga gcc tac agc gtg gac aac ctg tgt           2386
Pro Gly Ala Ser Leu Thr Leu Gly Ala Tyr Ser Val Asp Asn Leu Cys
            645                 650                 655 gtg gca aga gtc cat gac act gcc aga gca gac agg acc agt gga gaa           2434
Val Ala Arg Val His Asp Thr Ala Arg Ala Asp Arg Thr Ser Gly Glu
        660                 665                 670 gcc aca gta gct gct gcc atc tgc tgc cgg agc cgg cct tca gca aag           2482
Ala Thr Val Ala Ala Ala Ile Cys Cys Arg Ser Arg Pro Ser Ala Lys
    675                 680                 685 gcc tcc tgg gtt cag tga cagcctcagg cagggatggt gcttgaggct                  2530
Ala Ser Trp Val Gln
```

```
Ala Ser Trp Val Gln
690 gggtgcagag atatgcctgc atggctctct tgtagccaaa ggtggggaga ttctgcgtgg    2590 gagaacttgg tgtctcaccc tgggtaccca ttcctggtgt atggaagcac ctccttcacg    2650 gtcaggggc ctgtgcttgg ctttctgcca tcagacatta agctgtagct ggctctggcc     2710 agctgctcca gtgtaccaga acctgaggat gctcgctgca aggcctcagt tctcaggcct    2770 tagggtgtat ttgtctttca ggaagatcat aatggacaga gatccttgga ggttcaaaga    2830 ccaagtacca gactggaaaa ttgagtctga aagccacaag gacagtcaac tcacagccag    2890 ctcacattgc agacaccatt ttgggctccc tgattaaatg cagatcagtt ctgcacacct    2950 ccaggggtgg atccagctgt aaggccatac ctatatcttc cagatgtcct catctgctgc    3010 agggctttgg ccctgctcag gataatgtgc tatgagccct catctgactc tcagtttgta    3070 ctggagaacc atacaggact taccgcacct taccccatcc actaccatgt gcactgactg    3130 gcctcatttt atgaaggaag agacaggacc agagaggcga tgtcacacag ccagtgatgt    3190 caggacataa attcagagtg gctggccctg aataatgcca ggctgggcag cgagaggaca    3250 ggctatggct tgctcctgga cctatactcc cttagcccca gtcccacaga tcaggtggag    3310 actggagtga cagagggcga ctgtaccaag gccacaccag ctgaccagca cacctctatc    3370 cttttgagct cttctgtctt tttatagtaa gcttcctcca cctgtgttgc ttttgtaact    3430 tgatatttat gcagggtttt gtagtttta ttatgtagtg acttttcaga ataaaagcag     3490 ctgatgtgac tgactgcatc cg                                              3512

<210> SEQ ID NO 83
<211> LENGTH: 694
<212> TYPE: PRT
<213> ORGANISM: Mus musculus

<400> SEQUENCE: 83

Met Gly Thr His Cys Ser Ala Trp Leu Arg Trp Pro Leu Leu Pro Leu
1               5                   10                  15

Leu Pro Pro Leu Leu Leu Leu Leu Leu Leu Cys Pro Thr Gly Ala
            20                  25                  30

Gly Ala Gln Asp Glu Asp Gly Asp Tyr Glu Glu Leu Met Leu Ala Leu
        35                  40                  45

Pro Ser Gln Glu Asp Gly Leu Ala Asp Glu Ala Ala His Val Ala Thr
    50                  55                  60

Ala Thr Phe Arg Arg Cys Ser Lys Glu Ala Trp Arg Leu Pro Gly Thr
65                  70                  75                  80

Tyr Ile Val Val Leu Met Glu Glu Thr Gln Arg Leu Gln Ile Glu Gln
                85                  90                  95

Thr Ala His Arg Leu Gln Thr Arg Ala Ala Arg Arg Gly Tyr Val Ile
            100                 105                 110

Lys Val Leu His Ile Phe Tyr Asp Leu Phe Pro Gly Phe Leu Val Lys
        115                 120                 125

Met Ser Ser Asp Leu Leu Gly Leu Ala Leu Lys Leu Pro His Val Glu
    130                 135                 140

Tyr Ile Glu Glu Asp Ser Phe Val Phe Ala Gln Ser Ile Pro Trp Asn
145                 150                 155                 160

Leu Glu Arg Ile Ile Pro Ala Trp His Gln Thr Glu Glu Asp Arg Ser
                165                 170                 175

Pro Asp Gly Ser Ser Gln Val Glu Val Tyr Leu Leu Asp Thr Ser Ile
```

```
                180                 185                 190
Gln Gly Ala His Arg Glu Ile Glu Gly Arg Val Thr Ile Thr Asp Phe
            195                 200                 205
Asn Ser Val Pro Glu Glu Asp Gly Thr Arg Phe His Arg Gln Ala Ser
        210                 215                 220
Lys Cys Asp Ser His Gly Thr His Leu Ala Gly Val Val Ser Gly Arg
225                 230                 235                 240
Asp Ala Gly Val Ala Lys Gly Thr Ser Leu His Ser Leu Arg Val Leu
                245                 250                 255
Asn Cys Gln Gly Lys Gly Thr Val Ser Gly Thr Leu Ile Gly Leu Glu
            260                 265                 270
Phe Ile Arg Lys Ser Gln Leu Ile Gln Pro Ser Gly Pro Leu Val Val
        275                 280                 285
Leu Leu Pro Leu Ala Gly Gly Tyr Ser Arg Ile Leu Asn Ala Ala Cys
        290                 295                 300
Arg His Leu Ala Arg Thr Gly Val Val Leu Val Ala Ala Ala Gly Asn
305                 310                 315                 320
Phe Arg Asp Asp Ala Cys Leu Tyr Ser Pro Ala Ser Ala Pro Glu Val
                325                 330                 335
Ile Thr Val Gly Ala Thr Asn Ala Gln Asp Gln Pro Val Thr Leu Gly
            340                 345                 350
Thr Leu Gly Thr Asn Phe Gly Arg Cys Val Asp Leu Phe Ala Pro Gly
        355                 360                 365
Lys Asp Ile Ile Gly Ala Ser Ser Asp Cys Ser Thr Cys Phe Met Ser
    370                 375                 380
Gln Ser Gly Thr Ser Gln Ala Ala Ala His Val Ala Gly Ile Val Ala
385                 390                 395                 400
Arg Met Leu Ser Arg Glu Pro Thr Leu Thr Leu Ala Glu Leu Arg Gln
                405                 410                 415
Arg Leu Ile His Phe Ser Thr Lys Asp Val Ile Asn Met Ala Trp Phe
            420                 425                 430
Pro Glu Asp Gln Gln Val Leu Thr Pro Asn Leu Val Ala Thr Leu Pro
        435                 440                 445
Pro Ser Thr His Glu Thr Gly Gly Gln Leu Leu Cys Arg Thr Val Trp
    450                 455                 460
Ser Ala His Ser Gly Pro Thr Arg Thr Ala Thr Ala Thr Ala Arg Cys
465                 470                 475                 480
Ala Pro Glu Glu Glu Leu Leu Ser Cys Ser Ser Phe Ser Arg Ser Gly
                485                 490                 495
Arg Arg Arg Gly Asp Trp Ile Glu Ala Ile Gly Gly Gln Gln Val Cys
            500                 505                 510
Lys Ala Leu Asn Ala Phe Gly Gly Glu Gly Val Tyr Ala Val Ala Arg
        515                 520                 525
Cys Cys Leu Val Pro Arg Ala Asn Cys Ser Ile His Asn Thr Pro Ala
    530                 535                 540
Ala Arg Ala Gly Leu Glu Thr His Val His Cys His Gln Lys Asp His
545                 550                 555                 560
Val Leu Thr Gly Cys Ser Phe His Trp Glu Val Glu Asp Leu Ser Val
                565                 570                 575
Arg Arg Gln Pro Ala Leu Arg Ser Arg Arg Gln Pro Gly Gln Cys Val
            580                 585                 590
Gly His Gln Ala Ala Ser Val Tyr Ala Ser Cys Cys His Ala Pro Gly
        595                 600                 605
```

```
Leu Glu Cys Lys Ile Lys Glu His Gly Ile Ser Gly Pro Ser Glu Gln
        610                 615                 620

Val Thr Val Ala Cys Glu Ala Gly Trp Thr Leu Thr Gly Cys Asn Val
625                 630                 635                 640

Leu Pro Gly Ala Ser Leu Thr Leu Gly Ala Tyr Ser Val Asp Asn Leu
                645                 650                 655

Cys Val Ala Arg Val His Asp Thr Ala Arg Ala Asp Arg Thr Ser Gly
                660                 665                 670

Glu Ala Thr Val Ala Ala Ile Cys Cys Arg Ser Arg Pro Ser Ala
        675                 680                 685

Lys Ala Ser Trp Val Gln
    690

<210> SEQ ID NO 84
<211> LENGTH: 13
<212> TYPE: RNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: 2'-O-methyl
<220> FEATURE:
<221> NAME/KEY: misc_feature
<222> LOCATION: (7)..(9)
<223> OTHER INFORMATION: 2'-O-methyl
<220> FEATURE:
<221> NAME/KEY: misc_feature
<222> LOCATION: (13)..(13)
<223> OTHER INFORMATION: 3'-cholesterol

<400> SEQUENCE: 84
aguuuauucg gaa                                                              13

<210> SEQ ID NO 85
<211> LENGTH: 19
<212> TYPE: RNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5'-Phosphate
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(4)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (12)..(15)
<223> OTHER INFORMATION: 2'-deoxy-2'-fluoro
<220> FEATURE:
<221> NAME/KEY: misc_feature
<222> LOCATION: (14)..(19)
<223> OTHER INFORMATION: phosphorothioate linkage

<400> SEQUENCE: 85
uuccgaauaa acuccaggc                                                        19
```

```
<210> SEQ ID NO 86
<211> LENGTH: 13
<212> TYPE: RNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (13)..(13)
<223> OTHER INFORMATION: 3'-cholesterol

<400> SEQUENCE: 86
caagugugac agu                                                        13

<210> SEQ ID NO 87
<211> LENGTH: 19
<212> TYPE: RNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5'-Phosphate
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(3)
<223> OTHER INFORMATION: 2'-deoxy-2'-fluoro
<220> FEATURE:
<221> NAME/KEY: misc_feature
<222> LOCATION: (5)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (10)..(12)
<223> OTHER INFORMATION: 2'-deoxy-2'-fluoro
<220> FEATURE:
<221> NAME/KEY: misc_feature
<222> LOCATION: (14)..(15)
<223> OTHER INFORMATION: 2'-deoxy-2'-fluoro
<220> FEATURE:
<221> NAME/KEY: misc_feature
<222> LOCATION: (14)..(19)
<223> OTHER INFORMATION: Phosphorothioate linkage
<220> FEATURE:
<221> NAME/KEY: misc_feature
<222> LOCATION: (18)..(18)
<223> OTHER INFORMATION: 2'-deoxy-2'-fluoro
```

<400> SEQUENCE: 87
acugucacac uugcuggcc                                                    19

<210> SEQ ID NO 88
<211> LENGTH: 15
<212> TYPE: RNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(7)
<223> OTHER INFORMATION: 2'-O-methyl
<220> FEATURE:
<221> NAME/KEY: misc_feature
<222> LOCATION: (9)..(11)
<223> OTHER INFORMATION: 2'-O-methyl
<220> FEATURE:
<221> NAME/KEY: misc_feature
<222> LOCATION: (15)..(15)
<223> OTHER INFORMATION: 3'-cholesterol

<400> SEQUENCE: 88
ggaguuuauu cggaa                                                        15

<210> SEQ ID NO 89
<211> LENGTH: 19
<212> TYPE: RNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5'-Phosphate
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(4)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (12)..(15)
<223> OTHER INFORMATION: 2'-deoxy-2'-fluoro
<220> FEATURE:
<221> NAME/KEY: misc_feature
<222> LOCATION: (14)..(19)
<223> OTHER INFORMATION: phosphorothioate linkage

<400> SEQUENCE: 89
uuccgaauaa acuccaggc                                                    19

<210> SEQ ID NO 90
<211> LENGTH: 15
<212> TYPE: RNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (5)..(5)

```
<223> OTHER INFORMATION: 2'-O-methyl
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (13)..(14)
<223> OTHER INFORMATION: 2'-O-methyl
<220> FEATURE:
<221> NAME/KEY: misc_feature
<222> LOCATION: (15)..(15)
<223> OTHER INFORMATION: 3'-cholesterol

<400> SEQUENCE: 90
caagugugac aguca                                                    15

<210> SEQ ID NO 91
<211> LENGTH: 19
<212> TYPE: RNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5'-Phosphate
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (4)..(5)
<223> OTHER INFORMATION: 2'-deoxy-2'-fluoro
<220> FEATURE:
<221> NAME/KEY: misc_feature
<222> LOCATION: (7)..(8)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (12)..(14)
<223> OTHER INFORMATION: 2'-deoxy-2'-fluoro
<220> FEATURE:
<221> NAME/KEY: misc_feature
<222> LOCATION: (14)..(19)
<223> OTHER INFORMATION: Phosphorothioate linkage
<220> FEATURE:
<221> NAME/KEY: misc_feature
<222> LOCATION: (16)..(17)
<223> OTHER INFORMATION: 2'-deoxy-2'-fluoro

<400> SEQUENCE: 91
ugacugucac acuugcugg                                                19

<210> SEQ ID NO 92
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 92
cagaggaaga aaccuggaac cagag                                         25
```

```
<210> SEQ ID NO 93
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 93
ccaagcucac acagcaggaa cugag                                              25

<210> SEQ ID NO 94
<211> LENGTH: 13
<212> TYPE: RNA
<213> ORGANISM: Artificial sequence
<220> FEATURE:
<223> OTHER INFORMATION: Synthetic oligonucleotide

<400> SEQUENCE: 94
aguuuauucg gaa                                                           13

<210> SEQ ID NO 95
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 95
uuccgaauaa acuccaggc                                                     19

<210> SEQ ID NO 96
<211> LENGTH: 13
<212> TYPE: RNA
<213> ORGANISM: Artificial sequence
<220> FEATURE:
<223> OTHER INFORMATION: Synthetic oligonucleotide

<400> SEQUENCE: 96
caagugugac agu                                                           13

<210> SEQ ID NO 97
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 97
acugucacac uugcuggcc                                                     19

<210> SEQ ID NO 98
<211> LENGTH: 15
<212> TYPE: RNA
<213> ORGANISM: Artificial sequence
<220> FEATURE:
<223> OTHER INFORMATION: Synthetic oligonucleotide

<400> SEQUENCE: 98
ggaguuuauu cggaa                                                         15

<210> SEQ ID NO 99
<211> LENGTH: 19
<212> TYPE: RNA
<213> ORGANISM: Artificial sequence
<220> FEATURE:
<223> OTHER INFORMATION: Synthetic oligonucleotide
```

```
<400> SEQUENCE: 99
uuccgaauaa acuccaggc                                                19

<210> SEQ ID NO 100
<211> LENGTH: 15
<212> TYPE: RNA
<213> ORGANISM: Artificial sequence
<220> FEATURE:
<223> OTHER INFORMATION: Synthetic oligonucleotide

<400> SEQUENCE: 100
caagugugac aguca                                                    15

<210> SEQ ID NO 101
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 101
ugacugucac acuugcugg                                                19
```